(12) United States Patent
Kozikowski et al.

(10) Patent No.: US 10,407,381 B2
(45) Date of Patent: Sep. 10, 2019

(54) CYCLOPROPYLMETHANAMINES AS SELECTIVE 5-HT(2C) RECEPTOR AGONISTS

(71) Applicant: THE BOARD OF TRUSTEES OF THE UNIVERSITY OF ILLINOIS, Urbana, IL (US)

(72) Inventors: Alan Kozikowski, Chicago, IL (US); Jianjun Cheng, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 15/544,548

(22) PCT Filed: Jan. 27, 2016

(86) PCT No.: PCT/US2016/015019
§ 371 (c)(1),
(2) Date: Jul. 19, 2017

(87) PCT Pub. No.: WO2016/123164
PCT Pub. Date: Aug. 4, 2016

(65) Prior Publication Data
US 2018/0265453 A1 Sep. 20, 2018

Related U.S. Application Data

(60) Provisional application No. 62/109,104, filed on Jan. 29, 2015.

(51) Int. Cl.
*C07C 211/27* (2006.01)
*A61K 31/125* (2006.01)
*C07C 217/74* (2006.01)
*A61K 31/135* (2006.01)
*C07C 323/12* (2006.01)

(52) U.S. Cl.
CPC .......... *C07C 217/74* (2013.01); *A61K 31/135* (2013.01); *C07C 323/12* (2013.01); *C07C 2601/02* (2017.05)

(58) Field of Classification Search
CPC ................. C07C 217/74; C07C 323/12
See application file for complete search history.

(56) References Cited

U.S. PATENT DOCUMENTS

| | | | |
|---|---|---|---|
| 5,753,709 A * | 5/1998 | Keavy | C07C 233/13 514/520 |
| 6,777,407 B2 | 8/2004 | Sabb et al. | |
| 6,953,787 B2 | 10/2005 | Smith et al. | |
| 6,962,939 B1 | 11/2005 | Roffey et al. | |
| 7,012,089 B2 | 3/2006 | Gao et al. | |
| 7,071,185 B2 | 7/2006 | Ramamoorthy et al. | |
| 8,492,591 B2 * | 7/2013 | Kozikowski | A61K 31/138 564/152 |
| 8,754,132 B2 * | 6/2014 | Kozikowski | A61K 31/138 514/649 |
| 8,765,767 B2 * | 7/2014 | Mattson | C07D 471/04 514/256 |
| 9,682,980 B2 * | 6/2017 | Mattson | C07D 487/04 |
| 2002/0032199 A1 | 3/2002 | Poss et al. | |
| 2005/0020573 A1 | 1/2005 | Smith et al. | |
| 2005/0026925 A1 | 2/2005 | Blench et al. | |
| 2005/0143452 A1 | 6/2005 | Gross et al. | |
| 2005/0197380 A1 | 9/2005 | Roffey et al. | |
| 2005/0261286 A1 * | 11/2005 | Konetzki | C07C 215/60 514/230.5 |
| 2005/0261347 A1 | 11/2005 | Gross et al. | |
| 2006/0154290 A1 | 7/2006 | Magness et al. | |
| 2009/0203750 A1 * | 8/2009 | Kozikowski | A61K 31/137 514/357 |
| 2010/0324147 A1 * | 12/2010 | McCafferty | C07C 217/74 514/647 |
| 2012/0004262 A1 * | 1/2012 | Guibourt | C07C 211/40 514/311 |
| 2013/0079417 A1 * | 3/2013 | Kozikowski | A61K 31/138 514/646 |
| 2013/0178520 A1 * | 7/2013 | McCafferty | C07D 317/58 514/466 |

FOREIGN PATENT DOCUMENTS

| | | | | |
|---|---|---|---|---|
| EP | | 0747346 A2 * | 12/1996 | ........... C07C 233/13 |
| WO | WO-2000/035922 A1 | | 6/2000 | |
| WO | WO-2005/007614 A1 | | 1/2005 | |
| WO | WO-2006/065600 A2 | | 6/2006 | |
| WO | WO-2006/077025 A2 | | 7/2006 | |
| WO | WO-2007/025144 A1 | | 3/2007 | |
| WO | WO-2013/138687 A1 | | 9/2013 | |

(Continued)

OTHER PUBLICATIONS

Cheng et al. Tetrahedron Letters 56(23), 3420-3422 (2015). (Year: 2015).*
"Lorcaserin. In obesity: unacceptable risks", Prescrire Int., 23(149):117-20 (2014).
Aronov, Predictive in silico modeling for hERG channel blockers, Drug Discov. Today, 10(2):149-55 (2005).

(Continued)

*Primary Examiner* — Nyeemah A Grazier

(74) *Attorney, Agent, or Firm* — Marshall, Gerstein & Borun LLP

(57) ABSTRACT

Disclosed are 2-phenyl-cyclopropylmethanamines which are selective 5-HT(2C) receptor agonists and are used in the treatments of diseases and conditions wherein modulation of 5-HT(2C) receptors provides a benefit, such as obesity and psychiatric disorders.

14 Claims, 1 Drawing Sheet

(56) References Cited

FOREIGN PATENT DOCUMENTS

WO     WO-2013192306 A1 * 12/2013     .......... C07D 487/04

OTHER PUBLICATIONS

Berg et al., Fine-tuning serotonin2c receptor function in the brain: molecular and functional implications, Neuropharmacology, 55(6):969-76 (2008).
Berger et al., The expanded biology of serotonin, Annu. Rev. Med., 60:355-66 (2009).
Callahan et al., Involvement of 5-HT2C receptors in mediating the discriminative stimulus properties of m-chlorophenylpiperazine (mCPP), Eur. J. Pharmacol., 257(1-2):27-38 (1994).
Chen et al., Rational Drug Design Leading to the Identification of a Potent 5-HT(2C) Agonist Lacking 5-HT(2B) Activity, ACS Med. Chem. Lett., 2(12):929-32 (2011).
Cheng et al., Design and Synthesis of (2-(5-Chloro-2,2-dimethyl-2,3-dihydrobenzofuran-7-yl)cyclopropyl)methanamine as a Selective Serotonin 2C Agonist, Tetrahedron Lett., 56(23):3420-2 (2015).
Cheng et al., Optimization of 2-phenylcyclopropylmethylamines as selective serotonin 2C receptor agonists and their evaluation as potential antipsychotic agents, J. Med. Chem., 58(4):1992-2002 (2015).
Cho et al., Selective 5-hydroxytryptamine 2C receptor agonists derived from the lead compound tranylcypromine: identification of drugs with antidepressant-like action, J. Med. Chem., 52(7):1885-902 (2009).
Di Giovanni et al., Preferential modulation of mesolimbic vs. nigrostriatal dopaminergic function by serotonin(2C/2B) receptor agonists: a combined in vivo electrophysiological and microdialysis study, Synapse, 35(1):53-61 (2000).
Dunlop et al., Characterization of vabicaserin (SCA-136), a selective 5-hydroxytryptamine 2C receptor agonist, J. Pharmacol. Exp. Ther., 337(3):673-80 (2011).
Fiorella et al., 5-HT2C receptor-mediated phosphoinositide turnover and the stimulus effects of m-chlorophenylpipera, Psychopharmacology (Berl.), 122(3):237-43 (1995).
International Search Report and Written Opinion, International Application No. PCT/US16/015019, dated May 25, 2016.
Kalgutkar et al., Genotoxicity of 2-(3-chlorobenzyloxy)-6-(piperazinyl)pyrazine, a novel 5-hydroxytryptamine2c receptor agonist for the treatment of obesity: role of metabolic activation, Drug Metab. Dispos., 33(6):848-58 (2007).
Kozikowski et al., HTS and rational drug design to generate a class of 5-HT(2C)-selective ligands for possible use in schizophrenia, ChemMedChem., 5(8):1221-5 (2010).
Lee et al., 5-HT2C receptor modulators: a patent survey, Expert Opin. Ther. Pat., 20(11):1429-55 (2010).
Leysen, 5-HT2 receptors, Curr. Drug Targets CNS Neurol. Disord., 3(1):11-26 (2004).
Liu et al., Prediction of Efficacy of Vabicaserin, a 5-HT2C Agonist, for the Treatment of Schizophrenia Using a Quantitative Systems Pharmacology Model, CPT Pharmacometrics Syst. Pharmacol., 3:e111 (2014).
Ma et al., Asymmetric dipolar cycloaddition reactions: a practical, convergent synthesis of chiral pyrrolidines, Tetrahedron: Asymmetry, 8(6):883-7 (1997).
Marquis et al., WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity, J. Pharmacol. Exp. Ther., 320(1):486-96 (2007).
Meltzer et al., Lorcaserin and pimavanserin: emerging selectivity of serotonin receptor subtype-targeted drugs, J. Clin. Invest., 123(12):4986-91 (2013).
Millan et al., Serotonin (5-HT)2C receptors tonically inhibit dopamine (DA) and noradrenaline (NA), but not 5-HT, release in the frontal cortex in vivo, Neuropharmacology, 37(7):953-5 (1998).
Mombereau et al., Functional relevance of serotonin 2C receptor mRNA editing in antidepressant- and anxiety-like behaviors, Neuropharmacology, 59(6):468-73 (2010).
Nichols et al., Serotonin receptors, Chem. Rev., 108(5):1614-41 (2008).
Nichols, Hallucinogens, Pharmacol. Ther., 101(2):131-81 (2004).
Pazos et al., The binding of serotonergic ligands to the porcine choroid plexus: characterization of a new type of serotonin recognition site, Eur. J. Pharmacol., 106(3):539-46 (1984).
Rosenzweig-Lipson et al., 5-HT(2C) agonists as therapeutics for the treatment of schizophrenia, Handb. Exp. Pharmacol., (213):147-65 (2012).
Siuciak et al., CP-809,101, a selective 5-HT2C agonist, shows activity in animal models of antipsychotic activity, Neuropharmacology, 52(2):279-90 (2007).
Smith et al., The potential use of selective 5-HT2C agonists in treating obesity, Expert Opin. Investig. Drugs, 15(3):257-66 (2006).
Thomsen et al., Lorcaserin, a novel selective human 5-hydroxytryptamine2C agonist: in vitro and in vivo pharmacological characterization, J. Pharmacol. Exp. Ther., 325(2):577-87 (2008).
Wacker et al., Structural features for functional selectivity at serotonin receptors, Science, 340(6132):615-9 (2013).
Wilen, Strategies in optical resolutions, Tetrahedron, 33(21):2725-36 (1977).
Yamazaki et al., Computational prediction of the plasma protein-binding percent of diverse pharmaceutical compounds, J. Pharm. Sci., 93(6):1480-94 (2004).
Cheng et al., Further Advances in Optimizing (2-Phenylcyclopropyl)methylamines as Novel Serotonin 2C Agonists: Effects on Hyperlocomotion, Prepulse Inhibition, and Cognition Models, J. Med. Chem., 59(2):578-91 (Jan. 2016).
European Patent Application No. 16703034.5, Communication Pursuant to Rule 164(2)(b) and Article 9493) Epc, dated Feb. 1, 2019.

* cited by examiner

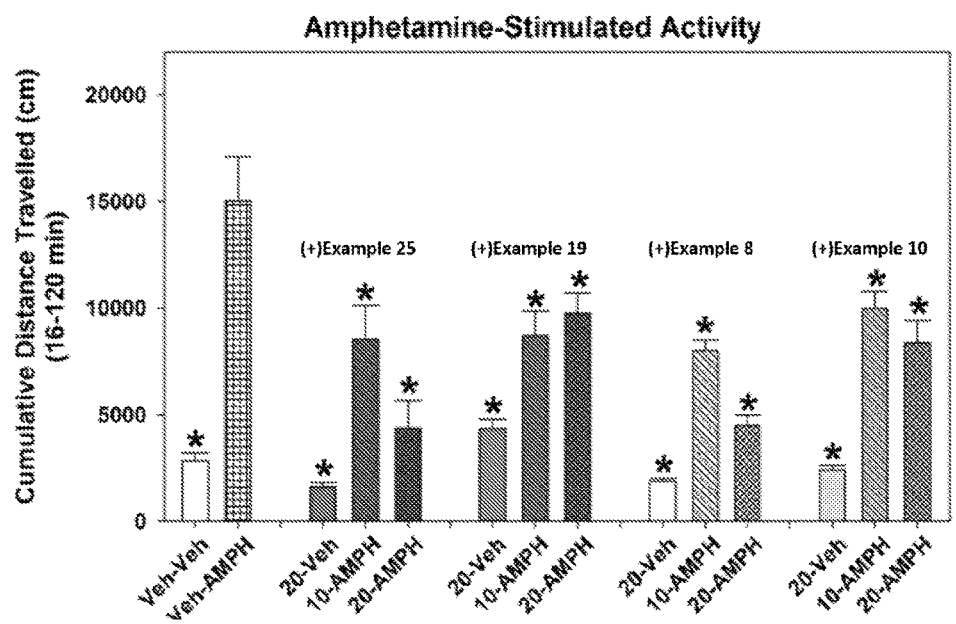

Cumulative locomotor activity following injection of the vehicle (Veh) or 3 mg/kg $d$-amphetamine (AMPH). AMPH-stimulated locomotor activity in the Veh-AMPH group was higher than that in all other groups tested. Locomotion in the Veh-Veh group was similar to that in the (+)-Example 25-Veh, (+)-Example 19-Veh, (+)-Example 8-Veh, and (+)-Example 10-Veh groups (i.e., 20-Veh groups). Both 10 and 20 mg/kg of each of the 4 compounds decreased the AMPH-stimulated hyperlocomotion, with 20 mg/kg (+)-Example 25 and (+)-Example 8 being the most efficacious. $N = 8 - 16$ mice/group; *, $p < 0.035$, from the Veh-AMPH group.

CYCLOPROPYLMETHANAMINES AS SELECTIVE 5-HT(2C) RECEPTOR AGONISTS

CROSS-REFERENCE TO RELATED APPLICATIONS

This is the U.S. national stage application of PCT/US2016/015019, filed Jan. 27, 2016, which claims the benefit of U.S. Provisional Patent Application No. 62/109,104 filed on Jan. 29, 2015.

STATEMENT OF GOVERNMENT INTEREST

This invention was made with government support under Grant No. R01 MH099993 awarded by the National Institutes of Health. The government has certain rights in this application.

FIELD OF INVENTION

The present invention relates to compounds that modulate 5-HT(2) receptors. More particularly, the present invention relates to highly selective 5-HT(2C) agonists. The compounds are used methods of treating diseases and conditions wherein modulation of 5-HT(2) receptors provide a benefit, such as obesity and psychiatric disorders.

BACKGROUND OF THE INVENTION

Serotonin or 5-hydroxytryptamine (5-HT) is a major neurotransmitter that is primarily found in the gastrointestinal tract, platelets, and the central nervous system (CNS). 5-HT is involved in the regulation of a variety of physiological functions, such as intestinal movements, mood, cognition, and appetite (1). These functions are mediated through serotonin receptors, which belong to the G-protein coupled receptor (GPCR) superfamily and are composed of seven subfamilies (5-$HT_{1-7}$) and 14 isoforms (2).

Recently, the serotonin 2C (5-$HT_{2C}$) receptor has been shown to be a promising drug target for the treatment of a variety of CNS disorders, including obesity and mental disorders, such as schizophrenia, depression, and anxiety (3). Furthermore, based on the study of both its distribution and biological function, 5-HT(2C) receptors in the basal ganglia likely are essential for the regulation of repetitive motion and in the cingulate gyrus they mediate many of the effects of neurotransmitters on obsessive/compulsive-type behaviors. Therefore, 5-HT(2C) receptor agonists can be useful for the treatment of some neurological disorders, such as Rett syndrome.

One of the many advantages of the 5-$HT_{2C}$ receptor as a CNS drug target stems from the fact that it is found almost exclusively in the CNS (4). Therefore, compounds that selectively activate this receptor should have limited impact on peripheral tissues. However, the activation of two other closely related 5-$HT_2$ subtypes, i.e., 5-$HT_{2A}$ and 5-$HT_{2B}$ receptors, has been reported to be associated with hallucinations and cardiac valvulopathy, respectively (5). Therefore, the identification of ligands possessing a high selectivity against the 5-$HT_{2A}$ and 5-$HT_{2B}$ receptors is a key criterion for the therapeutic advancement of 5-$HT_{2C}$ agonists. This goal has been challenging due to the high conservation of molecular determinants involved in ligand recognition within this subfamily of receptors (6).

Currently, a number of 5-$HT_{2C}$ agonists (Table 1) having potential therapeutic uses or as a chemical tool for the study of the biological roles of 5-$HT_{2C}$ receptor are being evaluated. Among them, lorcaserin (Belviq) was approved for the treatment of obesity. Although it was reported to have 100-fold selectivity for 5-$HT_{2C}$ relative to the 5-$HT_{2B}$ subtype, lorcaserin possesses full agonist activity at 5-$HT_{2B}$ ($EC_{50}$=943±90 nM, $E_{max}$=100%) (7). Hence, it is not surprising that lorcaserin was found to cause a higher incidence of cardiac valve disorders in clinical trials compared to the placebo group (8). Vabicaserin (SCA-136) targets 5-$HT_{2C}$ receptors ($EC_{50}$=8 nM, $E_{max}$=100%) and was tested in clinical trials for the treatment of schizophrenia (9). However, it displayed moderate efficacy on 5-$HT_{2B}$ receptors ($E_{max}$=50%) and good potency ($EC_{50}$=12 or 102 nM depending on receptor densities) (10). WAY-163909, an analogue of vabicaserin, was shown to have selectivity toward 5-$HT_{2C}$ ($EC_{50}$=8 nM; $E_{max}$=90%), while possessing no agonist activity at 5-$HT_{2A}$ and weak efficacy at 5-$HT_{2B}$ receptors ($E_{max}$=40%). WAY-163909 has a good preclinical antipsychotic-like activity in several animal models (11). Compound CP-809,101 is one of the most selective and potent 5-$HT_{2C}$ ($EC_{50}$=0.11 nM, $E_{max}$=93%) ligands developed, with about 600-fold 5-$HT_{2C}$ selectivity against 5-$HT_{2B}$. However, it is still relatively potent at 5-$HT_{2B}$ ($EC_{50}$=65.3 nM, $E_{max}$=57%) (12). Due to the genotoxicity of this compound, it could not be advanced to clinical evaluation (13). Nonetheless, CP-809,101 has structural similarities to mCPP and MK-212, two compounds discovered decades ago and used as tools for the pharmacological study of 5-$HT_{2C}$ receptors (14).

TABLE 1

Representative 5-$HT_{2C}$ agonists.

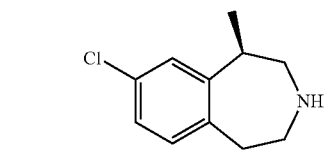

Lorcaserin

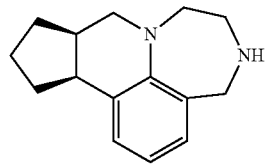

Vabicaserin

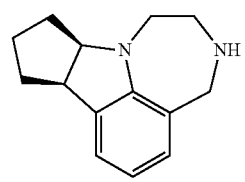

WAY-163909

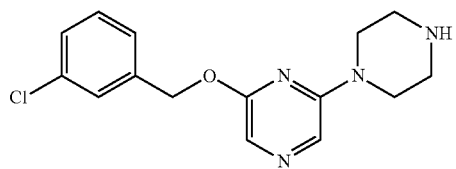

CP-809, 101

TABLE 1-continued

Representative 5-HT$_{2C}$ agonists.

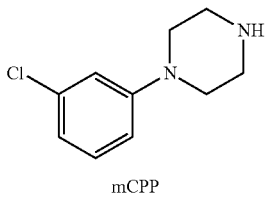 [SMILES: Clc1cccc(N2CCNCC2)c1]

mCPP

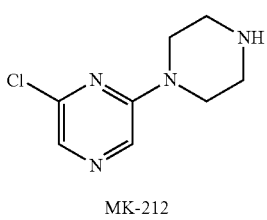 [SMILES: Clc1cncc(N2CCNCC2)n1]

MK-212

Compounds that possess the 2-phenylcyclopropylmethylamine scaffold were developed as selective 5-HT$_{2C}$ agonists. This particular scaffold was derived from an initial high throughput screening (HTS) screening campaign in which tranylcypromine was identified as a hit (15). Research led to the identification of compounds possessing a 2-cyclopropylmethoxy group at position 2, as illustrated by the compounds in Table 2. The compound, possessing a fluorine substitution at position 5 of the benzene ring, showed good potency on the 5-HT$_{2C}$ receptor (EC$_{50}$=21 nM), with only moderate selectivity for 5-HT$_{2B}$(EC$_{50}$=289 nM) (16). Replacement of the fluorine atom with a hydroxyl group led to the enhancement of both potency and selectivity, but the bioavailability was found to be too low (F=3.2% in mice, unpublished data). A compound lacking substitution at the same position showed good potency as a partial agonist (EC$_{50}$=55 nM, E$_{max}$=61%), with excellent selectivity against both 5-HT$_{2A}$ and 5-HT$_{2B}$ (17).

TABLE 2

Selective 5-HT$_{2C}$ agonists based on 2-phenylcyclopropylmethylamino scaffold.

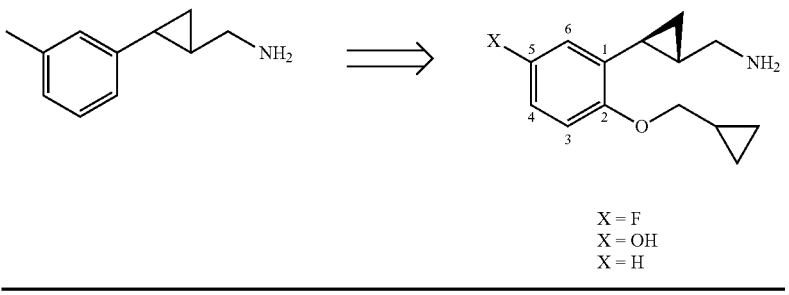

X = F
X = OH
X = H

These findings indicate that a need exists in the art for drugs that interact selectively with 5-HT(2) receptor subtypes, and, in particular, selective 5-HT(2C) receptor agonists, which exhibit minimal effect on 5-HT(2A) and 5-HT(2B) receptors. Selective 5-HT(2C) receptor agonists can be useful for treatment obesity and related or associated disorders, including hypertension, hyperlipidemia, diabetes, and cardiovascular disease, and avoid interaction with several related and unrelated receptors associated with significant morbidity and mortality, e.g., valvular heart disease associated with activation of the 5-HT(2B) receptor subtype and hallucinations associated with activation of the 5-HT(2A) receptor subtype.

Selective 5-HT(2C) receptor agonists can be useful in the treatment of depression, anxiety, panic disorder, schizophrenia, OCD, epilepsy, migraine and Rett syndrome. In addition, 5-HT(2C) receptor agonists are further disclosed in WO 2006/065600 and WO 2007/025144 as useful for treatment of Alzheimer's Disease, in prevention or treatment of senile plaques, and in the treatment of sexual dysfunction in males and females, including the treatment of erectile dysfunction.

A number of synthetic compounds have been reported that show 5-HT(2C) receptor agonistic activity, including in U.S. Pat. Nos. 6,962,939; 6,777,407; 7,012,089; 6,953,787; and 7,071,185; U.S. Patent Publication Nos. 2005/197380; 2005/020573; 2006/154290; 2005/026925; 2005/0143452; 2002/032199; and 2005/0261347; and published PCT applications WO 2000/035922; WO 2006/065600; WO 2006/077025; and WO 2005/007614, for example.

An important advance in the art would be the discovery of selective 5-HT(2C) receptor agonists that are useful in the treatment of diseases and conditions wherein 5-HT(2C) receptor agonism provides a benefit, such as psychiatric disorders, addictive behaviors, cognition disorders, obesity, movement disorders, and compound addiction, for example. A significant need exists in the art for efficacious compounds, compositions, and methods useful in the treatment of such diseases and conditions, alone or in conjunction with other therapies used to treat these diseases and conditions. The present invention is directed to meeting this need.

SUMMARY OF THE INVENTION

The present invention relates to 5-HT(2C) receptor agonists, pharmaceutical compositions comprising the 5-HT(2C) receptor agonists, and methods of treating diseases and conditions wherein agonism of 5-HT(2C) receptors provides a benefit, such as psychiatric disorders and obesity, comprising administering a therapeutically effective amount of a 5-HT(2C) receptor agonist to an individual in need thereof. The present 5-HT(2C) receptor agonists exhibit selectivity over other members of the 5-HT(2) family of receptors.

More particularly, the present invention relates to 5-HT(2C) agonists having a structural formula (I):

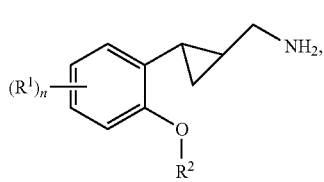

wherein $R^1$ is halo;

$R^2$ is $C_{1-5}$alkyl, fluorinated $C_{1-3}$alkyl, phenyl, benzyl,

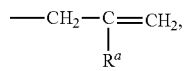

—$CH_2$—C≡CH, or —$(CH_2)_{1-3}XCH_3$;

X is O or S;

$R^a$ is hydrogen, fluoro, or $C_{1-3}$alkyl; and n is an integer 1, 2, or 3;

or a pharmaceutically acceptable salt or hydrate thereof.

The present compounds modulate receptors of the 5-HT (2) family, and particularly 5-HT(2C) receptors. In some embodiments, the present compounds selectively modulate the 5-HT(2C) receptor, while exhibiting significantly less or no activity on the 5-HT(2B) receptor. In some embodiments, the present compounds selectively modulate the 5-HT(2C) receptor, while exhibiting significantly less or no activity on the 5-HT(2A) receptor. In preferred embodiments, compounds of this invention are selective agonists for the 5-HT(2C) receptor, while exhibiting significantly less or no activity on the 5-HT(2A) receptor and/or the 5-HT(2B) receptor.

In another embodiment, the present invention provides a method of treating a condition or disease by administering a therapeutically effective amount of a 5-HT(2C) receptor agonist of structural formula (I) to an individual in need thereof. The disease or condition of interest is treatable by modulating the activity of 5-HT(2C) receptors, for example, psychiatric disorders, addictive behaviors, cognitive disorders, obesity, movement disorders, and compound addictions.

Another embodiment of the present invention provides a method of treating a disease or condition by modulating 5-HT(2C) receptor activity comprising administering to an individual in need thereof, such as a human, a therapeutically effective amount of a compound of structural formula (I). The compound of structural formula (I) can be administered as the sole therapy, or in conjunction with a therapeutically effective amount of a second therapeutic agent useful in a treatment of the disease or condition.

In another embodiment, the present invention provides a pharmaceutical composition comprising a compound of structural formula (I) and a pharmaceutically acceptable excipient.

Another embodiment of the present invention is to utilize a compound of structural formula (I) and an optional second therapeutically active agent in a method of treating an individual for a disease or condition wherein modulation of 5-HT(2C) receptor activity provides a benefit.

In a further embodiment, the invention provides for use of a composition comprising a compound of structural formula (I) and an optional second therapeutic agent for the manufacture of a medicament for treating a disease or condition of interest, e.g., a psychiatric disorder.

Still another embodiment of the present invention is to provide a kit for human pharmaceutical use comprising (a) a container, (b1) a packaged composition comprising a compound of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

The compound of structural formula (I) and the second therapeutic agent can be administered together as a single-unit dose or separately as multi-unit doses, wherein the compound of structural formula (I) is administered before the second therapeutic agent, or vice versa. It is envisioned that one or more dose of a compound of structural formula (I) and/or one or more dose of a second therapeutic agent can be administered.

In one embodiment, a compound of structural formula (I) and a second therapeutic agent are administered simultaneously. In related embodiments, a compound of structural formula (I) and a second therapeutic agent are administered from a single composition or from separate compositions. In a further embodiment, a compound of structural formula (I) and a second therapeutic agent are administered sequentially. A compound of structural formula (I) can be administered in an amount of about 0.005 to about 500 milligrams per dose, about 0.05 to about 250 milligrams per dose, or about 0.5 to about 100 milligrams per dose.

An additional embodiment of the present invention is a method for modulating a 5-HT(2C) receptor in vivo or in vitro comprising contacting the receptor with one or more compound of structural formula (I). In specific embodiments, the method stimulates or activates the 5-HT(2C) receptor. In specific embodiments, the compounds of structural formula (I) are 5-HT(2C) receptor agonists or selective agonists.

These and other novel aspects of the present invention will become apparent from the following detailed description of the preferred embodiments.

BRIEF DESCRIPTION OF THE FIGURES

FIG. 1 contains plots for cumulative distance travelled in an amphetamine-stimulated activity test using compounds (+)-Example 25, (+)-Example 19, (+)-Example 8, and (+)-Example 10

DETAILED DESCRIPTION OF THE PREFERRED EMBODIMENTS

The present invention is directed to novel modulators of 5-HT(2C) activity and their use in therapeutic treatments of, for example, psychiatric disorders, obesity, cognitive disorders, addiction, movement disorders, and compound addiction. In some embodiments, the present compounds selectively modulate 5-HT(2C) receptors over other 5-HT(2) receptors.

The present invention is described in connection with preferred embodiments. However, it should be appreciated that the invention is not limited to the disclosed embodiments. It is understood that, given the description of the embodiments of the invention herein, various modifications can be made by a person skilled in the art.

The term "a disease or condition wherein modulation of 5-HT(2C) receptors provides a benefit" pertains to a condition in which 5-HT(2C) receptors and/or the action of 5-HT(2C) receptors is important or necessary, e.g., for the onset, progress, expression of that disease or condition, or a disease or a condition which is known to be treated by a modulation of 5-HT(2C) receptors. Examples of such conditions include, but are not limited to, schizoaffective disorders, anxiety, panic disorders, adjustment disorders, schizophrenia, clinical depression, bipolar disorder, addictive behaviors, compound addiction (e.g., cocaine, metamphetamine, and amphetamine), adjustment disorders, obsessive compulsive disorder, movement disorders (e.g., Huntington's disease, Parkinson's disease, and dyskinesia), cognition disorders (e.g., Alzheimer's disease and mild cognitive impairment), metabolic disorders (e.g., dyslipidemia, Type 2 diabetes, metabolic syndrome, and obesity), chronic pain, dystonia, and eating disorders. One of ordinary skill in the art is readily available to determine whether a compound treats a disease or condition mediated by 5-HT (2C) receptors for any particular cell type, for example, by assays which conveniently can be used to assess the activity of particular compounds.

The term "second therapeutic agent" refers to a therapeutic agent different from a compound of structural formula (I) and that is known to treat the disease or condition of interest. For example when obesity is the disease or condition of interest, the second therapeutic agent can be a known anti-obesity drug.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual in need thereof.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a compound of structural formula (I) can be administered at the same time or sequentially in any order at different points in time as a second therapeutic agent. A present compound and the second therapeutic agent can be administered separately, in any appropriate form and by any suitable route. When a present compound and the second therapeutic agent are not administered concurrently, it is understood that they can be administered in any order to a subject in need thereof. For example, a present compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment, to an individual in need thereof. In various embodiments, a compound of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The term "agonist" refers generally to a compound that interacts with and activates a receptor, such as one or more of the receptors of the 5-HT2 family of receptors, and initiates a physiological or pharmacological response characteristic of that receptor.

The term "antagonist" refers generally to a compound that binds to the receptor at the same site as an agonist, but which does not activate the intracellular response initiated by the active form of the receptor, and as such an antagonist can inhibit the intracellular responses by agonists.

As used herein the term "selective 5-HT(2C) receptor agonist" means an agonist compound that is selective for binding and activation of 5-HT(2C) receptors compared to the other receptors of the 5-HT2 family of receptors. An agonist of this invention can be selective for the 5-HT(2C) receptor over the 5-HT(2B) receptor, be selective for the 5-HT(2C) receptor over the 5-HT(2A) receptor, or be selective for the 5-HT(2C) receptor over both the 5-HT(2B) and 5-HT(2A) receptors. In some embodiments, a present 5-HT (2C) receptor agonist can exhibit agonist activity with respect to the 5-HT(2A) receptor. A selective 5-HT(2C) receptor agonist can exhibit a 5-fold, 10-fold, 20-fold, 30-fold, 40-fold, 50-fold, 60-fold, 70-fold, 80-fold, 90-fold, 100-fold, or 200-fold or more higher activity for the 5-HT (2C) receptor compared to either or both of the 5-HT(2B) or 5-HT(2A) receptors.

Selectivity can be assessed, for example, by determining EC$_{50}$ ratios for different receptors. Any method known in the art to be reliable and accurate for measuring receptor agonist activity can be used to assess selectivity of a given agonist. As understood by one skilled in the art, selectivity can be determined, for example, using a receptor binding assay or a functional assay. In specific embodiments, methods described in the examples herein or in methods detailed in references cited herein can be employed. In specific embodiments herein, 5-HT(2C) receptor agonists of this invention can also exhibit selectively over receptors of 5-HT families other than those of the 5-HT2 family. In specific embodiments herein, 5-HT(2C) receptor agonists of this invention may exhibit antagonist activity for 5-HT(2B) receptors.

In some embodiments, a present 5-HT(2C) receptor agonist exhibits an EC$_{50}$ value for activation of human 5-HT (2C) receptors of 100 nM or less. In preferred embodiments, the 5-HT(2C) receptor agonists exhibit EC$_{50}$ values for activation of human 5-HT(2C) receptors of 25 nM or less. In more preferred embodiments, 5-HT(2C) receptor agonists exhibit EC$_{50}$ values for activation of human 5-HT(2C) receptors of 10 nM or less. In some embodiments, compounds of the present invention exhibit 5-fold or more selectivity as agonists for 5-HT(2C) receptors compared to 5-HT(2B) receptors or 5-HT(2A) receptors as assessed by determination of EC$_{50}$ ratios. In some embodiments, compounds of present invention exhibit 10-fold or more selectivity as agonists for 5-HT(2C) receptors compared to 5-HT(2B) receptors or 5-HT(2A) receptors, as assessed by determination of EC$_{50}$ ratios. In preferred embodiments, the present compounds exhibit 100-fold or more selectivity as agonists for 5-HT(2C) receptors compared to 5-HT(2B) receptors or 5-HT(2A) receptors, as assessed by determination of EC$_{50}$ ratios.

The use of the terms "a", "an", "the", and similar referents in the context of describing the invention (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the invention and is not a limitation on the scope of the invention unless otherwise claimed. No language in the specification should be construed as indicating any non-claimed element as essential to the practice of the invention.

Selective 5-HT(2C) receptor agonists are known. For example. the following compound is a potent, moderately selective 5-HT(2C) agonist having a 120- and 14-fold selectivity over 5-HT(2A) and 5-HT(2B), respectively (EC$_{50}$=585, 65, and 4.8 nM at the 2A, 2B, and 2C subtypes, respectively). The compound (10-60 mg/kg) also demonstrated moderate antidepressant-like effects in a commonly used behavioral assay.

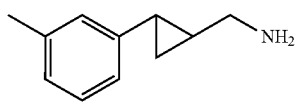

However, this compound does not exhibit sufficient selectivity over the 5-HT(2B) receptor to qualify as a potential clinical candidate. In particular, the degree of selectivity was considered too low to avoid side effects attributed to 5-HT (2B) activity. Accordingly, new drug candidates with an increased subtype selectivity were sought.

The present invention is directed to 5-HT(2C) receptor agonists of structural formula (I), compositions comprising a compound of structural formula (I), and therapeutic uses of compounds of structural formula (I):

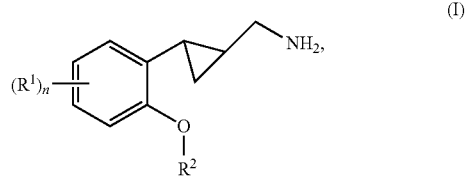

wherein R$^1$ is halo;
R is C$_{1-5}$alkyl, fluorinated C$_{1-3}$alkyl, phenyl, benzyl,

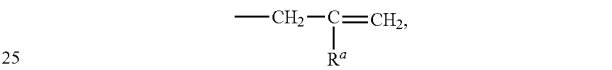

—CH$_2$—C≡CH, or —(CH$_2$)$_{1-3}$XCH$_3$;
X is O or S;
R$^a$ is hydrogen, fluoro, or C$_{1-3}$alkyl; and
n is an integer 1, 2, or 3;
or a pharmaceutically acceptable salt or hydrate thereof.

In some preferred embodiments, R$^1$ is fluoro or chloro. In other embodiments, n is 1 and R$^1$ is fluoro or chloro. In other embodiments, n is 2, and R$^1$ is fluoro and fluro, chloro and chloro, or fluoro and chloro.

In other preferred embodiments, R$^2$ is methyl, ethyl, n-propyl, isopropyl, n-butyl, isobutyl, n-pentyl, or isopentyl. In other preferred embodiments, R$^2$ is phenyl or benzyl. In still other embodiments, R$^2$ is
—CH$_2$CH$_2$F, —CH$_2$CH$_2$CH$_2$F, —CH$_2$CHF$_2$, or —CH$_2$CF$_3$.

In another embodiment, R$^2$ is

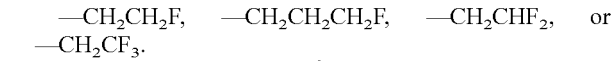

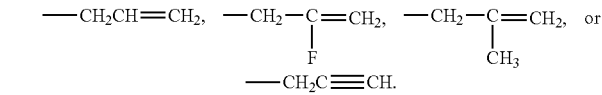

In yet another embodiment, R$^2$ is
—CH$_2$CH$_2$—O—CH$_3$ or —CH$_2$CH$_2$—S—CH$_3$.

The compounds of structural formula (I) modulate 5-HT (2C) receptors and are useful in the treatment of a variety of diseases and conditions. In particular, compounds of structural formula (I) are used in methods of treating a disease or condition wherein activity of 5-HT(2C) receptors provides a benefit, for example, psychiatric conditions and obesity. The methods comprise administering a therapeutically effective amount of a compound of structural formula (I) to an individual in need thereof.

The present methods also encompass administering a second therapeutic agent to the individual in addition to a compound of structural formula (I). The second therapeutic agent is selected from agents, such as drugs and adjuvants, known as useful in treating the disease or condition afflicting the individual, e.g., a therapeutic agent known as useful in treating a particular psychiatric disorder.

As used herein, the term "alkyl" refers to straight chained and branched saturated hydrocarbon groups, nonlimiting examples of which include methyl, ethyl, and straight chain and branched propyl, butyl and pentyl groups containing the indicated number of carbon atoms. The term $C_n$ means the alkyl group has "n" carbon atoms.

The term "halo" is defined as fluoro, chloro, bromo, and iodo.

Additionally, salts of the present 5-HT(2C) receptor agonists also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the present 5-HT(2C) receptor agonists often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or prodrugs thereof.

The compounds of structural formula (I) may contain one or more asymmetric carbon atoms, such that the compounds can exist in different stereoisomeric forms. The compounds can be, for example, racemates or optically active forms. The present invention therefore encompasses racemic forms of the compounds of structural formula (I), as well as the individual enantiomers and non-racemic mixtures thereof. The optically active forms can be obtained by resolution of the racemates or by asymmetric synthesis. In some preferred embodiments of the invention, enantiomers of the invention exhibit specific rotation [α] that is + (positive). Preferably, the (+) enantiomers are substantially free of the corresponding (−) enantiomer. Thus, an enantiomer substantially free of the corresponding enantiomer refers to a compound which is isolated or separated via separation techniques or is prepared free of the corresponding enantiomer. "Substantially free" means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., "Enantiomers, Racemates and Resolutions" (Wiley Interscience, New York, 1981); Wilen, S. H., et al., *Tetrahedron* 33:2725 (1977); Eliel, E. L. "Stereochemistry of Carbon Compounds" (McGraw-Hill, N.Y., 1962); Wilen, S. H. "Tables of Resolving Agents and Optical Resolutions" p. 268 (E. L. Eliel, Ed., Univ. of Notre Dame Press, Notre Dame, Ind. 1972).

It is hypothesized, but not relied upon, that the alkoxyl substituents at position 2 on the benzene ring can be accommodated within a hydrophobic cavity, which could vary in size among the $5-HT_{2C}$, $5-HT_{2A}$, and $5-HT_{2B}$ receptors. This cavity can be slightly larger for the $5-HT_{2C}$ receptors compared to the $5-HT_{2A}$ and $5-HT_{2B}$ receptors because (a) small groups attached to position 2 displayed good activity at all three subtypes (less selectivity) and (b) increasing the size of the substituent resulted in a decrease in activity at $5-HT_{2A}$ and $5-HT_{2B}$, while retaining good activity at $5-HT_{2C}$. Accordingly, by achieving a proper balance of size and lipophilicity, more potent $5-HT_{2C}$ agonists with improved selectivity against the $5-HT_{2A}$ and $5-HT_{2B}$ subtypes have been discovered.

Synthetic Methods

Compounds of the present invention are prepared employing methods as described herein or are prepared by routine modification or adaptation of the methods herein, for example, by selection of starting materials, or variation of reagents, solvents, and/or purification methods, in view of knowledge in the art.

All compounds could be prepared with reported intermediates or through the following general scheme, starting from 2-methoxyl benzaldehydes with proper substitutions on the benzene ring. The aldehydes (A) were treated with N-methoxy-N-methyl-2-(triphenylphosphoranylidene)acetamide to give the (E)-N-methoxy-3-(2-methoxyphenyl)-N-methylacrylamides (B), which would provide the cyclopropane (C) in trans conformation under Corey-Chaykovsky cyclopropanation condition. The Weinreb amides (C) were then reduced with DIBA1-H to give the corresponding aldehydes (D) and then the alcohols (E) with NaBH$_4$ reduction. The alcohols (E) were then converted to Gabriel imides (F) under Mitsunobu conditions, which could be de-protected with hydrazine to give primary amines (G). The methoxyl ethers (G) were converted to phenols (H) with borane tribromide (BBr$_3$), and the amino groups were protected as Boc intermediates. Williamson ether synthesis or Mitsunobu conditions with the phenols provided the Boc intermediates (J), which were then de-protected to give compounds (I).

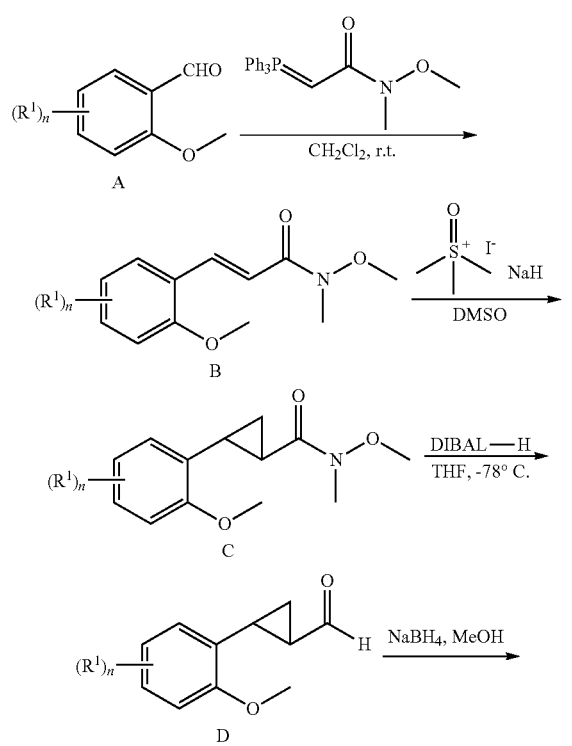

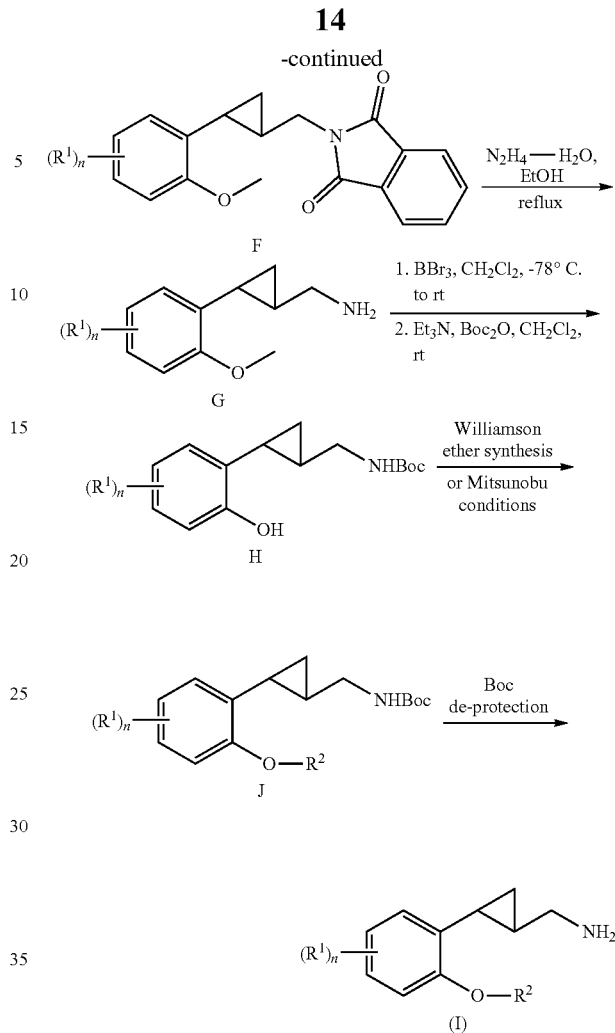

The N-Boc-amines were separated with chiral HPLC, and subsequent Boc de-protection provides both (−) and (+) enantiomers in optical pure forms.

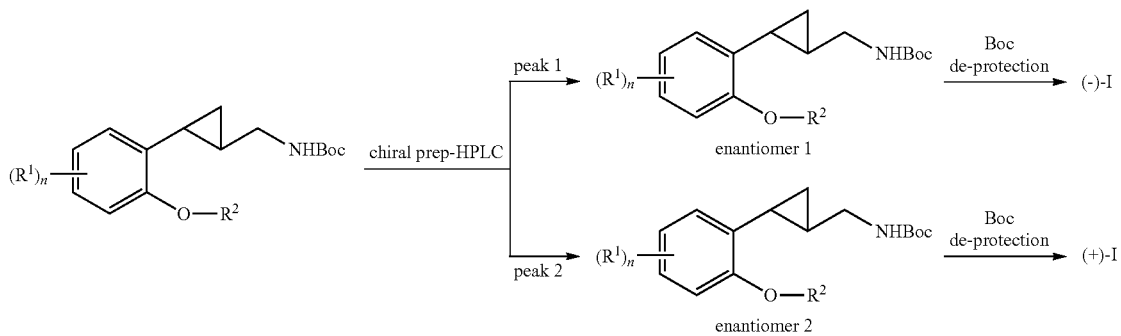

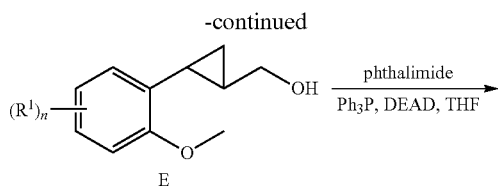

Synthetic Procedures and Compounds Characterization Data
General.

All chemicals and solvents were purchased from Sigma-Aldrich or Fisher Scientific, and used without further purification. Microwave reactions were run in Biotage Initiator Microwave Synthesizer. Synthetic intermediates were purified by CombiFlash flash chromatography on 230-400 mesh silica gel. $^1$H and $^{13}$C NMR spectra were recorded on Bruker DPX-400 or AVANCE-400 spectrometer, at 400 MHz and 100 MHz respectively. NMR chemical shifts were reported in δ (ppm) using residual solvent peaks as standard (CDCl$_3$: 7.26 ppm ($^1$H), 77.23 ppm (13C); CD$_3$OD: 3.31 ppm ($^1$H), 49.15 ppm ($^{13}$C); DMSO-d$_6$: 2.50 ppm (H), 39.52 ppm ($^{13}$C)). Mass spectra were measured in the ESI mode at an ionization potential of 70 eV with an LC-MS MSD (Hewlett-Packard). Purity of all final compounds (greater than 95%) was determined by analytical HPLC (ACE 3AQ C$_{18}$ column (150×4.6 mm, particle size 3 μM), 0.05% TFA in H$_2$O/0.05% TFA in MeOH gradient eluting system). Optical rotation values were recorded on Autopol IV automatic polarimeter.

Example 1

(−)-(2-(5-Chloro-4-fluoro-2-methoxyphenyl)cyclopropyl)methanamine (HCl Salt)

(+)-(2-(5-Chloro-4-fluoro-2-methoxyphenyl)cyclopropyl)methanamine (HCl Salt)

Route 1:

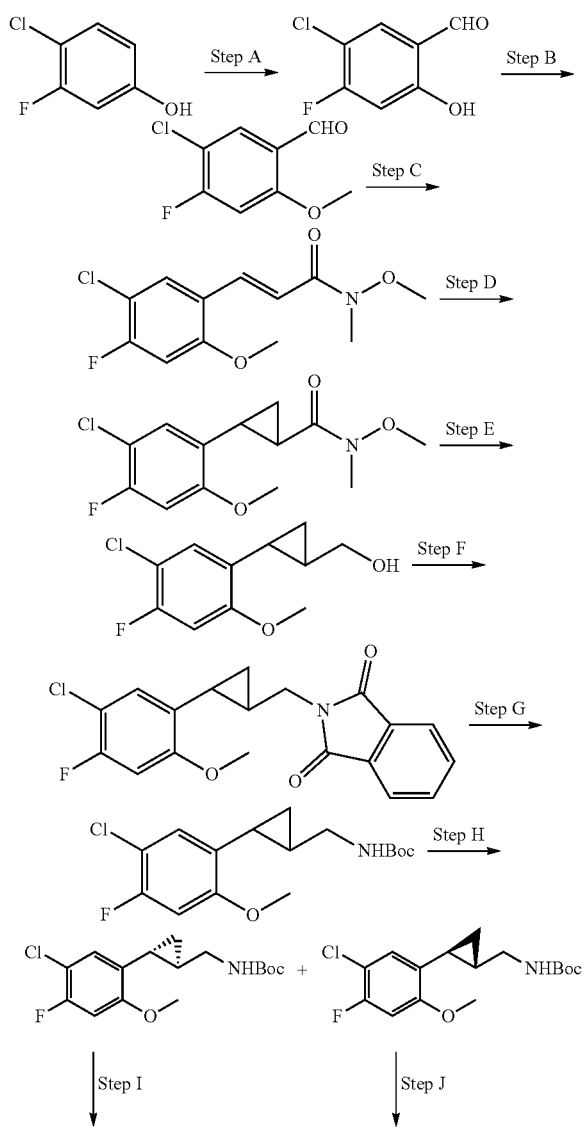

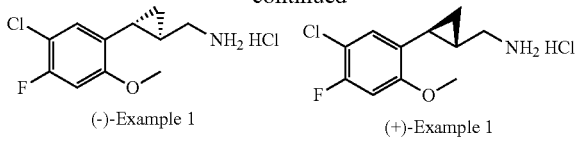

Step A: 5-Chloro-4-fluoro-2-hydroxybenzaldehyde

3-Fluoro-4-chlorophenol (14.8 g, 100 mmol) was dissolved in TFA (100 mL), and hexamethylene-tetramine (16.8 g, 120 mmol) was added in small portions. The mixture was then refluxed overnight. After cooling to room temperature, conc. H$_2$SO$_4$ (4 mL) and H$_2$O (100 mL) was added and stirred for 10 min. The mixture was then extracted with CH$_2$Cl$_2$ (3×100 mL), and the combined organic layers were washed with brine, dried over Na$_2$SO$_4$, concentrated and purified with flash chromatography (0-30% EA in hexane) to give the subtitle compound as light yellow solid (5.8 g, 33%). $^1$H NMR (CDCl$_3$, 400 MHz) 11.22 (s, 1H), 9.80 (s, 1H), 7.61 (d, J=8.0 Hz, 1H), 6.80 (d, J=8.0 Hz, 1H).

Step B: 5-Chloro-4-fluoro-2-methoxybenzaldehyde

To a solution of 5-chloro-4-fluoro-2-hydroxybenzaldehyde (5.7 g, 33 mmol) in DMF (50 mL) was added K$_2$CO$_3$ (9.1 g, 66 mmol) and MeI (9.4 g, 66 mmol), and the mixture was stirred at room temperature for 3 h. Water was added, and the mixture was extracted with ethyl acetate. The combine extracts were washed with brine, dried over Na$_2$SO$_4$, concentrated and purified with flash chromatography to give a white solid (5.2 g, 84%). $^1$H NMR (CDCl$_3$, 400 MHz) 10.33 (s, 1H), 7.89 (d, J=8.0 Hz, 1H), 6.81 (d, J=12.0 Hz, 1H), 3.94 (s, 3H).

Step C: (E)-3-(5-chloro-4-fluoro-2-methoxyphenyl)-N-methoxy-N-methylacrylamide

To a solution of 5-chloro-4-fluoro-2-methoxybenzaldehyde (4.1 g, 22 mmol) in CH$_2$Cl$_2$ (100 mL) was added N-methoxy-N-methyl(triphenyl-phosphoranylidene)acetamide (9.5 g, 26 mmol) and the solution was stirred at room temperature overnight. Solvent was removed and the solid was purified with flash chromatography to give a white solid (6.2 g, 84%). $^1$H NMR (CDCl$_3$, 400 MHz) 7.90 (d, J=16.0 Hz, 1H), 7.57 (d, J=8.4 Hz, 1H), 7.00 (d, J=16.0 Hz, 1H), 6.72 (d, J=10.8 Hz, 1H), 3.87 (s, 3H), 3.81 (s, 3H), 3.32 (s, 3H).

Step D: 2-(5-chloro-4-fluoro-2-methoxyphenyl)-N-methoxy-N-methylcyclopropanecarboxamide To a suspension of trimethylsulfoxonium iodide (8.8 g, 40 mmol) in anhydrous DMSO (50 mL) under argon was added NaH (60% in mineral oil, 1.6 g, 40 mmol) in small portions. The mixture was stirred at room temperature for 1 h before a solution of (E)-3-(5-chloro-4-fluoro-2-methoxyphenyl)-N-methoxy-N-methylacrylamide (5.5 g, 20 mmol) in anhydrous DMSO (50 mL) was added slowly. The resulting clear solution was stirred at room temperature overnight. Water was added and the mixture was extracted with ethyl acetate, the combines extracts were washed with brine, dried over Na$_2$SO$_4$, concentrated and purified with flash chromatography to give a white solid (4.9 g, 85%). $^1$H NMR (CDCl$_3$, 400 MHz) 6.92 (d, J=8.0 Hz, 1H), 6.65 (d, J=10.8 Hz, 1H), 3.80

(s, 3H), 3.71 (s, 3H), 3.24 (s, 3H), 2.63-2.58 (m, 1H), 2.29-2.24 (m, 1H), 1.59-1.54 (m, 1H), 1.27-1.21 (m, 1H).

Step E: (2-(5-chloro-4-fluoro-2-methoxyphenyl) cyclopropyl)methanol

A solution of 2-(5-chloro-4-fluoro-2-methoxyphenyl)-N-methoxy-N-methylcyclopropanecarboxamide (5.0 g, 17.4 mmol) in anhydrous THF (80 mL) was cooled to −78° C. under argon. To this solution was added DIBAL-H (1.0 M in cyclohexane, 26.1 mL, 26.1 mmol), and the solution was stirred at the same temperature for 2 h. Saturated aqueous Rochelle's salt solution (100 mL) was added and the mixture was warmed to room temperature and extracted with ethyl acetate. The combined extracts were dried over $Na_2SO_4$, filtered and concentrated to give a colorless oil. The oil was then dissolved in MeOH (100 mL), and $NaBH_4$ (1.2 g, 31.6 mmol) was added in small portions. After stirring at room temperature for 30 mins, 1N HCl (30 mL) was added and the mixture was concentrated and extracted with $CH_2Cl_2$. The combined extracts were washed with brine, dried over $Na_2SO_4$, concentrated and purified with flash chromatography to give a colorless oil (3.7 g, 92%). $^1$H NMR ($CDCl_3$, 400 MHz) 6.93 (d, J=8.4 Hz, 1H), 6.66 (d, J=10.8 Hz, 1H), 3.86-3.82 (m, 4H), 3.31 (dd, J=11.2, 8.4 Hz, 1H), 1.88 (br, 1H), 1.84-1.79 (m, 1H), 1.20-1.16 (m, 1H), 1.03-0.98 (m, 1H), 0.90-0.85 (m, 1H).

Step F: 2-((2-(5-chloro-4-fluoro-2-methoxyphenyl) cyclopropyl)methyl)isoindoline-1,3-dione A solution of (2-(5-chloro-4-fluoro-2-methoxyphenyl)cyclopropyl)methanol (3.40 g, 14.7 mmol), triphenylphosphine (5.03 g, 19.2 mmol) and phthalimide (3.25 g, 22.1 mmol) in anhydrous THF (100 mL) was cooled with ice bath, and DEAD (3.34 g, 19.2 mmol) was added slowly. The solution was then warmed to room temperature and stirred overnight. The solution was concentrated to give the crude product, which was purified with flash chromatography (0-20% ethyl acetate in hexanes) to give a white solid (5.0 g, 94%). $^1$H NMR ($CDCl_3$, 400 MHz) 7.89-7.86 (m, 2H), 7.75-7.72 (m, 2H), 6.84 (d, J=8.4 Hz, 1H), 6.52 (d, J=11.2 Hz, 1H), 3.79 (dd, J=14.0, 6.8 Hz, 1H), 3.63 (dd, J=14.0, 8.0 Hz, 1H), 3.49 (s, 3H), 2.08-2.03 (m, 1H), 1.40-1.35 (m, 1H), 1.02-0.93 (m, 2H).

Step G: Tert-butyl ((2-(5-chloro-4-fluoro-2-methoxyphenyl)cyclopropyl)methyl)carbamate To a solution of 2-((2-(5-chloro-4-fluoro-2-methoxyphenyl)cyclopropyl)methyl)isoindoline-1,3-dione (5.0 g, 13.9 mmol) in EtOH (80 mL) was added hydrazine hydrate ($N_2H_4$·1.5$H_2O$, 2.5 g, 41.7 mmol) and the mixture was refluxed for 3 h. Solvent was removed under vacuum after cooling to room temperature to give a white solid, which was dissolved in 1 N NaOH (100 mL) and extracted with $CH_2Cl_2$. The combined extracts were washed with brine, dried over $Na_2SO_4$ and filtered. $Et_3N$ (3.9 mL, 27.8 mmol) and $Boc_2O$ (4.6 g, 20.8 mmol) was then added and the solution was stirred at room temperature for 30 min. Concentration and purification with flash chromatography afforded the title compound as white solid (3.9 g, 85%). $^1$H NMR ($CDCl_3$, 400 MHz) 6.91 (d, J=8.4 Hz, 1H), 6.64 (d, J=10.8 Hz, 1H), 5.19 (br, 1H), 3.87 (s, 3H), 3.54-3.50 (m, 1H), 2.74-2.69 (m, 1H), 1.74-1.69 (m, 1H), 1.45 (s, 9H), 1.01-0.95 (m, 2H), 0.83-0.80 (m, 1H); $^{13}$C NMR ($CDCl_3$, 100 MHz) δ 158.0 (d, $J_{CF}$=8.2 Hz), 157.0 (d, $J_{CF}$=244.7 Hz), 155.9, 128.2, 127.3 (d, $J_{CF}$=3.4 Hz), 111.3 (d, $J_{CF}$=17.6 Hz), 99.8 (d, $J_{CF}$=25.0 Hz), 79.1, 55.9, 45.1, 28.6, 21.1, 16.4, 11.1.

Step H

The racemic form of tert-butyl ((2-(5-chloro-4-fluoro-2-methoxyphenyl)cyclopropyl)methyl)carbamate (500 mg) was then separated with chiral HPLC (RegisPack chiral column (25 cm×21.1 mm, 10 μM), eluting system: 4.75% EtOH in n-hexane (isotatic), flow rate: 18 mL/min.) (+)-Tert-butyl ((2-(5-chloro-4-fluoro-2-methoxyphenyl)cyclopropyl)methyl)carbamate (170 mg, 100% ee) was isolated as the first peaks and (−)-tert-butyl ((2-(5-chloro-4-fluoro-2-methoxyphenyl)cyclopropyl)methyl)carbamate (165 mg, 98% ee) as the second.

Step I: (−)-(2-(5-Chloro-4-fluoro-2-methoxyphenyl) cyclopropyl)methanamine (HCl Salt)

(+)-Tert-butyl ((2-(5-chloro-4-fluoro-2-methoxyphenyl)cyclopropyl)methyl)carbamate (140 mg, 0.42 mmol) was dissolved in 2M HCl (g) in $Et_2O$ (10 mL) and stirred at room temperature for 48 h. The white solid was collected by filtration and dried over vacuum to give the subtitle compound (85 mg, 75%). $^1$H NMR (400 MHz, $CD_3OD$) δ 7.06 (d, J=8.4 Hz, 1H), 6.91 (d, J=11.2 Hz, 1H), 3.89 (s, 3H), 3.08 (dd, J=13.2, 7.2 Hz, 1H), 2.93 (dd, J=13.2, 8.0 Hz, 1H), 2.06-2.00 (m, 1H), 1.29-1.21 (m, 1H), 1.13-1.08 (m, 1H), 1.04-0.98 (m, 1H); $^{13}$C NMR (100 MHz, $CD_3OD$) δ 159.8, 158.6 (d, $J_{CF}$=235.0 Hz), 129.2, 128.0, 112.0 (d, $J_{CF}$=17.9 Hz), 101.2 (d, $J_{CF}$=25.4 Hz), 56.8, 45.1, 19.3, 17.7, 12.9; $[\alpha]_D^{20}$ −37.4 (c 0.5, MeOH).

Step J: (+)-(2-(5-Chloro-4-fluoro-2-methoxyphenyl) cyclopropyl)methanamine (HCl Salt)

(−)-Tert-butyl ((2-(5-chloro-4-fluoro-2-methoxyphenyl)cyclopropyl)methyl)carbamate (135 mg, 0.41 mmol) was dissolved in 2M HCl (g) in $Et_2O$ (10 mL) and stirred at room temperature for 48 h. The white solid was collected by filtration and dried over vacuum to give the subtitle compound (70 mg, 64%). $^1$H NMR (400 MHz, $CD_3OD$) δ 7.06 (d, J=8.4 Hz, 1H), 6.91 (d, J=11.2 Hz, 1H), 3.89 (s, 3H), 3.08 (dd, J=13.2, 7.2 Hz, 1H), 2.92 (dd, J=13.2, 8.0 Hz, 1H), 2.06-2.00 (m, 1H), 1.28-1.21 (m, 1H), 1.14-1.08 (m, 1H), 1.04-0.98 (m, 1H); $^{13}$C NMR (100 MHz, $CD_3OD$) δ 159.8, 158.6 (d, $J_{CF}$=234.8 Hz), 129.2, 128.0, 112.1 (d, $J_{CF}$=17.8 Hz), 101.2 (d, $J_{CF}$=25.7 Hz), 56.8, 45.1, 19.3, 17.7, 12.9; $[\alpha]_D^{20}$ +35.6 (c 0.5, MeOH).

Example 2

(−)-(2-(5-Chloro-2-ethoxy-4-fluorophenyl)cyclopropyl)methanamine (HCl Salt)

(+)-(2-(5-Chloro-2-ethoxy-4-fluorophenyl)cyclopropyl)methanamine (HCl Salt)

Route 2:

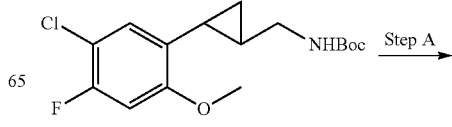

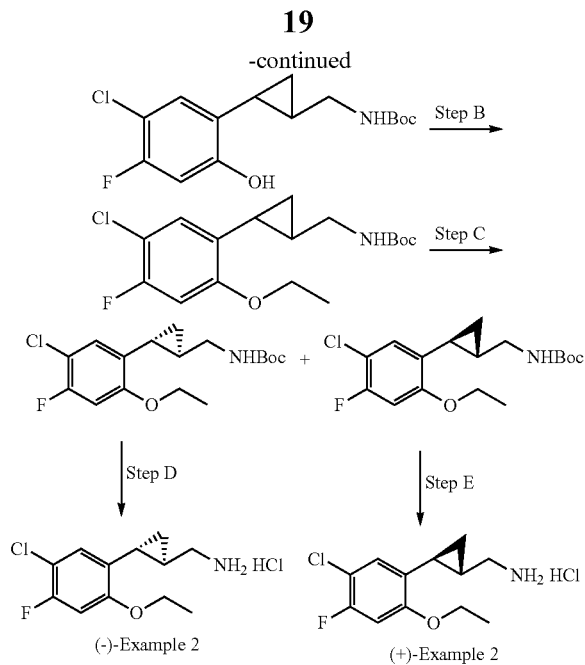

(-)-Example 2

(+)-Example 2

Step B: Tert-butyl ((2-(5-chloro-2-ethoxy-4-fluorophenyl)cyclopropyl)methyl)carbamate To a solution of tert-butyl ((2-(5-chloro-4-fluoro-2-hydroxyphenyl)cyclopropyl)methyl)carbamate (170 mg, 0.53 mmol) in anhydrous DMF (2 mL) was added $K_2CO_3$ (148 mg, 1.07 mmol) and EtI (168 mg, 1.07 mmol) and the mixture was heat at 80° C. in a microwave reactor for 1 h. Water was added and the mixture was extracted with ethyl acetate, the combined extracts were dried over $Na_2SO_4$, concentrated and purified with flash chromatography to give the subtitle compound as colorless oil (150 mg, 82%). $^1H$ NMR ($CDCl_3$, 400 MHz) 6.91 (d, J=8.0 Hz, 1H), 6.64 (d, J=10.8 Hz, 1H), 5.09 (br, 1H), 4.06 (q, J=7.2 Hz, 2H), 3.59-3.56 (m, 1H), 2.73-2.68 (m, 1H), 1.75-1.72 (m, 1H), 1.52 (t, J=6.4 Hz, 3H), 1.45 (s, 9H), 1.01-0.97 (m, 2H), 0.81-0.77 (m, 1H).

Step C

The racemic form of Tert-butyl ((2-(5-chloro-2-ethoxy-4-fluorophenyl)cyclopropyl)methyl)carbamate (150 mg) was then separated with chiral HPLC (RegisPack chiral column (25 cm×21.1 mm, 10 μM), eluting system: 4.75% EtOH in n-hexane (isotatic), flow rate: 18 mL/min.) (+)-Tert-butyl ((2-(5-chloro-2-ethoxy-4-fluorophenyl)cyclopropyl)methyl)carbamate (50 mg, 100% ee) was isolated as the first peaks and (−)-tert-butyl ((2-(5-chloro-2-ethoxy-4-fluorophenyl)cyclopropyl)methyl)carbamate (50 mg, 90% ee) as the second.

Step D: (−)-(2-(5-Chloro-2-ethoxy-4-fluorophenyl)cyclopropyl)methanamine (HCl Salt)

The subtitle compound was prepared from (+)-tert-butyl ((2-(5-chloro-2-ethoxy-4-fluorophenyl)-cyclopropyl)methyl)carbamate with 2M HCl (g) in ether as described in Example 1. $^1H$ NMR (400 MHz, $CD_3OD$) δ 7.05 (d, J=8.4 Hz, 1H), 6.89 (d, J=11.2 Hz, 1H), 4.09 (q, J=7.2 Hz, 2H), 3.06 (dd, J=13.2, 7.2 Hz, 1H), 2.97 (dd, J=13.2, 8.0 Hz, 1H), 2.07-2.04 (m, 1H), 1.46 (t, J=7.2 Hz, 3H), 1.31-1.27 (m, 1H), 1.11-1.07 (m, 1H), 1.04-1.00 (m, 1H); $^{13}C$ NMR (100 MHz, $CD_3OD$) δ 159.0, 158.5 (d, $J_{CF}$=243.8 Hz), 129.1, 128.1, 112.0 (d, $J_{CF}$=17.9 Hz), 101.9 (d, $J_{CF}$=25.6 Hz), 65.9, 45.1, 19.2, 17.9, 15.1, 13.3; $[\alpha]_D^{20}$ −30.6 (c 0.5, MeOH).

Step E: (+)-(2-(5-Chloro-2-ethoxy-4-fluorophenyl)cyclopropyl)methanamine (HCl Salt)

The subtitle compound was prepared from (−)-tert-butyl ((2-(5-chloro-2-ethoxy-4-fluorophenyl)cyclopropyl)methyl)carbamate with 2M HCl (g) in ether as described in Example 1. $^1H$ NMR (400 MHz, $CD_3OD$) δ 7.05 (d, J=8.4 Hz, 1H), 6.88 (d, J=11.2 Hz, 1H), 4.09 (q, J=6.8 Hz, 2H), 3.06 (dd, J=12.8, 7.2 Hz, 1H), 2.97 (dd, J=13.2, 8.0 Hz, 1H), 2.07-2.03 (m, 1H), 1.46 (t, J=7.2 Hz, 3H), 1.32-1.27 (m, 1H), 1.11-1.07 (m, 1H), 1.04-1.00 (m, 1H); $^{13}C$ NMR (100 MHz, $CD_3OD$) δ 159.0, 158.5 (d, $J_{CF}$=243.6 Hz), 129.1, 128.0, 112.0 (d, $J_{CF}$=17.6 Hz), 101.9 (d, $J_{CF}$=25.0 Hz), 65.9, 45.1, 19.2, 17.8, 15.1, 13.3; $[\alpha]_D^{20}$ +28.8 (c 0.5, MeOH).

Example 3

(−)-(2-(5-Chloro-4-fluoro-2-isopropoxyphenyl)cyclopropyl)methanamine (HCl Salt)

(+)-(2-(5-Chloro-4-fluoro-2-isopropoxyphenyl)cyclopropyl)methanamine (HCl Salt)

Route 3:

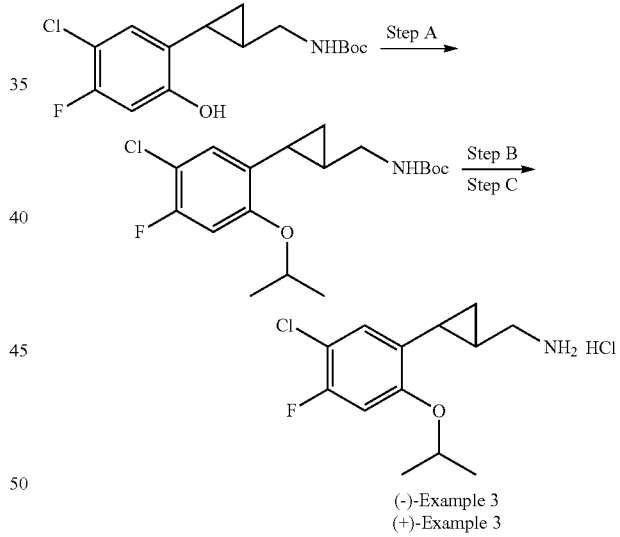

(−)-Example 3
(+)-Example 3

Step A: Tert-butyl ((2-(5-chloro-4-fluoro-2-isopropoxyphenyl)cyclopropyl)methyl)carbamate To a solution of tert-butyl ((2-(5-chloro-4-fluoro-2-hydroxyphenyl)cyclopropyl)methyl)carbamate (315 mg, 1.0 mmol) in anhydrous DMF (2 mL) was added $K_2CO_3$ (276 mg, 2.0 mmol) and 2-iodopropane (340 mg, 2.0 mmol) and the mixture was heat at 90° C. in a microwave reactor for 2 h. Water was added and the mixture was extracted with ethyl acetate, the combined extracts were dried over $Na_2SO_4$, concentrated and purified with flash chromatography to give the subtitle compound as colorless oil (160 mg, 45%). $^1H$ NMR ($CDCl_3$, 400 MHz) 6.90 (d, J=7.6 Hz, 1H), 6.65 (d, J=10.8 Hz, 1H), 5.09 (br, 1H), 4.57-4.51 (m, 2H), 3.60-3.58 (m, 1H), 2.70-2.64 (m, 1H), 1.74-1.70 (m, 1H), 1.46-1.40 (m, 15H), 1.03-0.99 (m, 1H), 0.96-0.92 (m, 2H), 0.81-0.78 (m, 1H). Step B: The racemic form of this compound (150 mg) was then separated with chiral HPLC using the same method as described in Example 1 and Example 2 to give (+)-tert-butyl ((2-(5-chloro-4-fluoro-2-isopropoxyphenyl) cyclopropyl)methyl)carbamate (70 mg, 100% ee) and (−)-tert-butyl ((2-(5-chloro-4-fluoro-2-isopropoxyphenyl)cyclopropyl)methyl)carbamate (50 mg, 95% ee) was separated as the second peak.

Step C: (−)-(2-(5-Chloro-4-fluoro-2-isopropoxyphenyl)cyclopropyl)methanamine (HCl Salt) and (+)-(2-(5-Chloro-4-fluoro-2-isopropoxyphenyl)cyclopropyl)methanamine (HCl Salt)

(−)-(2-(5-Chloro-4-fluoro-2-isopropoxyphenyl)cyclopropyl)methanamine (HCl Salt) and (+)-(2-(5-Chloro-4-fluoro-2-isopropoxyphenyl)cyclopropyl)methanamine (HCl salt) were prepared from (+)-tert-butyl ((2-(5-chloro-4-fluoro-2-isopropoxyphenyl)cyclopropyl)methyl)carbamate and (−)-tert-butyl ((2-(5-chloro-4-fluoro-2-isopropoxyphenyl)cyclopropyl)methyl)carbamate respectively with 2M HCl (g) in ether.

(−)-(2-(5-Chloro-4-fluoro-2-isopropoxyphenyl)cyclopropyl)methanamine (HCl salt). $^1$H NMR (400 MHz, CD$_3$OD) δ 7.04 (d, J=8.4 Hz, 1H), 6.90 (d, J=11.6 Hz, 1H), 4.66-4.60 (m, 1H), 3.15 (dd, J=12.8, 6.8 Hz, 1H), 2.89 (dd, J=12.8, 8.4 Hz, 1H), 2.06-2.01 (m, 1H), 1.45-1.30 (m, 7H), 1.08-0.99 (m, 2H); $[\alpha]_D^{20}$ −33.4 (c 0.5, MeOH).

(+)-(2-(5-Chloro-4-fluoro-2-isopropoxyphenyl)cyclopropyl)methanamine (HCl salt). $^1$H NMR (400 MHz, CD$_3$OD) δ 7.04 (d, J=8.4 Hz, 1H), 6.90 (d, J=11.6 Hz, 1H), 4.66-4.60 (m, 1H), 3.15 (dd, J=12.8, 6.8 Hz, 1H), 2.89 (dd, J=12.8, 8.4 Hz, 1H), 2.06-2.01 (m, 1H), 1.45-1.30 (m, 7H), 1.08-0.99 (m, 2H); $[\alpha]_D^{20}$ +32.8 (c 0.5, MeOH).

Example 4

(−)-(2-(5-Chloro-4-fluoro-2-(2-fluoroethoxy)phenyl) cyclopropyl)methanamine (HCl Salt)

(+)-(2-(5-Chloro-4-fluoro-2-(2-fluoroethoxy)phenyl) cyclopropyl)methanamine (HCl Salt)

Route 4:

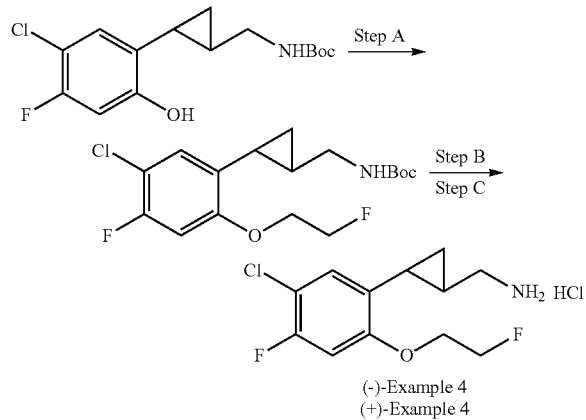

(−)-Example 4
(+)-Example 4

Step A: Tert-butyl ((2-(5-chloro-4-fluoro-2-(2-fluoroethoxy)phenyl)cyclopropyl)methyl)carbamate A solution of tert-butyl ((2-(5-chloro-4-fluoro-2-hydroxyphenyl)cyclopropyl)methyl)carbamate (316 mg, 1.0 mmol), 2-fluoroethanol (192 mg, 3 mmol) and triphenylphosphine (787 mg, 3 mmol) in anhydrous THF (3 mL) was cooled at 0° C. To this solution was added dropwise diethyl azodicarboxylate (522 mg, 3 mmol). And the mixture was then heated with microwave at 60° C. for 1 h before being concentrated and purified with flash chromatography (0-30% ethyl acetate in hexane) to give the subtitle compound as a colorless oil (280 mg, 78%). $^1$H NMR (CDCl$_3$, 400 MHz) 6.93 (d, J=8.4 Hz, 1H), 6.65 (d, J=10.8 Hz, 1H), 4.98 (br, 1H), 4.93-4.88 (m, 2H), 4.28-4.19 (m, 2H), 3.52-3.48 (m, 1H), 2.82-2.79 (m, 1H), 1.82-1.79 (m, 1H), 1.45 (s, 9H), 1.05-0.95 (m, 2H), 0.85-0.80 (m, 1H).

Step B (+)-Tert-butyl ((2-(5-fluoro-2-(2-fluoroethoxy)phenyl)cyclopropyl) methyl)carbamate (90 mg, >99% ee) and (−)-tert-butyl ((2-(5-fluoro-2-(2-fluoroethoxy)phenyl) cyclopropyl)methyl)carbamate (90 mg, >99% ee) were prepared using chiral HPLC as described above.

Step C: (−)-(2-(5-Chloro-4-fluoro-2-(2-fluoroethoxy)phenyl)cyclopropyl)methanamine (HCl Salt) and (+)-(2-(5-Chloro-4-fluoro-2-(2-fluoroethoxy) phenyl)cyclopropyl)methanamine (HCl Salt)

(−)-(2-(5-Chloro-4-fluoro-2-(2-fluoroethoxy)phenyl)cyclopropyl)methanamine (HCl salt) and (+)-(2-(5-Chloro-4-fluoro-2-(2-fluoroethoxy)phenyl)cyclopropyl)methanamine (HCl salt) were prepared from (+)-Tert-butyl ((2-(5-fluoro-2-(2-fluoroethoxy)phenyl)cyclopropyl) methyl)carbamate and (−)-tert-butyl ((2-(5-fluoro-2-(2-fluoroethoxy)phenyl) cyclopropyl)methyl)carbamate respectively, with HCl in Et$_2$O using the same method as described above.

(−)-(2-(5-Chloro-4-fluoro-2-(2-fluoroethoxy)phenyl)cyclopropyl)methanamine (HCl salt) H NMR (400 MHz, CD$_3$OD) δ 7.10 (d, J=8.0 Hz, 1H), 6.96 (d, J=11.2 Hz, 1H), 4.86-4.76 (m, 2H), 4.35-4.24 (m, 2H), 3.05-2.97 (m, 2H), 2.10-2.04 (m, 1H), 1.26-1.15 (m, 2H), 1.05-1.00 (m, 1H); $^{13}$C NMR (100 MHz, CD$_3$OD) δ 158.6, 158.5 (d, $J_{CF}$=244.2 Hz), 129.5, 128.3, 112.7 (d, $J_{CF}$=17.8 Hz), 102.3 (d, $J_{CF}$=25.4 Hz), 83.3 (d, $J_{CF}$=167.0 Hz), 69.7 (d, $J_{CF}$=18.8 Hz), 45.0, 19.5, 17.8, 12.6; $[\alpha]_D^{20}$ −26.4 (c 0.5, MeOH).

(+)-(2-(5-Chloro-4-fluoro-2-(2-fluoroethoxy)phenyl)cyclopropyl)methanamine (HCl salt). $^1$H NMR (400 MHz, CD$_3$OD) δ 7.10 (d, J=8.4 Hz, 1H), 6.96 (d, J=10.8 Hz, 1H), 4.86-4.75 (m, 2H), 4.34-4.24 (m, 2H), 3.04-2.98 (m, 2H), 2.09-2.04 (m, 1H), 1.25-1.15 (m, 2H), 1.05-1.00 (m, 1H); $^{13}$C NMR (100 MHz, CD$_3$OD) δ 158.6, 158.5 (d, $J_{CF}$=243.9 Hz), 129.5, 128.3, 112.7 (d, $J_{CF}$=17.5 Hz), 102.3 (d, $J_{CF}$=25.5 Hz), 83.3 (d, $J_{CF}$=167.1 Hz), 69.7 (d, $J_{CF}$=19.0 Hz), 45.0, 19.5, 17.8, 12.6; $[\alpha]_D^{20}$ +28.4 (c 0.5, MeOH).

Example 5

(−)-(2-(2-(Allyloxy)-5-chloro-4-fluorophenyl)cyclopropyl)methanamine (HCl Salt)

(+)-(2-(2-(Allyloxy)-5-chloro-4-fluorophenyl)cyclopropyl)methanamine (HCl Salt)

Route 5:

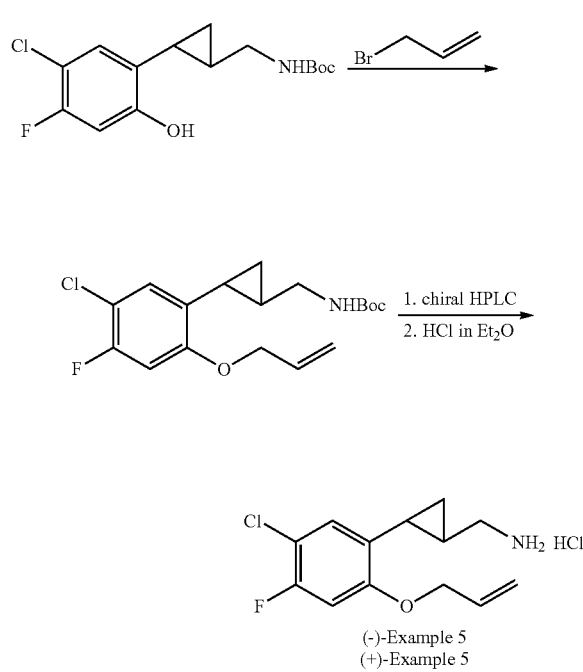

(−)-Example 5
(+)-Example 5

The title compounds were prepared via Route 5 using similar methods described above. The first step was conducted using allyl bromide with the alkylating reagent, in the presence of $K_2CO_3$ as the base and DMF as the solvent.

(−)-(2-(2-(Allyloxy)-5-chloro-4-fluorophenyl)cyclopropyl)methanamine (HCl salt). $^1$H NMR (400 MHz, $CD_3OD$) δ 7.07 (d, J=8.4 Hz, 1H), 6.90 (d, J=11.2 Hz, 1H), 6.18-6.08 (m, 1H), 5.47 (dd, J=13.6, 1.6 Hz, 1H), 5.34 (dd, J=10.4, 1.6 Hz, 1H), 4.62 (d, J=5.2 Hz, 2H), 3.06 (dd, J=12.8, 7.2 Hz, 1H), 2.98 (dd, J=12.8, 8.0 Hz, 1H), 2.11-2.05 (m, 1H), 1.32-1.28 (m, 1H), 1.13-1.01 (m, 2H); $^{13}$C NMR (100 MHz, $CD_3OD$) δ 158.5, 158.4 (d, $J_{CF}$=243.8 Hz), 134.3, 129.2, 128.3, 118.8, 112.3 (d, $J_{CF}$=17.6 Hz), 102.4 (d, $J_{CF}$=25.4 Hz), 70.9, 45.0, 19.2, 17.9, 13.2; $[α]_D^{20}$ −36.2 (c 0.5, MeOH).

(+)-(2-(2-(Allyloxy)-5-chloro-4-fluorophenyl)cyclopropyl)methanamine (HCl salt). $^1$H NMR (400 MHz, $CD_3OD$) δ 7.07 (d, J=8.4 Hz, 1H), 6.91 (d, J=11.2 Hz, 1H), 6.17-6.08 (m, 1H), 5.47 (dd, J=13.6, 1.6 Hz, 1H), 5.34 (dd, J=11.2, 1.2 Hz, 1H), 4.62 (d, J=5.2 Hz, 2H), 3.06 (dd, J=11.2, 7.2 Hz, 1H), 2.99 (dd, J=12.8, 5.6 Hz, 1H), 2.11-2.05 (m, 1H), 1.32-1.28 (m, 1H), 1.13-1.01 (m, 2H); $^{13}$C NMR (100 MHz, $CD_3OD$) δ 158.5, 158.4 (d, $J_{CF}$=243.7 Hz), 134.3, 129.2, 128.3, 118.8, 112.3 (d, $J_{CF}$=17.6 Hz), 102.4 (d, $J_{CF}$=25.4 Hz), 70.9, 45.0, 19.2, 17.9, 13.2; $[α]_D^{20}$ +34.6 (c 0.5, MeOH).

Example 6

(−)-(2-(5-Chloro-4-fluoro-2-(prop-2-yn-1-yloxy)phenyl)cyclopropyl)methanamine (HCl Salt)

(+)-(2-(5-Chloro-4-fluoro-2-(prop-2-yn-1-yloxy)phenyl)cyclopropyl)methanamine (HCl Salt)

Route 6:

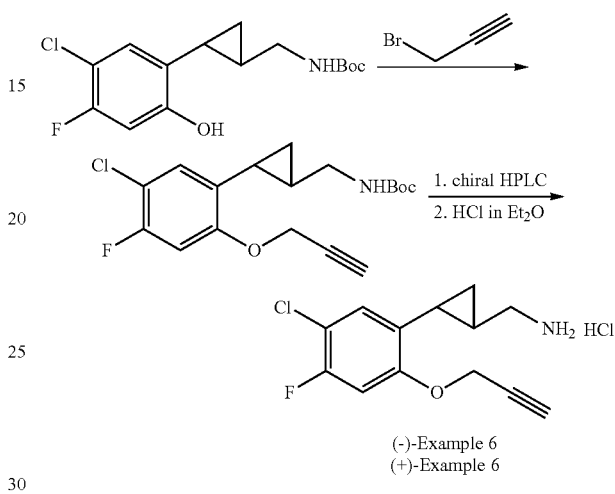

(−)-Example 6
(+)-Example 6

The title compounds were prepared via Route 6 using similar methods described above. Propargyl bromide was used as the alkylating reagent in the first step.

(−)-(2-(5-Chloro-4-fluoro-2-(prop-2-yn-1-yloxy)phenyl)cyclopropyl)methanamine (HCl salt). $^1$H NMR (400 MHz, $CD_3OD$) δ 7.11 (d, J=8.4 Hz, 1H), 7.02 (d, J=10.8 Hz, 1H), 4.85 (d, J=2.4 Hz, 2H), 3.12 (t, J=1.6 Hz, 1H), 3.07 (dd, J=13.2, 7.2 Hz, 1H), 2.95 (dd, J=12.8, 8.0 Hz, 1H), 2.06-2.02 (m, 1H), 1.27-1.23 (m, 1H), 1.16-1.12 (m, 1H), 1.05-1.00 (m, 1H); $[α]_D^{20}$ −31.4 (c 0.5, MeOH).

(+)-(2-(5-Chloro-4-fluoro-2-(prop-2-yn-1-yloxy)phenyl)cyclopropyl)methanamine (HCl salt). $^1$H NMR (400 MHz, $CD_3OD$) δ 7.11 (d, J=8.4 Hz, 1H), 7.02 (d, J=11.2 Hz, 1H), 4.85 (d, J=2.4 Hz, 2H), 3.12 (t, J=1.6 Hz, 1H), 3.07 (dd, J=13.2, 7.2 Hz, 1H), 2.95 (dd, J=12.8, 8.0 Hz, 1H), 2.06-2.02 (m, 1H), 1.27-1.23 (m, 1H), 1.16-1.11 (m, 1H), 1.05-1.00 (m, 1H); $[α]_D^{20}$ +31.2 (c 0.5, MeOH).

Example 7

(−)-(2-(5-Fluoro-2-propoxyphenyl)cyclopropyl)methanamine (HCl Salt)

(+)-(2-(5-Fluoro-2-propoxyphenyl)cyclopropyl)methanamine (HCl Salt)

Route 7:

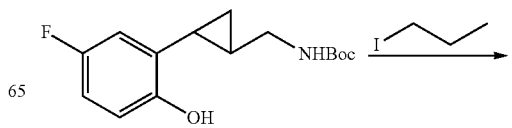

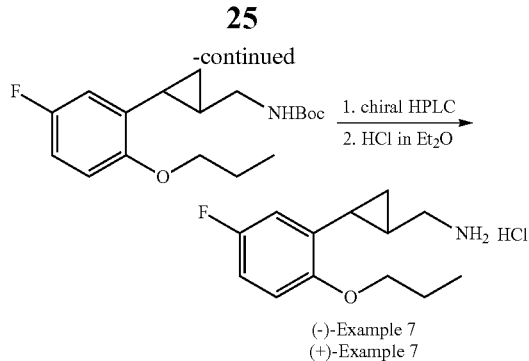

(−)-Example 7
(+)-Example 7

The title compounds were prepared with Route 7 using tert-butyl ((2-(5-fluoro-2-hydroxyphenyl)cyclopropyl) methyl)carbamate (prepared according to US20130281539) as the starting material. 1-Iodopropane was used as the alkylating reagent in the first step.

(−)-(2-(5-Fluoro-2-propoxyphenyl)cyclopropyl)methanamine (HCl salt). $^1$H NMR (400 MHz, CD$_3$OD) δ 6.93-6.86 (m, 2H), 6.73 (dd, J=9.4, 3.2 Hz, 1H), 6.17-6.10 (m, 1H), 5.45 (dd, J=17.2, 1.6 Hz, 1H), 5.30 (dd, J=10.4, 1.6 Hz, 1H), 4.60 (d, J=5.6 Hz, 2H), 3.06 (dd, J=13.2, 7.6 Hz, 1H), 2.98 (dd, J=13.2, 4.2 Hz, 1H), 2.21-2.15 (m, 1H), 1.34-1.30 (m, 1H), 1.14-1.02 (m, 2H); $^{13}$C NMR (100 MHz, CD$_3$OD) δ 158.8 (d, $J_{CF}$=225.7 Hz), 154.9, 135.0, 133.0 (d, $J_{CF}$=7.4 Hz), 118.2, 114.3 (d, $J_{CF}$=17.8 Hz), 114.1, 114.0 (d, $J_{CF}$=37.3 Hz), 71.0, 45.1, 19.7, 18.3, 13.7; HRMS (ESI) calculated for [M+H]: 224.1451, found: 224.1428; $[α]_D^{20}$ −16.2 (c 0.4, MeOH).

(+)-(2-(5-Fluoro-2-propoxyphenyl)cyclopropyl)methanamine (HCl salt). $^1$H NMR (400 MHz, CD$_3$OD) δ 6.92-6.84 (m, 2H), 6.72 (dd, J=9.6, 2.8 Hz, 1H), 4.02-3.93 (m, 2H), 3.14 (dd, J=13.2, 6.8 Hz, 1H), 2.91 (dd, J=13.2, 8.0 Hz, 1H), 2.21-2.15 (m, 1H), 1.91-1.81 (m, 2H), 1.38-1.33 (m, 1H), 1.12-1.02 (m, 5H); $^{13}$C NMR (100 MHz, CD$_3$OD) δ 158.6 (d, $J_{CF}$=235.2 Hz), 155.4, 132.8 (d, $J_{CF}$=6.8 Hz), 114.0 (d, $J_{CF}$=24.0 Hz), 113.9 (d, $J_{CF}$=23.2 Hz), 113.8 (d, $J_{CF}$=8.3 Hz), 71.7, 45.1, 23.9, 19.6, 18.4, 13.9, 11.1; HRMS (ESI) calculated for [M+H]: 224.1451, found: 224.1428; $[α]_D^{20}$ +22.5 (c 0.5, MeOH).

Example 8

(−)-(2-(2-(Allyloxy)-5-fluorophenyl)cyclopropyl) methanamine (HCl Salt)

(+)-(2-(2-(Allyloxy)-5-fluorophenyl)cyclopropyl) methanamine (HCl Salt)

Route 8:

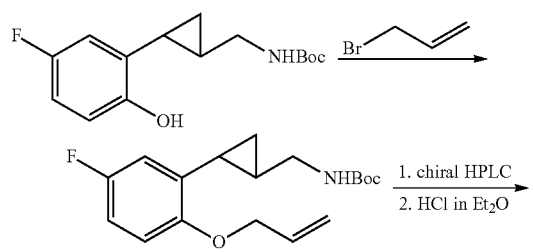

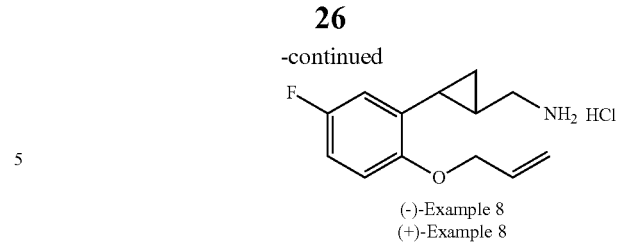

(−)-Example 8
(+)-Example 8

The title compounds were prepared via Route 8 using similar methods described above.

(−)-(2-(2-(Allyloxy)-5-fluorophenyl)cyclopropyl)methanamine (HCl salt). $^1$H NMR (400 MHz, CD$_3$OD) δ 6.93-6.86 (m, 2H), 6.73 (dd, J=9.4, 3.2 Hz, 1H), 6.17-6.10 (m, 1H), 5.45 (dd, J=17.2, 1.6 Hz, 1H), 5.30 (dd, J=10.4, 1.6 Hz, 1H), 4.60 (d, J=5.6 Hz, 2H), 3.06 (dd, J=13.2, 7.6 Hz, 1H), 2.98 (dd, J=13.2, 4.2 Hz, 1H), 2.21-2.15 (m, 1H), 1.34-1.30 (m, 1H), 1.14-1.02 (m, 2H); $^{13}$C NMR (100 MHz, CD$_3$OD) δ 158.8 (d, $J_{CF}$=225.7 Hz), 154.9, 135.0, 133.0 (d, $J_{CF}$=7.4 Hz), 118.2, 114.3 (d, $J_{CF}$=17.8 Hz), 114.1, 114.0 (d, $J_{CF}$=37.3 Hz), 71.0, 45.1, 19.7, 18.3, 13.7; HRMS (ESI) calculated for [M+H]: 222.1294, found: 222.1273; $[α]_D^{20}$ −16.2 (c 0.4, MeOH).

(+)-(2-(2-(Allyloxy)-5-fluorophenyl)cyclopropyl)methanamine (HCl salt). $^1$H NMR (400 MHz, CD$_3$OD) δ 6.93-6.86 (m, 2H), 6.73 (dd, J=9.6, 3.2 Hz, 1H), 6.17-6.10 (m, 1H), 5.45 (dd, J=17.2, 1.6 Hz, 1H), 5.30 (dd, J=10.4, 1.6 Hz, 1H), 4.60 (d, J=4.2 Hz, 2H), 3.07 (dd, J=12.8, 7.2 Hz, 1H), 2.98 (dd, J=13.2, 5.6 Hz, 1H), 2.21-2.17 (m, 1H), 1.35-1.31 (m, 1H), 1.14-1.04 (m, 2H); $^{13}$C NMR (100 MHz, CD$_3$OD) δ 158.8 (d, $J_{CF}$=235.7 Hz), 155.0, 135.0, 133.0 (d, $J_{CF}$=7.4 Hz), 118.2, 114.3 (d, $J_{CF}$=17.0 Hz), 114.1, 114.0 (d, $J_{CF}$=36.1 Hz), 71.0, 45.1, 19.7, 18.3, 13.7; HRMS (ESI) calculated for [M+H]: 222.1294, found: 222.1273; $[α]_D^{20}$ +17.5 (c 0.2, MeOH).

Example 9

(−)-(2-(5-Fluoro-2-((2-fluoroallyl)oxy)phenyl)cyclopropyl)methanamine (HCl Salt)

(+)-(2-(5-Fluoro-2-((2-fluoroallyl)oxy)phenyl)cyclopropyl)methanamine (HCl Salt)

Route 9:

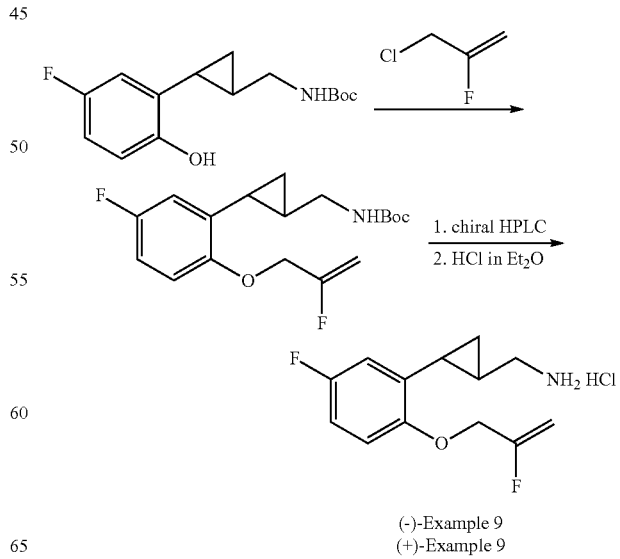

(−)-Example 9
(+)-Example 9

The title compounds were prepared via Route 9 using similar methods described above.

(−)-(2-(5-Fluoro-2-((2-fluoroallyl)oxy)phenyl)cyclopropyl)methanamine (HCl salt). $^1$H NMR (400 MHz, CD$_3$OD) δ 6.98 (dd, J=8.8, 4.4 Hz, 1H), 6.90 (dt, J=8.0, 2.8 Hz, 1H), 6.76 (dd, J=9.2, 2.8 Hz, 1H), 4.88 (dd, J=14.0, 3.2 Hz, 1H), 4.80 (dd, J=41.6, 2.8 Hz, 1H), 4.66 (d, J=14.0 Hz, 2H), 3.11 (dd, J=13.2, 7.2 Hz, 1H), 2.95 (dd, J=13.2, 8.0 Hz, 1H), 2.21-2.15 (m, 1H), 1.37-1.32 (m, 1H), 1.15-1.05 (m, 2H); $^{13}$C NMR (100 MHz, CD$_3$OD) δ 163.0 (d, $J_{CF}$=256.2 Hz), 159.2 (d, $J_{CF}$=236.7 Hz), 154.5, 133.5 (d, $J_{CF}$=7.4 Hz), 114.8 (d, $J_{CF}$=8.4 Hz), 114.3, 114.2 (d, $J_{CF}$=48.3 Hz), 94.8 (d, $J_{CF}$=16.7 Hz), 67.8 (d, $J_{CF}$=32.4 Hz), 45.0, 19.8, 18.2, 13.7; HRMS (ESI) calculated for [M+H]: 240.1200, found: 240.1178; $[α]_D^{20}$ −14.3 (c 0.75, MeOH).

(+)-(2-(5-Fluoro-2-((2-fluoroallyl)oxy)phenyl)cyclopropyl)methanamine (HCl salt). $^1$H NMR (400 MHz, CD$_3$OD) δ 6.98 (dd, J=8.8, 4.4 Hz, 1H), 6.90 (dt, J=8.0, 2.8 Hz, 1H), 6.76 (dd, J=9.2, 2.8 Hz, 1H), 4.88 (dd, J=14.0, 3.2 Hz, 1H), 4.80 (dd, J=41.6, 2.8 Hz, 1H), 4.66 (d, J=14.0 Hz, 2H), 3.11 (dd, J=13.2, 6.8 Hz, 1H), 2.95 (dd, J=13.2, 8.0 Hz, 1H), 2.21-2.16 (m, 1H), 1.37-1.33 (m, 1H), 1.16-1.05 (m, 2H); $^{13}$C NMR (100 MHz, CD$_3$OD) δ 163.0 (d, $J_{CF}$=256.2 Hz), 159.2 (d, $J_{CF}$=236.6 Hz), 154.5, 133.5 (d, $J_{CF}$=7.5 Hz), 114.9 (d, $J_{CF}$=8.6 Hz), 114.3, 114.2 (d, $J_{CF}$=45.5 Hz), 94.8 (d, $J_{CF}$=16.7 Hz), 67.8 (d, $J_{CF}$=32.3 Hz), 45.0, 19.8, 18.3, 13.7; HRMS (ESI) calculated for [M+H]: 240.1200, found: 240.1176; $[α]_D^{20}$ +16.0 (c 0.3, MeOH).

Example 10

(−)-(2-(5-Fluoro-2-(2-fluoroethoxy)phenyl)cyclopropyl)methanamine (HCl Salt)

(+)-(2-(5-Fluoro-2-(2-fluoroethoxy)phenyl)cyclopropyl)methanamine (HCl Salt)

Route 10:

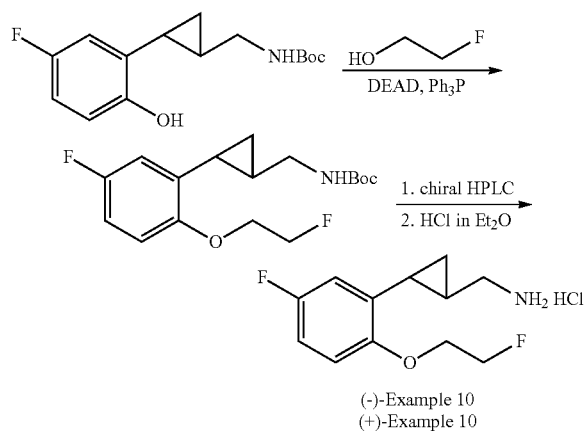

(−)-Example 10
(+)-Example 10

The title compounds were prepared via Route 10 using similar methods described above.

(−)-(2-(5-Fluoro-2-(2-fluoroethoxy)phenyl)cyclopropyl)methanamine (HCl salt). $^1$H NMR (400 MHz, CD$_3$OD) δ 6.97-6.86 (m, 2H), 6.76 (dd, J=9.2, 2.8 Hz, 1H), 4.87-4.75 (m, 2H), 4.32-4.20 (m, 2H), 3.04-3.00 (m, 2H), 2.19-2.15 (m, 1H), 1.28-1.17 (m, 2H), 1.06-1.02 (m, 1H); $^{13}$C NMR (100 MHz, CD$_3$OD) δ 159.0 (d, $J_{CF}$=236.0 Hz), 155.0, 133.0 (d, $J_{CF}$=7.4 Hz), 114.6 (d, $J_{CF}$=24.0 Hz), 114.2 (d, $J_{CF}$=22.8 Hz), 114.0 (d, $J_{CF}$=8.1 Hz), 83.6 (d, $J_{CF}$=166.6 Hz), 69.7 (d, $J_{CF}$=18.9 Hz), 45.0, 20.0, 18.3, 13.0; HRMS (ESI) calculated for [M+H]: 228.1200, found: 228.1179; $[α]_D^{20}$ −3.3 (c 0.3, MeOH).

(+)-(2-(5-Fluoro-2-(2-fluoroethoxy)phenyl)cyclopropyl)methanamine (HCl salt). $^1$H NMR (400 MHz, CD$_3$OD) δ 6.97-6.88 (m, 2H), 6.76 (dd, J=9.6, 3.2 Hz, 1H), 4.87-4.74 (m, 2H), 4.32-4.22 (m, 2H), 3.03 (d, J=7.6 Hz, 2H), 2.20-2.15 (m, 1H), 1.28-1.25 (m, 1H), 1.22-1.17 (m, 1H), 1.07-1.02 (m, 1H); $^{13}$C NMR (100 MHz, CD$_3$OD) δ 159.0 (d, $J_{CF}$=236.2 Hz), 155.0, 133.1 (d, $J_{CF}$=7.3 Hz), 114.6 (d, $J_{CF}$=24.0 Hz), 114.2 (d, $J_{CF}$=17.5 Hz), 114.1 (d, $J_{CF}$=3.1 Hz), 83.6 (d, $J_{CF}$=166.6 Hz), 69.7 (d, $J_{CF}$=19.8 Hz), 45.0, 20.0, 18.3, 13.1; HRMS (ESI) calculated for [M+H]: 228.1200, found: 228.1173; $[α]_D^{20}$ +3.6 (c 0.3, MeOH).

Example 11

(−)-(2-(5-Chloro-2-ethoxyphenyl)cyclopropyl)methanamine (HCl Salt)

(+)-(2-(5-Chloro-2-ethoxyphenyl)cyclopropyl)methanamine (HCl Salt)

Route 11:

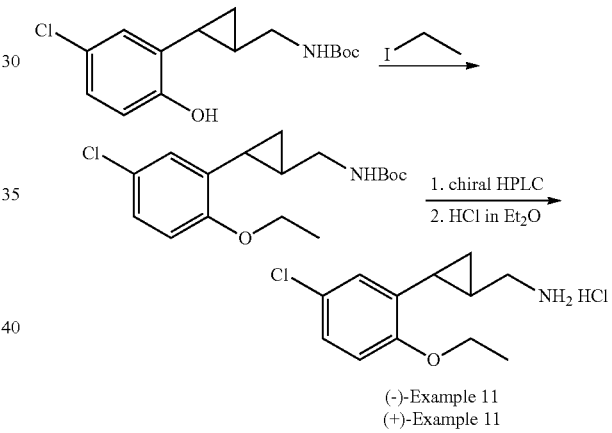

(−)-Example 11
(+)-Example 11

The title compounds were prepared via Route 11 using tert-butyl ((2-(5-chloro-2-hydroxyphenyl)cyclopropyl)methyl)carbamate (prepared using the similar methods described for tert-butyl ((2-(5-fluoro-2-hydroxyphenyl)cyclopropyl)methyl)carbamate in US20130281539) as the starting material.

(−)-(2-(5-Chloro-2-ethoxyphenyl)cyclopropyl)methanamine (HCl salt). $^1$H NMR (400 MHz, CD$_3$OD) δ 7.13 (dd, J=8.8, 2.8 Hz, 1H), 6.95 (d, J=2.4 Hz, 1H), 6.90 (d, J=8.8 Hz, 1H), 4.13-4.06 (m, 2H), 3.06 (dd, J=13.2, 7.2 Hz, 1H), 2.99 (dd, J=13.2, 5.6 Hz, 1H), 2.15-2.11 (m, 1H), 1.45 (t, J=7.2 Hz, 3H), 1.35-1.32 (m, 1H), 1.13-1.08 (m, 1H), 1.06-1.02 (m, 1H); $^{13}$C NMR (100 MHz, CD$_3$OD) δ 157.9, 132.7, 128.1, 127.5, 126.5, 113.8, 65.4, 45.1, 19.4, 18.2, 15.3, 13.6; HRMS calculated for [M+H]: 226.0993, found: 227.1001; $[α]_D^{20}$ −47.2 (c 0.5, MeOH).

(+)-(2-(5-Chloro-2-ethoxyphenyl)cyclopropyl)methanamine HCl salt. $^1$H NMR (400 MHz, CD$_3$OD) δ 7.14 (dd, J=8.8, 2.8 Hz, 1H), 6.95 (d, J=2.8 Hz, 1H), 6.90 (d, J=8.8 Hz, 1H), 4.13-4.06 (m, 2H), 3.06 (dd, J=12.8, 7.2 Hz, 1H), 2.98 (dd, J=12.8, 8.0 Hz, 1H), 2.15-2.11 (m, 1H), 1.45 (t, J=6.8 Hz, 3H), 1.35-1.31 (m, 1H), 1.13-1.08 (m, 1H), 1.06-1.02 (m, 1H); $^{13}$C NMR (100 MHz, CD$_3$OD) δ 157.9, 132.7, 128.1, 127.5, 126.5, 113.8, 65.4, 45.1, 19.4, 18.2, 15.3, 13.6; HRMS calculated for [M+H]: 226.0993, found: 227.1003. $[α]_D^{20}$ +39.4 (c 0.5, MeOH).

Example 12

(−)-(2-(5-Chloro-2-propoxyphenyl)cyclopropyl)methanamine (HCl Salt)

(+)-(2-(5-Chloro-2-propoxyphenyl)cyclopropyl)methanamine (HCl Salt)

Route 12:

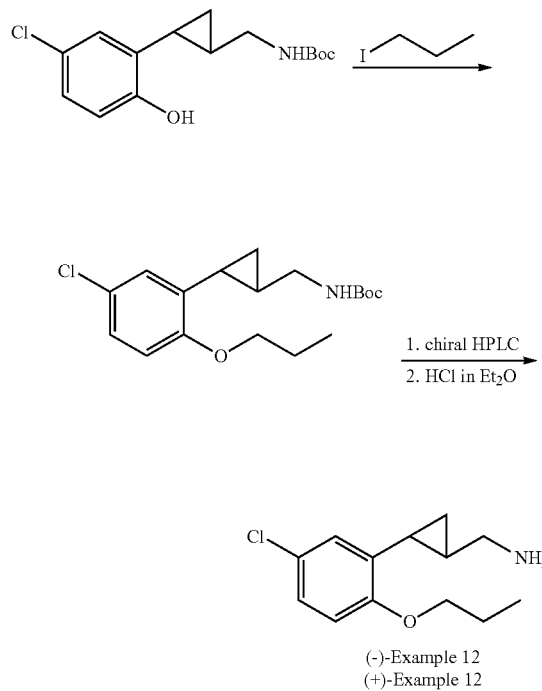

(−)-Example 12
(+)-Example 12

The title compounds were prepared via Route 12 using similar methods described above.

(−)-(2-(5-Chloro-2-propoxyphenyl)cyclopropyl)methanamine (HCl salt). $^1$H NMR (CD$_3$OD, 360 MHz) δ 7.11 (dd, J=8.7, 2.6 Hz, 1H), 6.94 (d, J=2.6 Hz, 1H), 6.87 (d, J=8.7 Hz, 1H), 3.96 (m, 1H), 3.12 (dd, J=13.1, 6.8 Hz, 1H), 2.89 (dd, J=13.1, 8.2 Hz, 1H), 2.14-2.09 (m, 1H), 1.89-1.82 (m, 2H), 1.37-1.32 (m, 1H), 1.10-1.01 (m, 5H); $^{13}$C NMR (CD$_3$OD, 100 MHz) δ 156.7, 131.5, 126.8, 126.1, 125.2, 112.5, 70.1, 43.8, 22.5, 18.0, 17.0, 12.5, 9.8; HRMS (ESI): m/z [M+H]$^+$ calculated: 240.1155, found: 240.1163; $[α]_D^{20}$ −46.9 (c 0.3, CD$_3$OD).

(+)-(2-(5-Chloro-2-propoxyphenyl)cyclopropyl)methanamine (HCl salt). $^1$H NMR (CD$_3$OD, 400 MHz) δ 7.13 (dd, J=8.7, 2.6 Hz, 1H), 6.95 (d, J=2.6 Hz, 1H), 6.89 (d, J=8.7 Hz, 1H), 3.98 (m, 1H), 3.14 (dd, J=13.1, 6.8 Hz, 1H), 2.91 (dd, J=13.1, 8.2 Hz, 1H), 2.15-2.11 (m, 1H), 1.87-1.83 (m, 2H), 1.38-1.34 (m, 1H), 1.11-1.02 (m, 5H); HRMS (ESI): m/z [M+H]$^+$ calculated for C$_{13}$H$_{19}$ClNO: 240.1155, found: 240.1220; $[α]_D^{20}$ +43.4 (c 0.2, CD$_3$OD).

Example 13

(−)-(2-(2-Butoxy-5-chlorophenyl)cyclopropyl)methanamine (TFA Salt)

(+)-(2-(2-Butoxy-5-chlorophenyl)cyclopropyl)methanamine (TFA Salt)

Route 13:

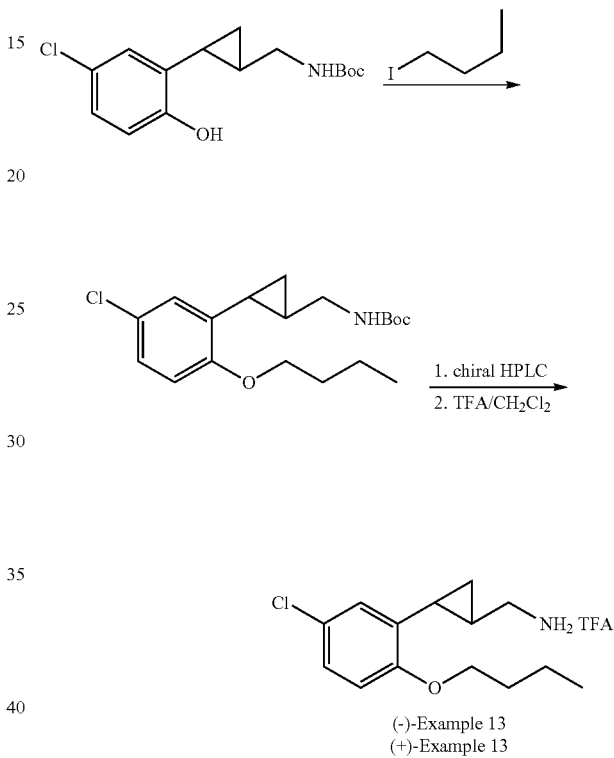

(−)-Example 13
(+)-Example 13

The title compounds were prepared via Route 13 using similar methods described above.

(−)-(2-(2-Butoxy-5-chlorophenyl)cyclopropyl)methanamine (TFA salt). $^1$H NMR (CD$_3$OD, 400 MHz) δ 7.14 (dd, J=2.4, 8.8 Hz, 1H), 6.94 (d, J=2.4 Hz, 1H), 6.91 (d, J=8.8 Hz, 1H), 4.01 (m, 2H), 3.13 (dd, J=13.2, 7.2 Hz, 1H), 2.90 (dd, J=13.2, 7.2 Hz, 1H), 2.12 (m, 1H), 1.81 (m, 2H), 1.56 (m, 2H), 1.35 (m, 1H), 1.09-0.99 (m, 5H); $^{13}$C NMR (CD$_3$OD, 100 MHz) δ 158.0, 132.7, 128.1, 127.4, 126.5, 113.8, 69.5, 45.1, 32.6, 20.5, 19.3, 18.3, 14.3, 13.7; HRMS (ESI) calcd for C$_{14}$H$_{20}$NOCl ([M+H]$^+$) 254.1306; found: 254.1306; $[α]_D^{20}$ −30.4 (c 0.12, CH$_3$OH).

(+)-(2-(2-Butoxy-5-chlorophenyl)cyclopropyl)methanamine (TFA salt). $^1$H NMR (CD$_3$OD, 400 MHz) δ 7.14 (dd, J=8.8, 2.4 Hz, 1H), 6.94 (d, J=2.4 Hz, 1H), 6.91 (d, J=8.8 Hz, 1H), 4.01 (m, 2H), 3.13 (dd, J=12.8, 6.8 Hz, 1H), 2.90 (dd, J=12.8, 8.4 Hz, 1H), 2.12 (m, 1H), 1.81 (m, 2H), 1.54 (m, 2H), 1.33 (m, 1H), 1.08-0.99 (m, 5H); $^{13}$C NMR (CD$_3$OD, 100 MHz) δ 158.0, 132.7, 128.1, 127.4, 126.5, 113.8, 69.5, 45.1, 32.6, 20.5, 19.3, 18.3, 14.3, 13.7; HRMS (ESI) calcd for C$_{14}$H$_{20}$NOCl ([M+H]$^+$) 254.1306; found: 254.1317; $[α]_D^{20}$ +32.0 (c 0.14, CH$_3$OH).

Example 14

(−)-(2-(5-Chloro-2-isopropoxyphenyl)cyclopropyl)methanamine (HCl Salt)

(+)-(2-(5-Chloro-2-isopropoxyphenyl)cyclopropyl)methanamine (HCl Salt)

Route 14:

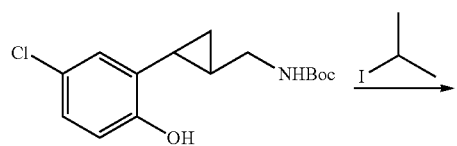

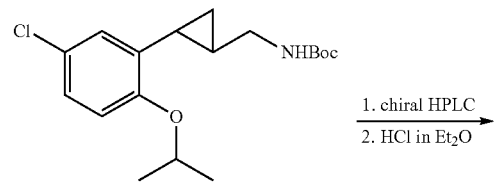

(−)-Example 14
(+)-Example 14

The title compounds were prepared via Route 14 using similar methods described above.

(−)-(2-(5-Chloro-2-isopropoxyphenyl)cyclopropyl)methanamine (HCl salt). $^1$H NMR (CD$_3$OD, 400 MHz) δ 7.13 (dd, J=8.8, 2.4 Hz, 1H), 6.93 (m, 2H), 4.63 (m, 1H), 3.14 (dd, J=13.2, 6.8 Hz, 1H), 2.89 (dd, J=12.8, 8.4 Hz, 1H), 2.10 (m, 1H), 1.38-1.33 (m, 7H), 1.08-1.01 (m, 2H); $^{13}$C NMR (CD$_3$OD, 100 MHz) δ 156.7, 133.7, 128.0, 127.5, 126.5, 115.8, 72.1, 45.1, 22.6, 22.4, 19.5, 18.4, 13.8; HRMS (ESI) calcd for C$_{13}$H$_{18}$NOCl ([M+H]$^+$) 240.1150; found: 240.1155; [α]$_D^{20}$ −45.9 (c 0.17, CH$_3$OH).

(+)-(2-(5-Chloro-2-isopropoxyphenyl)cyclopropyl)methanamine (HCl salt). $^1$H NMR (CD$_3$OD, 400 MHz) δ 7.12 (dd, J=8.8, 2.4 Hz, 1H), 6.93 (m, 2H), 4.62 (m, 1H), 3.15 (dd, J=13.2, 6.4 Hz, 1H), 2.89 (dd, J=13.2, 8.0 Hz, 1H), 2.11 (m, 1H), 1.37-1.33 (m, 7H), 1.09-1.00 (m, 2H); $^{13}$C NMR (CD$_3$OD, 100 MHz) δ 156.7, 133.7, 128.0, 127.5, 126.5, 115.8, 72.1, 45.1, 22.6, 22.4, 19.5, 18.4, 13.8; HRMS (ESI) calcd for C$_{13}$H$_{18}$NOCl ([M+H]$^+$) 240.1150; found: 240.1156; [α]$_D^{20}$ +44.7 (c 0.17, CH$_3$OH).

Example 15

(−)-(2-(5-Chloro-2-isobutoxyphenyl)cyclopropyl)methanamine (TFA Salt)

(+)-(2-(5-Chloro-2-isobutoxyphenyl)cyclopropyl)methanamine (TFA Salt)

Route 15:

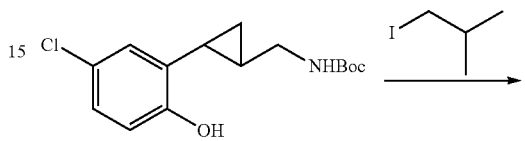

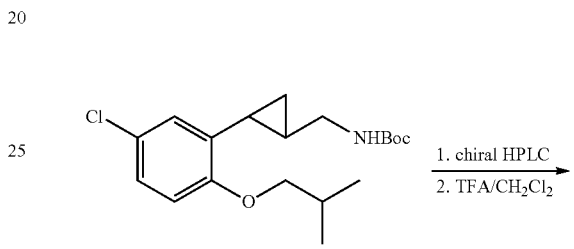

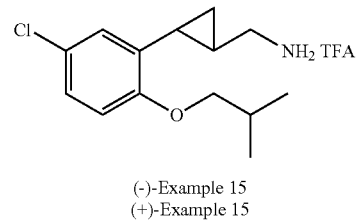

(−)-Example 15
(+)-Example 15

The title compounds were prepared via Route 15 using similar methods described above.

(−)-(2-(5-Chloro-2-isobutoxyphenyl)cyclopropyl)methanamine (TFA salt). $^1$H NMR (CD$_3$OD, 400 MHz) δ 7.13 (dd, J=2.4, 8.8 Hz, 1H), 6.95 (d, J=2.4 Hz, 1H), 6.89 (d, J=8.8 Hz, 1H), 3.81-3.74 (m, 2H), 3.21 (dd, J=6.4, 13.2 Hz, 1H), 2.85 (dd, J=8.4, 13.2 Hz, 1H), 2.14 (m, 2H), 1.39 (m, 1H), 1.09-1.03 (m, 8H). $^{13}$C NMR (CD$_3$OD, 100 MHz) δ 158.0, 132.7, 128.1, 127.3, 126.4, 113.8, 76.2, 45.1, 29.8, 19.8, 19.7, 19.1, 18.4, 13.8. HRMS (ESI) calcd for C$_{14}$H$_{20}$NOCl ([M+H]$^+$) 254.1306; found: 254.1316; [α]$_D^{20}$ −50.0 (c 0.15, CH$_3$OH).

(+)-(2-(5-Chloro-2-isobutoxyphenyl)cyclopropyl)methanamine (TFA salt). $^1$H NMR (CD$_3$OD, 400 MHz) δ 7.13 (dd, J=2.4, 8.8 Hz, 1H), 6.95 (d, J=2.4 Hz, 1H), 6.89 (d, J=8.8 Hz, 1H), 3.83-3.74 (m, 2H), 3.21 (dd, J=6.4, 12.8 Hz, 1H), 2.85 (dd, J=8.8, 12.8 Hz, 1H), 2.14 (m, 2H), 1.39 (m, 1H), 1.09-1.01 (m, 8H). $^{13}$C NMR (CD$_3$OD, 100 MHz) δ 158.0, 132.7, 128.1, 127.3, 126.4, 113.8, 76.2, 45.1, 29.8, 19.8, 19.7, 19.1, 18.4, 13.8. HRMS (ESI) calcd for C$_{14}$H$_{20}$NOCl ([M+H]$^+$) 254.1306; found: 254.1311; [α]$_D^{20}$ +55.4 (c 0.13, CH$_3$OH).

Example 16

(−)-(2-(5-Chloro-2-(isopentyloxy)phenyl)cyclopropyl)methanamine (TFA Salt)

(+)-(2-(5-Chloro-2-(isopentyloxy)phenyl)cyclopropyl)methanamine (TFA Salt)

Route 16:

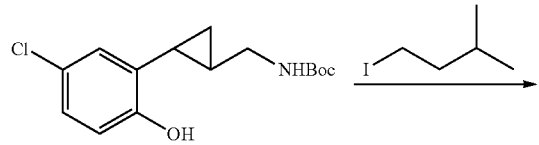

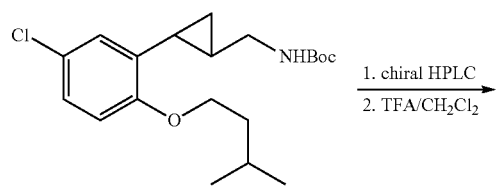

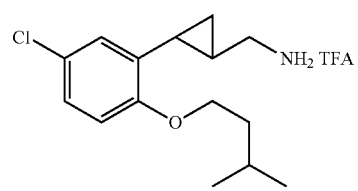

(−)-Example 16
(+)-Example 16

The title compounds were prepared via Route 16 using similar methods described above.

(−)-(2-(5-Chloro-2-(isopentyloxy)phenyl)cyclopropyl)methanamine (TFA salt). $^1$H NMR (CD$_3$OD, 400 MHz) δ 7.14 (dd, J=2.4, 8.8 Hz, 1H), 6.94 (d, J=2.4 Hz, 1H), 6.91 (d, J=8.8 Hz, 1H), 4.04 (m, 2H), 3.15 (dd, J=6.4, 13.2 Hz, 1H), 2.90 (dd, J=8.4, 12.8 Hz, 1H), 2.12 (m, 1H), 1.87 (m, 1H), 1.73 (m, 2H), 1.35 (m, 1H), 1.09-0.99 (m, 8H). $^{13}$C NMR (CD$_3$OD, 100 MHz) δ 158.0, 132.7, 128.1, 127.3, 126.4, 113.8, 68.3, 45.1, 39.3, 26.5, 23.2, 23.1, 19.3, 18.3, 13.7. HRMS (ESI) calcd for C$_{15}$H$_{22}$NOCl ([M+H]$^+$) 268.1463; found: 268.1473; [α]$_D^{20}$ −34.9 (c 0.3, CH$_3$OH).

(+)-(2-(5-Chloro-2-(isopentyloxy)phenyl)cyclopropyl)methanamine (TFA salt). $^1$H NMR (CD$_3$OD, 400 MHz) δ 7.14 (dd, J=2.4, 8.8 Hz, 1H), 6.94 (d, J=2.4 Hz, 1H), 6.91 (d, J=8.8 Hz, 1H), 4.04 (m, 2H), 3.15 (dd, J=6.4, 13.2 Hz, 1H), 2.90 (dd, J=8.4, 12.8 Hz, 1H), 2.12 (m, 1H), 1.87 (m, 1H), 1.73 (m, 2H), 1.36 (m, 1H), 1.08-0.99 (m, 8H). $^{13}$C NMR (CD$_3$OD, 100 MHz) δ 158.0, 132.7, 128.1, 127.3, 126.4, 113.8, 68.3, 45.1, 39.3, 26.5, 23.2, 23.1, 19.3, 18.3, 13.7. HRMS (ESI) calcd for C$_{15}$H$_{22}$NOCl ([M+H]$^+$) 268.1463; found: 268.1473; [α]$_D^{20}$ +45.5 (c 0.15, CH$_3$OH).

Example 17

(−)-(2-(5-Chloro-2-(2-methoxyethoxy)phenyl)cyclopropyl)methanamine (HCl Salt)

(+)-(2-(5-Chloro-2-(2-methoxyethoxy)phenyl)cyclopropyl)methanamine (HCl Salt)

Route 17:

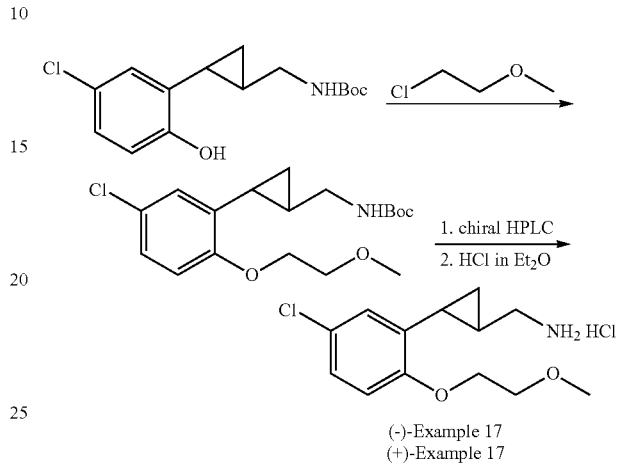

(−)-Example 17
(+)-Example 17

The title compounds were prepared via Route 17 using similar methods described above.

(−)-(2-(5-Chloro-2-(2-methoxyethoxy)phenyl)cyclopropyl)methanamine (HCl salt). $^1$H NMR (CD$_3$OD, 400 MHz) δ 7.26 (dd, J=2.6, 8.8 Hz, 1H), 7.06 (d, J=2.5 Hz, 1H), 7.01 (d, J=8.8 Hz, 1H), 4.27-4.22 (m, 2H), 3.91-3.85 (m, 2H), 3.46 (s, 3H), 3.23 (dd, J=6.8, 13.1 Hz, 1H), 2.98 (dd, J=8.2, 13.0 Hz, 1H), 2.13 (m, 1H), 1.30 (m, 1H), 1.20 (m, 1H), 1.06 (m, 1H); $^{13}$C NMR (CD$_3$OD, 100 MHz) δ 156.0, 132.1, 127.3, 126.6, 126.0, 114.1, 70.9, 68.1, 58.4, 44.0, 18.7, 16.6, 12.2; HRMS (ESI) calcd for C$_{13}$H$_{18}$NO$_2$Cl ([M+H]$^+$) 256.1099; found: 256.1095; [α]$_D^{20}$ −18.2 (c 0.23, CD$_3$OD).

(+)-(2-(5-Chloro-2-(2-methoxyethoxy)phenyl)cyclopropyl)methanamine (HCl salt). $^1$H NMR (CD$_3$OD, 400 MHz) δ 7.25 (dd, J=2.6, 8.7 Hz, 1H), 7.04 (d, J=2.4 Hz, 1H), 6.99 (d, J=8.8 Hz, 1H), 4.24-4.20 (m, 2H), 3.90-3.84 (m, 2H), 3.46 (s, 3H), 3.21 (dd, J=13.1, 6.8 Hz, 1H), 2.98 (dd, J=13.0, 8.1 Hz, 1H), 2.12 (m, 1H), 1.28 (m, 1H), 1.18 (m, 1H), 1.06 (m, 1H); $^{13}$C NMR (CD$_3$OD, 100 MHz) δ 156.0, 132.1, 127.3, 126.6, 126.0, 114.1, 70.9, 68.1, 58.4, 44.0, 18.7, 16.6, 12.2; HRMS (ESI) calcd for C$_{13}$H$_{18}$NO$_2$Cl ([M+H]$^+$) 256.1099; found: 256.1101; [α]$_D^{20}$ +11.7 (c 0.35, CD$_3$OD).

Example 18

(−)-(2-(5-Chloro-2-(2-(methylthio)ethoxy)phenyl)cyclopropyl)methanamine (HCl Salt)

(+)-(2-(5-Chloro-2-(2-(methylthio)ethoxy)phenyl)cyclopropyl)methanamine (HCl Salt)

Route 18:

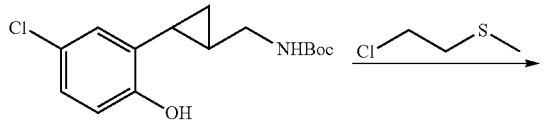

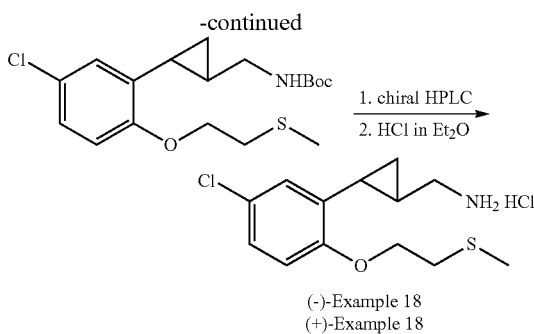

(-)-Example 18
(+)-Example 18

The title compounds were prepared via Route 18 using similar methods described above.

(−)-(2-(5-Chloro-2-(2-(methylthio)ethoxy)phenyl)cyclopropyl)methanamine (HCl salt). $^1$H NMR (400 MHz, CD$_3$OD) δ 7.16 (dd, J=8.8, 2.4 Hz, 1H), 6.97 (d, J=2.4 Hz, 1H), 6.94 (d, J=8.8 Hz, 1H), 4.25-4.20 (m, 2H), 3.14 (dd, J=12.8, 7.2 Hz, 2H), 2.98-2.92 (m, 3H), 2.20 (s, 3H), 2.17-2.11 (m, 1H), 1.33-1.28 (m, 1H), 1.18-1.12 (m, 1H), 1.07-1.02 (m, 1H); $^{13}$C NMR (100 MHz, CD$_3$OD) δ 157.6, 132.9, 128.2, 127.6, 127.0, 114.2, 68.9, 45.2, 34.4, 19.7, 18.3, 16.0, 13.3; HRMS calculated for [M+H]: 272.0870, found: 272.0874; $[\alpha]_D^{20}$ −41.6 (c 0.4, MeOH).

(+)-(2-(5-Chloro-2-(2-(methylthio)ethoxy)phenyl)cyclopropyl)methanamine (HCl salt). $^1$H NMR (400 MHz, CD$_3$OD) δ 7.16 (dd, J=8.8, 2.8 Hz, 1H), 6.96 (d, J=2.8 Hz, 1H), 6.94 (d, J=8.8 Hz, 1H), 4.25-4.20 (m, 2H), 3.14 (dd, J=12.8, 7.2 Hz, 2H), 2.98-2.92 (m, 3H), 2.20 (s, 3H), 2.17-2.11 (m, 1H), 1.33-1.27 (m, 1H), 1.18-1.12 (m, 1H), 1.07-1.03 (m, 1H); $^{13}$C NMR (100 MHz, CD$_3$OD) δ 157.6, 132.9, 128.2, 127.6, 127.0, 114.2, 68.9, 45.2, 34.4, 19.7, 18.3, 16.0, 13.3; HRMS calculated for [M+H]: 272.0870, found: 272.0870; $[\alpha]_D^{20}$ +44.9 (c 0.4, MeOH).

Example 19

(−)-(2-(5-Chloro-2-(2-fluoroethoxy)phenyl)cyclopropyl)methanamine (HCl Salt)

(+)-(2-(5-Chloro-2-(2-fluoroethoxy)phenyl)cyclopropyl)methanamine (HCl Salt)

Route 19:

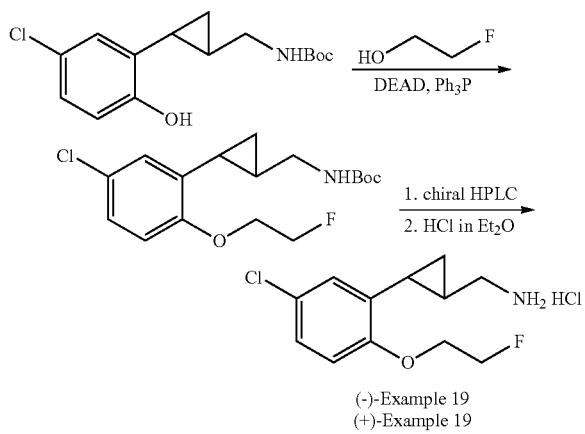

(-)-Example 19
(+)-Example 19

The title compounds were prepared via Route 19 using similar methods described above. Mitsunobu reaction using 2-fluoroethanol in the presence of triphenylphosphine and diethyl azodicarboxylate (DEAD) was applied for the first step.

(−)-(2-(5-Chloro-2-(2-fluoroethoxy)phenyl)cyclopropyl)methanamine (HCl salt). H NMR (400 MHz, D$_2$O) δ 7.10 (dd, J=9.7, 2.6 Hz, 1H), 6.91 (d, J=2.4 Hz, 1H), 6.84 (d, J=9.7 Hz, 1H), 4.84-4.81 (m, 1H), 4.68-4.66 (m, 1H), 4.26-4.15 (m, 2H), 3.04 (dd, J=14.5, 7.8 Hz, 1H), 2.92 (dd, J=14.4, 5.3 Hz, 1H), 2.01-1.98 (m, 1H), 1.18-1.15 (m, 1H), 1.09-1.04 (m, 1H), 0.96-0.91 (m, 1H); $^{13}$C NMR (100 MHz, D$_2$O) δ 155.8, 132.0, 127.3, 126.8, 126.2, 114.1, 83.3 (d, J$_{CF}$=180.8 Hz), 68.6 (d, J$_{CF}$=19.8 Hz), 43.9, 18.7, 16.6, 12.2; HRMS calculated for [M+H]: 244.0899, found: 244.0907; $[\alpha]_D^{20}$ −32.5 (c 0.1, MeOH).

(+)-(2-(5-Chloro-2-(2-fluoroethoxy)phenyl)cyclopropyl)methanamine (HCl salt). $^1$H NMR (400 MHz, CD$_3$OD) δ 7.18 (dd, J=8.8, 2.4 Hz, 1H), 7.01 (d, J=2.4 Hz, 1H), 6.95 (d, J=8.8 Hz), 4.80-4.74 (m, 2H), 4.34-4.27 (m, 2H), 3.05-3.00 (m, 2H), 2.15-2.11 (m, 1H), 1.27-1.17 (m, 2H), 1.06-1.02 (m, 1H); $^{13}$C NMR (100 MHz, D$_2$O) δ 155.8, 132.0, 127.3, 126.8, 126.2, 114.1, 83.2 (d, J$_{CF}$=180.8 Hz), 68.6 (d, J$_{CF}$=19.7 Hz), 43.9, 18.7, 16.5, 12.1; HRMS calculated for [M+H]: 244.0899, found: 244.0908; $[\alpha]_D^{20}$ +37.8 (c 0.5, MeOH).

Example 20

(−)-(2-(5-Chloro-2-(3-fluoropropoxy)phenyl)cyclopropyl)methanamine (HCl Salt)

(+)-(2-(5-Chloro-2-(3-fluoropropoxy)phenyl)cyclopropyl)methanamine (HCl Salt)

Route 20:

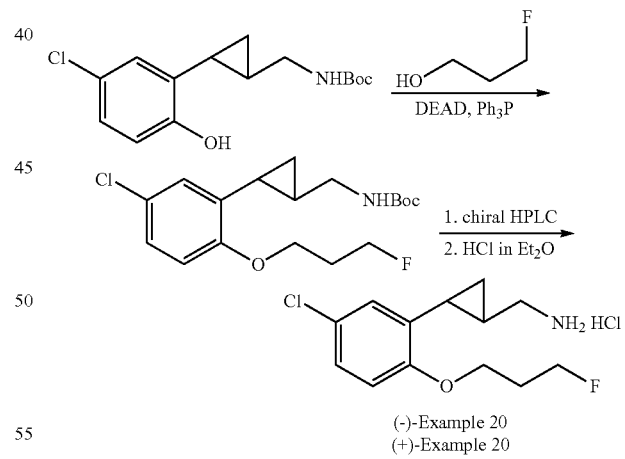

(-)-Example 20
(+)-Example 20

The title compounds were prepared via Route 20 using similar methods described for Example 19. 3-Fluoropropan-1-ol was used to replace 2-fluoroethanol.

(−)-(2-(5-Chloro-2-(3-fluoropropoxy)phenyl)cyclopropyl)methanamine (HCl salt). $^1$H NMR (400 MHz, D$_2$O) δ 7.25 (dd, J=8.8, 2.4 Hz, 1H), 7.04-7.01 (m, 2H), 4.78-4.76 (m, 1H), 4.69 (t, J=5.6 Hz, 1H), 4.27-4.21 (m, 2H), 3.17 (dd, J=13.2, 7.2 Hz, 1H), 3.03 (dd, J=13.2, 8.0 Hz, 1H), 2.30-2.15 (m, 3H), 1.42-1.38 (m, 1H), 1.14-1.05 (m, 2H); $^{13}$C NMR (100 MHz, D$_2$O) δ 155.5, 131.8, 126.9, 125.9, 125.6, 114.0, 82.3 ($J_{CF}$=157.8 Hz), 65.6 ($J_{CF}$=4.6 Hz), 43.6, 29.5 (d, $J_{CF}$=19.2 Hz), 18.1, 16.2, 12.5; HRMS calculated for [M+H]: 258.1055, found: 258.1056; $[\alpha]_D^{20}$ −51.4 (c 0.15, MeOH).

(+)-(2-(5-Chloro-2-(3-fluoropropoxy)phenyl)cyclopropyl)methanamine (HCl salt). $^1$H NMR (400 MHz, CD$_3$OD) δ 7.15 (dd, J=9.7, 2.9 Hz, 1H), 6.96 (d, J=2.8 Hz, 1H), 6.90 (d, J=9.8 Hz, 1H), 4.78-4.76 (m, 1H), 4.64 (t, J=6.4 Hz, 1H), 4.18-4.11 (m, 2H), 3.15 (dd, J=13.2, 7.2 Hz, 1H), 2.98 (dd, J=13.2, 8.0 Hz, 1H), 2.26-2.04 (m, 3H), 1.36-1.31 (m, 1H), 1.08-1.01 (m, 2H); $^{13}$C NMR (D$_2$O, 100 MHz) δ 155.9, 132.0, 127.2, 126.2, 125.9, 114.2, 82.7 ($J_{CF}$=175.4 Hz), 65.8 (d, $J_{CF}$=5.5 Hz), 43.9, 29.9 (d, $J_{CF}$=21.7 Hz), 18.4, 16.6, 12.8; HRMS calculated for [M+H]: 258.1055, found: 258.1064; $[\alpha]_D^{20}$ +44.2 (c 0.15, MeOH).

Example 21

(−)-(2-(5-Chloro-2-(2,2-difluoroethoxy)phenyl)cyclopropyl)methanamine (HCl Salt)

(+)-(2-(5-Chloro-2-(2,2-difluoroethoxy)phenyl)cyclopropyl)methanamine (HCl Salt)

Route 21:

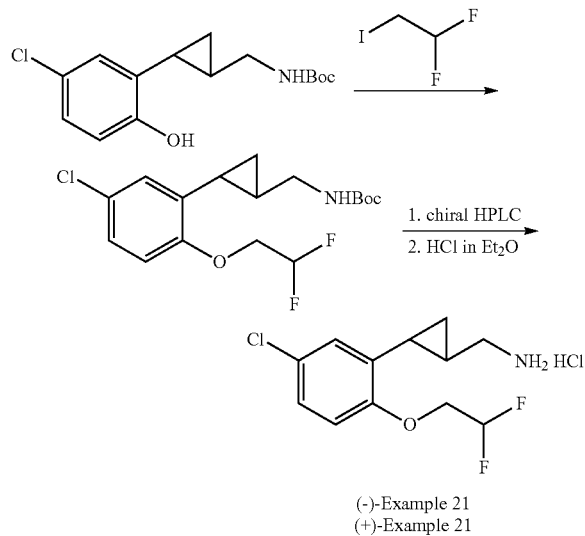

(−)-Example 21
(+)-Example 21

The title compounds were prepared via Route 21 using similar methods described above.

(−)-(2-(5-Chloro-2-(2,2-difluoroethoxy)phenyl)cyclopropyl)methanamine (HCl salt). $^1$H NMR (CD$_3$OD, 360 MHz) δ 7.15 (dd, J=8.7, 2.6 Hz, 1H), 6.98 (d, J=2.6 Hz, 1H), 6.93 (d, J=8.7 Hz, 1H), 6.24 (tt, J=54.8, 3.6 Hz, 1H), 4.27 (dt, J=14.2, 3.6 Hz, 2H), 3.09 (dd, J=13.1, 6.9 Hz, 1H), 2.90 (dd, J=13.1, 6.9 Hz, 1H), 2.12-2.09 (m, 1H), 1.32-1.28 (m, 1H), 1.13-1.09 (m, 1H), 1.05-1.01 (m, 1H); $^{13}$C NMR (CD$_3$OD, 90 MHz) δ 155.8, 131.9, 127.1, 126.7, 126.6, 114.3 (t, $J_{CF}$=238.0 Hz), 113.2, 67.7 (t, $J_{CF}$=27.3 Hz), 43.7, 18.3, 16.9, 12.1; HRMS (ESI): m/z [M+H]$^+$ calculated for C$_{12}$H$_{15}$ClF$_2$NO: 262.0810, found: 262.0830; $[\alpha]_D^{20}$ −34.2 (c 0.2, CD$_3$OD).

(+)-(2-(5-Chloro-2-(2,2-difluoroethoxy)phenyl)cyclopropyl)methanamine (HCl salt). $^1$H NMR (CD$_3$OD, 400 MHz) δ 7.18 (dd, J=2.6, 8.7 Hz, 1H), 7.02 (d, J=2.6 Hz, 1H), 6.96 (d, J=8.7 Hz, 1H), 6.27 (tt, J=54.8, 3.6 Hz, 1H), 4.30 (dt, J=14.2, 3.6 Hz, 2H), 3.12 (dd, J=13.1, 6.9 Hz, 1H), 2.93 (dd, J=13.1, 6.9 Hz, 1H), 2.17-2.11 (m, 1H), 1.34-1.32 (m, 1H), 1.18-1.13 (m, 1H), 1.08-1.03 (m, 1H); HRMS (ESI): m/z [M+H]$^+$ calculated for C$_{12}$H$_{15}$ClF$_2$NO: 262.0810, found: 262.0816; $[\alpha]_D^{20}$ +32.0 (c 0.25, CD$_3$OD).

Example 22

(−)-(2-(5-Chloro-2-(2,2,2-trifluoroethoxy)phenyl)cyclopropyl)methanamine (HCl Salt)

(+)-(2-(5-Chloro-2-(2,2,2-trifluoroethoxy)phenyl)cyclopropyl)methanamine (HCl Salt)

Route 22:

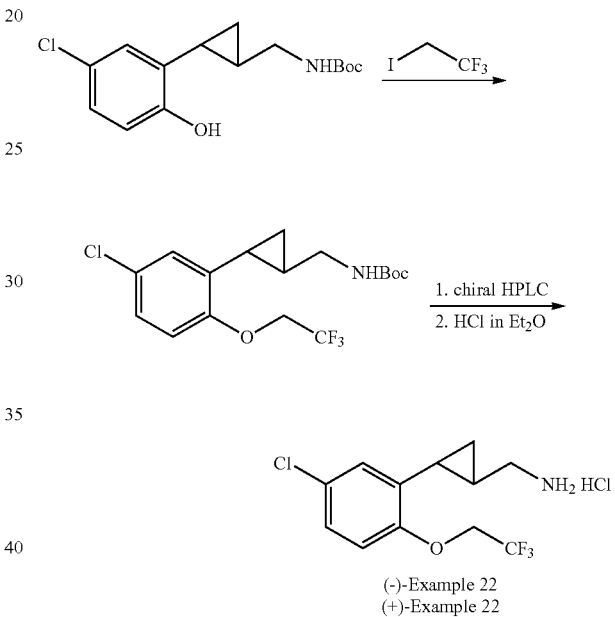

(−)-Example 22
(+)-Example 22

The title compounds were prepared via Route 22 using similar methods described above.

(−)-(2-(5-Chloro-2-(2,2,2-trifluoroethoxy)phenyl)cyclopropyl)methanamine (HCl salt). $^1$H NMR (400 MHz, CD$_3$OD) δ 7.21 (dd, J=8.8, 2.4 Hz, 1H), 7.05 (d, J=2.4 Hz, 1H), 7.01 (d, J=8.8 Hz, 1H), 4.61 (q, J=8.4 Hz, 2H), 3.21 (dd, J=13.2, 6.4 Hz, 1H), 2.86 (dd, J=12.6, 8.4 Hz, 1H), 2.15-2.10 (m, 1H), 1.41-1.35 (m, 1H), 1.15-1.05 (m, 2H); $^{13}$C NMR (100 MHz, CD$_3$OD) δ 156.5, 133.5, 128.6, 128.4, 128.1, 125.4 (q, $J_{CF}$=275.4 Hz), 115.0, 67.3 (q, $J_{CF}$=34.5 Hz), 44.9, 19.4, 18.2, 13.6; HRMS calculated for [M+H]: 280.0711, found: 280.0719; $[\alpha]_D^{20}$ −52.0 (c 0.5, MeOH).

(+)-(2-(5-Chloro-2-(2,2,2-trifluoroethoxy)phenyl)cyclopropyl)methanamine (HCl salt). $^1$H NMR (400 MHz, CD$_3$OD) δ 7.21 (dd, J=8.8, 2.8 Hz, 1H), 7.05 (d, J=2.4 Hz, 1H), 7.01 (d, J=8.8 Hz, 1H), 4.61 (q, J=8.4 Hz, 2H), 3.21 (dd, J=13.2, 6.4 Hz, 1H), 2.86 (dd, J=13.2, 8.6 Hz, 1H), 2.15-2.10 (m, 1H), 1.38-1.35 (m, 1H), 1.15-1.05 (m, 2H); $^{13}$C NMR (100 MHz, CD$_3$OD) δ 156.5, 133.5, 128.6, 128.4, 128.1, 125.4 (q, $J_{CF}$=275.4 Hz), 115.0, 67.3 (q, $J_{CF}$=35.4 Hz), 44.9, 19.4, 18.2, 13.6; HRMS calculated for [M+H]: 280.0711, found: 280.0712; $[\alpha]_D^{20}$ +46.3 (c 0.5, MeOH).

Example 23

(−)-(2-(2-(Allyloxy)-5-chlorophenyl)cyclopropyl)methanamine (TFA Salt)

(+)-(2-(2-(Allyloxy)-5-chlorophenyl)cyclopropyl)methanamine (TFA Salt)

Route 23:

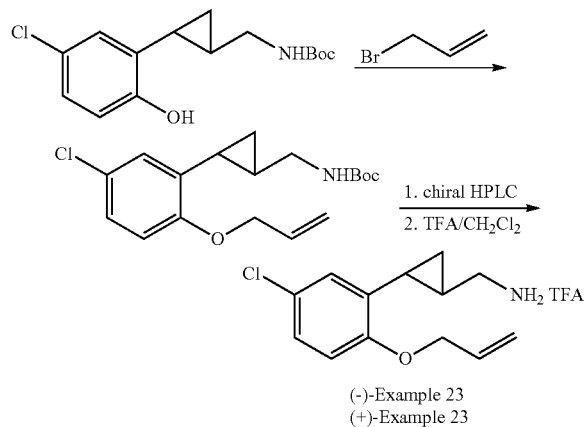

(−)-Example 23
(+)-Example 23

The title compounds were prepared via Route 23 using similar methods described above.

(−)-(2-(2-(Allyloxy)-5-chlorophenyl)cyclopropyl)methanamine (TFA salt). $^1$H NMR (CD$_3$OD, 400 MHz) δ 7.16 (dd, J=2.0, 8.8 Hz, 1H), 6.97 (s, 1H), 6.94 (d, J=8.8 Hz, 1H), 6.12 (m, 1H), 5.47 (d, J=17.2 Hz, 1H), 5.33 (d, J=10.8 Hz, 1H), 4.62 (d, J=5.2 Hz, 2H), 3.03 (m, 2H), 2.15 (m, 1H), 1.32 (m, 1H), 1.12-1.02 (m, 2H); $^{13}$C NMR (CD$_3$OD, 100 MHz) δ 157.5, 134.8, 132.8, 128.1, 127.6, 126.8, 118.4, 114.3, 70.6, 45.1, 19.4, 18.3, 13.5; HRMS (ESI) calcd for C$_{13}$H$_{16}$NOCl ([M+H]$^+$) 238.0993; found: 238.0994; $[α]_D^{20}$ −54.2 (c 0.27, CH$_3$OH).

(+)-(2-(2-(Allyloxy)-5-chlorophenyl)cyclopropyl)methanamine (TFA salt). $^1$H NMR (CD$_3$OD, 400 MHz) δ 7.15 (dd, J=2.0, 8.8 Hz, 1H), 6.97 (s, 1H), 6.93 (d, J=8.8 Hz, 1H), 6.12 (m, 1H), 5.47 (d, J=17.2 Hz, 1H), 5.33 (d, J=10.4 Hz, 1H), 4.62 (d, J=4.8 Hz, 2H), 3.03 (m, 2H), 2.15 (m, 1H), 1.33 (m, 1H), 1.14-1.01 (m, 2H); $^{13}$C NMR (CD$_3$OD, 100 MHz) δ 157.5, 134.8, 132.8, 128.1, 127.6, 126.8, 118.4, 114.3, 70.6, 45.1, 19.4, 18.3, 13.5; HRMS (ESI) calcd for C$_{13}$H$_{16}$NOCl ([M+H]$^+$) 238.0993; found: 238.0999; $[α]_D^{20}$ −54.2 (c 0.27, CH$_3$OH).

Example 24

(−)-(2-(5-Chloro-2-((2-methylallyl)oxy)phenyl)cyclopropyl)methanamine (HCl Salt)

(+)-(2-(5-Chloro-2-((2-methylallyl)oxy)phenyl)cyclopropyl)methanamine (HCl Salt)

Route 24:

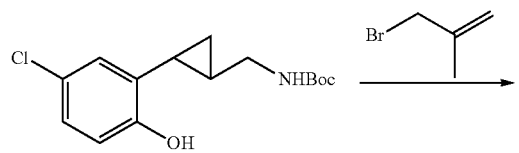

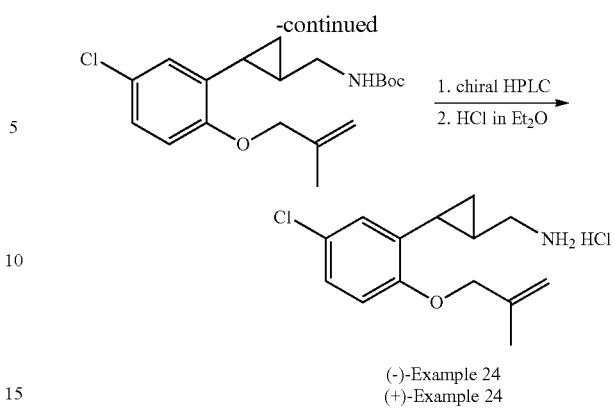

(−)-Example 24
(+)-Example 24

The title compounds were prepared via Route 24 using similar methods described above.

(−)-(2-(5-Chloro-2-((2-methylallyl)oxy)phenyl)cyclopropyl)methanamine (HCl salt). $^1$H NMR (CD$_3$OD, 360 MHz) δ: 7.11 (dd, J=2.6, 8.7 Hz, 1H), 6.94 (d, J=2.6 Hz, 1H), 6.88 (d, J=8.7 Hz, 1H), 5.08 (s, 1H), 4.98 (s, 1H), 4.49 (s, 2H), 3.08 (dd, J=13.0, 8.2 Hz, 1H), 2.28 (dd, J=13.0, 6.8 Hz, 1H), 2.16-2.12 (m, 1H), 1.83 (s, 3H), 1.70 (d, J=3.4 Hz, 1H), 1.36-1.33 (m, 1H), 1.09-1.02 (m, 1H); HRMS (ESI): m/z [M+H]$^+$ calculated for C$_{14}$H$_{19}$ClNO: 252.1155, found: 252.1162; $[α]_D^{20}$ −45.2 (c 0.21, CD$_3$OD).

(+)-(2-(5-Chloro-2-((2-methylallyl)oxy)phenyl)cyclopropyl)methanamine (HCl salt). $^1$H NMR (CD$_3$OD, 360 MHz) δ 7.09 (dd, J=8.7, 2.6 Hz, 1H), 6.96 (d, J=2.6 Hz, 1H), 6.85 (d, J=8.7 Hz, 1H), 5.07 (s, 1H), 4.97 (s, 1H), 4.48 (s, 2H), 3.07 (dd, J=13.0, 8.2 Hz, 1H), 2.87 (dd, J=13.0, 6.8 Hz, 1H), 2.16-2.11 (m, 1H), 1.82 (s, 3H), 1.68 (d, J=3.4 Hz, 1H), 1.36-1.32 (m, 1H), 1.08-1.00 (m, 1H); $^{13}$C NMR (CD$_3$OD, 100 MHz) δ 156.3, 141.3, 131.6, 127.0, 126.8, 126.5, 126.1, 125.5, 113.1, 113.0, 112.0, 77.2, 72.0, 43.8, 28.7, 28.6, 18.5, 18.0, 17.3, 17.1, 12.4, 12.2; HRMS (ESI): m/z [M+H]$^+$ calculated for C$_{14}$H$_{18}$ClNO: 252.1155, found: 252.1167; $[α]_D^{20}$ +43.6 (c 0.3, CD$_3$OD).

Example 25

(−)-(2-(5-Chloro-2-((2-fluoroallyl)oxy)phenyl)cyclopropyl)methanamine (HCl Salt)

(+)-(2-(5-Chloro-2-((2-fluoroallyl)oxy)phenyl)cyclopropyl)methanamine (HCl Salt)

Route 25:

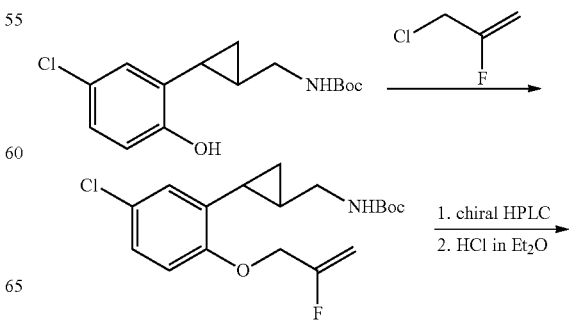

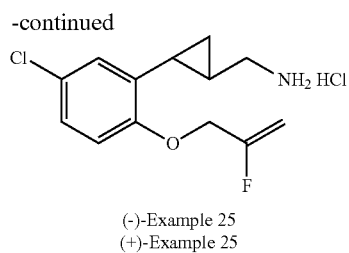

(−)-Example 25
(+)-Example 25

The title compounds were prepared via Route 25 using similar methods described above.

(−)-(2-(5-Chloro-2-((2-fluoroallyl)oxy)phenyl)cyclopropyl)methanamine (HCl salt). $^1$H NMR (DMSO-$d_6$, 400 MHz) δ 8.06 (br, 3H), 7.20 (dd, J=8.8, 2.4 Hz, 1H), 7.04 (d, J=8.8 Hz, 1H), 7.00 (d, J=2.8 Hz, 1H), 4.96 (dd, J=10.4, 3.2 Hz, 1H), 4.88 (dd, J=23.2, 3.2 Hz, 1H), 4.72 (d, J=14.0 Hz, 2H), 2.92-2.81 (m, 2H), 2.08-2.04 (m, 1H), 1.43-1.38 (m, 1H), 1.02-0.93 (m, 2H); HRMS (ESI): m/z calculated for $C_{13}H_{16}ClFNO$ [M+H]: 256.0904, found: 256.0914; $[\alpha]_D^{20}$ −40.7 (c 0.15, $CD_3OD$).

(+)-(2-(5-Chloro-2-((2-fluoroallyl)oxy)phenyl)cyclopropyl)methanamine (HCl salt). $^1$H NMR (DMSO-$d_6$, 400 MHz) δ 8.06 (br, 3H), 7.20 (dd, J=8.8, 2.4 Hz, 1H), 7.04 (d, J=8.8 Hz, 1H), 7.00 (d, J=2.8 Hz, 1H), 4.96 (dd, J=10.4, 3.2 Hz, 1H), 4.88 (dd, J=23.2, 3.2 Hz, 1H), 4.72 (d, J=14.0 Hz, 2H), 2.92-2.81 (m, 2H), 2.08-2.04 (m, 1H), 1.43-1.38 (m, 1H), 1.02-0.93 (m, 2H); $^{13}$C NMR (DMSO-$d_6$, 100 MHz) δ 160.7 (d, $J_{CF}$=255.7 Hz), 155.1, 132.4, 126.5, 126.2, 125.1, 114.1, 94.8 (d, $J_{CF}$=15.4 Hz), 65.7 (d, $J_{CF}$=32.3 Hz), 42.6, 17.8, 16.6, 13.4; HRMS (ESI): m/z calculated for $C_{13}H_{16}ClFNO$ [M+H]: 256.0904, found: 256.0906; $[\alpha]_D^{20}$ +43.0 (c 0.2, $CD_3OD$).

Example 26

(−)-(2-(5-Chloro-2-(prop-2-yn-1-yloxy)phenyl)cyclopropyl)methanamine (HCl Salt)

(+)-(2-(5-Chloro-2-(prop-2-yn-1-yloxy)phenyl)cyclopropyl)methanamine (HCl Salt)

Route 26:

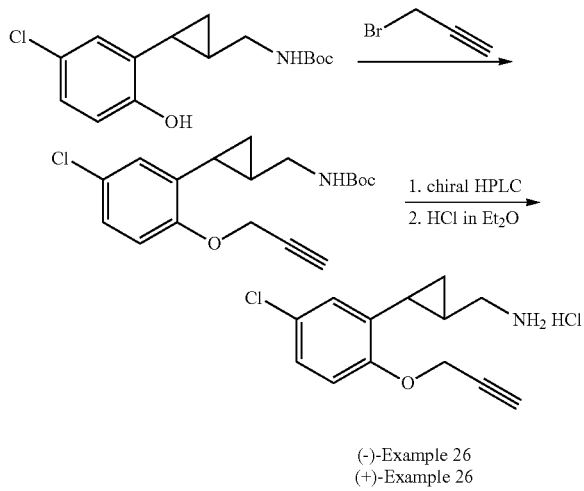

(−)-Example 26
(+)-Example 26

The title compounds were prepared via Route 26 using similar methods described above.

(−)-(2-(5-Chloro-2-(prop-2-yn-1-yloxy)phenyl)cyclopropyl)methanamine (HCl salt). $^1$H NMR ($CD_3OD$, 400 MHz) δ 7.16 (dd, J=8.8, 2.4 Hz, 1H), 7.03-6.99 (m, 2H), 4.82 (s, 2H), 3.09-3.05 (m, 2H), 2.99 (dd, J=12.8, 8.0 Hz, 1H), 2.13-2.08 (m, 1H), 1.30-1.27 (m, 1H), 1.15-1.13 (m, 1H), 1.05-1.02 (m, 1H); $^{13}$C NMR ($CD_3OD$, 100 MHz) δ 156.7, 133.1, 128.2, 128.0, 127.5, 114.6, 79.6, 77.6, 57.5, 45.1, 19.6, 18.1, 13.3; HRMS (ESI) calcd for $C_{13}H_{14}NOCl$ ([M+H]$^+$) 236.0837; found: 236.0842; $[\alpha]_D^{20}$ −32.7 (c 0.16, $CH_3OH$).

(+)-(2-(5-Chloro-2-(prop-2-yn-1-yloxy)phenyl)cyclopropyl)methanamine (HCl salt). $^1$H NMR ($CD_3OD$, 400 MHz) δ 7.16 (dd, J=8.8, 2.4 Hz, 1H), 7.03-6.99 (m, 2H), 4.81 (s, 2H), 3.09-3.04 (m, 2H), 2.99 (dd, J=13.2, 7.6 Hz, 1H), 2.13-2.08 (m, 1H), 1.31-1.27 (m, 1H), 1.16-1.12 (m, 1H), 1.06-1.02 (m, 1H); $^{13}$C NMR ($CD_3OD$, 100 MHz) δ 156.7, 133.1, 128.2, 128.0, 127.5, 114.6, 79.6, 77.6, 57.5, 45.1, 19.6, 18.1, 13.3; HRMS (ESI) calcd for $C_{13}H_{14}NOCl$ ([M+H]$^+$) 236.0837; found: 236.0840; $[\alpha]_D^{20}$ +47.3 (c 0.22, $CH_3OH$).

Example 27

(−)-(2-(5-Chloro-2-phenoxyphenyl)cyclopropyl)methanamine (HCl Salt)

(+)-(2-(5-Chloro-2-phenoxyphenyl)cyclopropyl)methanamine (HCl Salt)

Route 27:

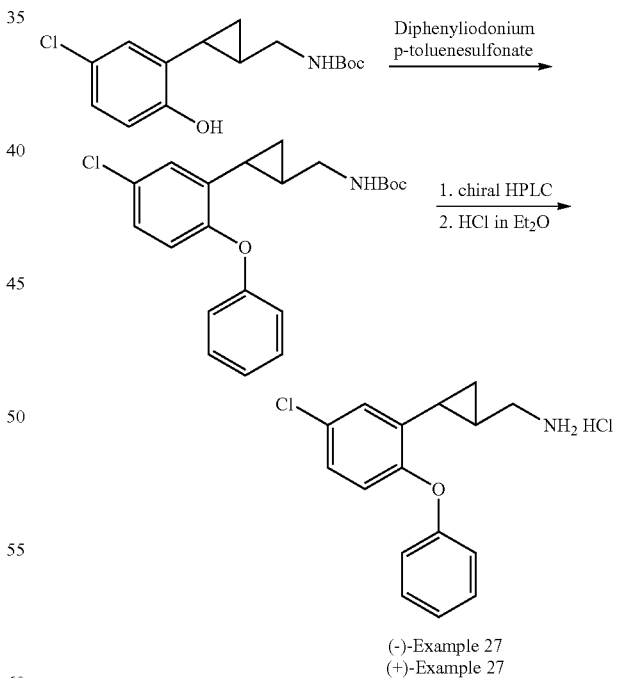

(−)-Example 27
(+)-Example 27

The title compounds were prepared via Route 27 using similar methods described above. The first step was conducted with diphenyliodonium p-toluenesulfonate (1.2 eq) in the presence of t-BuOK (1.1 eq) with THF as the solvent (for reference, see Jalalian, N. et al. *Org Lett* 2011, 13, 1552-1555.).

(−)-(2-(5-Chloro-2-phenoxyphenyl)cyclopropyl)methanamine (HCl salt). $^1$H NMR (CD$_3$OD, 360 MHz) δ: 7.34 (m, 1H), 7.19 (dd, J=2.6, 7.8 Hz, 1H), 7.08 (m, 2H), 6.90 (d, J=7.8 Hz, 2H), 6.84 (d, J=8.4 Hz, 1H), 2.84 (m, 1H), 2.68 (m, 1H), 2.08 (m, 1H), 1.31 (m, 1H), 1.15 (m, 1H), 0.96 (m, 1H); $^{13}$C NMR (CD$_3$OD, 100 MHz) δ: 157.9, 154.2, 134.8, 129.9, 129.3, 127.4, 126.6, 123.2, 120.9, 117.6, 43.4, 18.8, 17.0, 12.5; HRMS (ESI): m/z [M+H]$^+$ calculated for C$_{16}$H$_{17}$ClNO: 274.0999, found: 274.1025; [α]$_D^{20}$ −33.1 (c 0.13, CD$_3$OD).

(+)-(2-(5-Chloro-2-phenoxyphenyl)cyclopropyl)methanamine (HCl salt). $^1$H NMR (CD$_3$OD, 400 MHz) δ: 7.37 (m, 1H), 7.20 (dd, J=2.6, 7.8 Hz, 1H), 7.11 (m, 2H), 6.94 (d, J=7.8 Hz, 2H), 6.87 (d, J=8.4 Hz, 1H), 2.87 (m, 1H), 2.72 (m, 1H), 2.11 (m, 1H), 1.36 (m, 1H), 1.17 (m, 1H), 1.01 (m, 1H); HRMS (ESI): m/z [M+H]$^+$ calculated for C$_{16}$H$_{17}$ClNO: 274.0999, found: 274.0999; [α]$_D^{20}$ +30.5 (c 0.21, CD$_3$OD).

Example 28

(−)-(2-(2-(benzyloxy)-5-chlorophenyl)cyclopropyl)methanamine (HCl Salt)

(+)-(2-(2-(benzyloxy)-5-chlorophenyl)cyclopropyl)methanamine (HCl Salt)

Route 28:

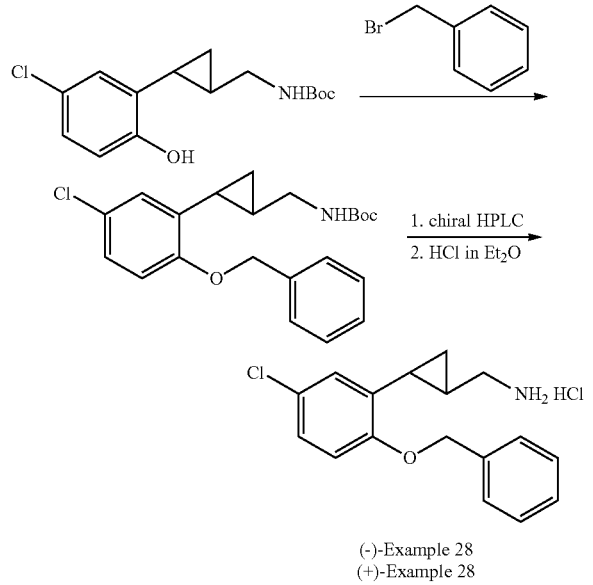

(−)-Example 28
(+)-Example 28

The title compounds were prepared via Route 28 using similar methods described above.

(−)-(2-(2-(Benzyloxy)-5-chlorophenyl)cyclopropyl)methanamine (HCl salt). $^1$H NMR (CD$_3$OD, 400 MHz) δ 7.49 (m, 2H), 7.38 (m, 3H), 7.15 (dd, J=2.5, 8.7 Hz, 1H), 6.98 (m, 2H), 5.12 (s, 2H), 3.00 (dd, J=7.2, 13.0 Hz, 1H), 2.90 (dd, J=7.9, 13.0 Hz, 1H), 2.12 (m, 1H), 1.31 (m, 1H), 1.12-1.00 (m, 2H). $^{13}$C NMR (CD$_3$OD, 100 MHz) δ 158.1, 138.8, 133.3, 130.2, 129.7, 129.4, 128.5, 128.1, 127.2, 114.8, 72.2, 45.4, 19.7, 18.7, 13.8. HRMS (ESI) calcd for C$_{17}$H$_{18}$NOCl ([M+H]$^+$) 288.1150; found: 288.1162; [α]$_D^{20}$ −18.1 (c 0.66, CH$_3$OH).

(+)-(2-(2-(Benzyloxy)-5-chlorophenyl)cyclopropyl)methanamine (HCl salt). $^1$H NMR (CD$_3$OD, 400 MHz) δ 7.49 (m, 2H), 7.38 (m, 3H), 7.15 (dd, J=2.5, 8.7 Hz, 1H), 6.98 (m, 2H), 5.12 (s, 2H), 3.00 (dd, J=7.2, 13.0 Hz, 1H), 2.90 (dd, J=7.9, 12.9 Hz, 1H), 2.13 (m, 1H), 1.32 (m, 1H), 1.12-1.01 (m, 2H). $^{13}$C NMR (CD$_3$OD, 100 MHz) δ 158.1, 138.8, 133.3, 130.2, 129.7, 129.4, 128.5, 128.1, 127.2, 114.8, 72.2, 45.4, 19.7, 18.7, 13.8. HRMS (ESI) calcd for C$_{17}$H$_{18}$NOCl ([M+H]$^+$) 288.1150; found: 288.1158; [α]$_D^{20}$ +17.5 (c 0.94, CH$_3$OH).

Example 29

(−)-(2-(3-chloro-2-fluoro-6-methoxyphenyl)cyclopropyl)methanamine (HCl Salt)

(+)-(2-(3-chloro-2-fluoro-6-methoxyphenyl)cyclopropyl)methanamine (HCl Salt)

Route 29:

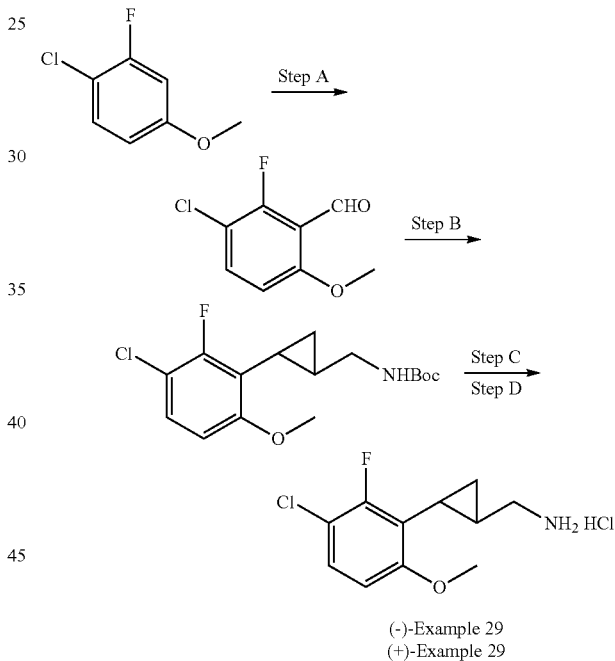

(−)-Example 29
(+)-Example 29

Step A: 3-Chloro-2-fluoro-6-methoxybenzaldehyde

Diisopropylamine (1.71 mL, 12 mmol) was dissolved in anhydrous THF (20 mL) and the solution was cooled to −78° C. under argon. A solution of n-BuLi (2.5 M, 6.0 mL, 12 mmol) was added slowly and the solution was stirred for 0.5 h. To this solution was added a solution of 1-chloro-2-fluoro-4-methoxybenzene (1.60 g, 10 mmol) in anhydrous THF (20 mL) and the mixture was stirred for another 20 min. Anhydrous DMF (2.0 mL) was then added slowly and the mixture was warmed to room temperature. Water was added and the mixture was extracted with ethyl acetate. The combined extracts were washed with brine, dried over sodium sulfate and concentrated to give the subtitle intermediate (1.9 g, 100%) as a yellow solid.

Step B: Tert-butyl ((2-(3-chloro-2-fluoro-6-methoxyphenyl)cyclopropyl)methyl)carbamate This intermediate was prepared from 3-chloro-2-fluoro-6-methoxybenzaldehyde with the same method as described in Example 1. $^1$H NMR (CDCl$_3$, 400 MHz) δ 7.18 (t, J=8.8 Hz, 1H), 6.58 (dd, J=8.8, 1.6 Hz, 1H), 5.30 (br, 1H), 3.87 (s, 3H), 3.58-3.54 (m, 1H), 2.76-2.68 (m, 1H), 1.53-1.44 (m, 10H), 1.24-1.17 (m, 2H), 0.92-0.87 (m, 1H).

Step C

Tert-butyl ((2-(3-chloro-2-fluoro-6-methoxyphenyl)cyclopropyl)methyl)carbamate was separated with chiral prep-HPLC to give (+)-tert-butyl ((2-(3-chloro-2-fluoro-6-methoxyphenyl)cyclopropyl)methyl)carbamate and (−)-tert-butyl ((2-(3-chloro-2-fluoro-6-methoxyphenyl)cyclopropyl)methyl)carbamate.

Step D (−)-(2-(3-Chloro-2-fluoro-6-methoxyphenyl)cyclopropyl)methanamine (HCl salt) and (+)-(2-(3-chloro-2-fluoro-6-methoxyphenyl)cyclopropyl)methanamine (HCl salt) was prepared from (+)-tert-butyl ((2-(3-chloro-2-fluoro-6-methoxyphenyl)cyclopropyl)methyl)carbamate and (−)-tert-butyl ((2-(3-chloro-2-fluoro-6-methoxyphenyl)cyclopropyl)methyl)carbamate respectively using HCl in Et$_2$O as described above.

(−)-(2-(3-Chloro-2-fluoro-6-methoxyphenyl)cyclopropyl)methanamine (HCl salt). $^1$H NMR (400 MHz, CD$_3$OD) δ 7.28 (t, J=8.8 Hz, 1H), 6.79 (dd, J=9.2, 1.6 Hz, 1H), 3.87 (s, 3H), 3.11 (dd, J=13.2, 6.8 Hz, 1H), 2.90 (dd, J=13.2, 8.0 Hz, 1H), 1.82-1.76 (m, 1H), 1.48-1.43 (m, 1H), 1.23-1.18 (m, 1H), 1.09-1.03 (m, 1H); $^{13}$C NMR (100 MHz, CD$_3$OD) δ 160.1 (d, J$_{CF}$=6.6 Hz), 158.7 (d, J$_{CF}$=243.8 Hz), 129.6, 118.9 (d, J$_{CF}$=20.1 Hz), 113.9 (d, J$_{CF}$=19.3 Hz), 108.5, 56.8, 45.4, 18.4, 13.7, 13.1; [α]$_D^{20}$ −54.0 (c 0.15, MeOH).

(+)-(2-(3-Chloro-2-fluoro-6-methoxyphenyl)cyclopropyl)methanamine (HCl salt). $^1$H NMR (400 MHz, CD$_3$OD) δ 7.29 (t, J=8.8 Hz, 1H), 6.79 (dd, J=8.8, 1.6 Hz, 1H), 3.88 (s, 3H), 3.11 (dd, J=12.8, 6.4 Hz, 1H), 2.90 (dd, J=12.8, 8.4 Hz, 1H), 1.82-1.77 (m, 1H), 1.48-1.44 (m, 1H), 1.24-1.18 (m, 1H), 1.09-1.04 (m, 1H); $^{13}$C NMR (100 MHz, CD$_3$OD) δ 160.1 (d, J$_{CF}$=6.6 Hz), 158.7 (d, J$_{CF}$=243.8 Hz), 129.6, 118.9 (d, J$_{CF}$=20.1 Hz), 113.8 (d, J$_{CF}$=19.3 Hz), 108.4, 56.8, 45.4, 18.4, 13.7, 13.0; [α]$_D^{20}$ +50.0 (c 0.1, MeOH).

Example 30

(−)-(2-(3-Chloro-6-ethoxy-2-fluorophenyl)cyclopropyl)methanamine (HCl Salt)

(+)-(2-(3-Chloro-6-ethoxy-2-fluorophenyl)cyclopropyl)methanamine (HCl Salt)

Route 30:

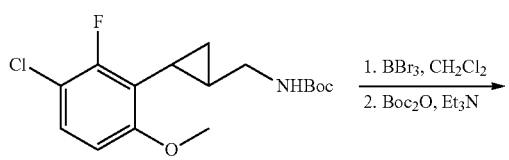

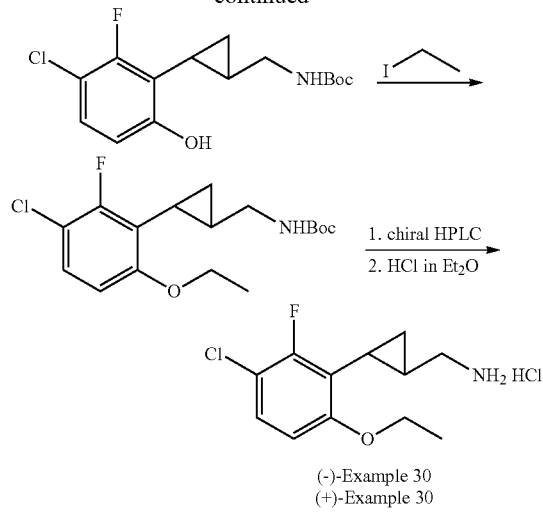

The title compounds were prepared via Route 30 using similar methods described above.

(−)-(2-(3-Chloro-6-ethoxy-2-fluorophenyl)cyclopropyl)methanamine (HCl salt). $^1$H NMR (400 MHz, CD$_3$OD) δ 7.26 (t, J=8.8 Hz, 1H), 6.77 (d, J=9.2 Hz, 1H), 4.12-4.06 (m, 2H), 3.08 (dd, J=12.8, 7.2 Hz, 1H), 2.97 (dd, J=13.2, 7.6 Hz, 1H), 1.86-1.81 (m, 1H), 1.58-1.53 (m, 1H), 1.45 (t, J=7.6 Hz, 3H), 1.27-1.24 (m, 1H), 1.09-1.05 (m, 1H); $^{13}$C NMR (100 MHz, CD$_3$OD) δ 159.4 (d, J$_{CF}$=6.4 Hz), 158.7 (d, J$_{CF}$=244.0 Hz), 129.4, 119.0 (d, J$_{CF}$=14.0 Hz), 113.6 (d, J$_{CF}$=19.3 Hz), 109.3, 65.8, 45.4, 18.3, 15.1, 14.0, 13.1; [α]$_D^{20}$ −52.7 (c 0.15, MeOH).

(+)-(2-(3-Chloro-6-ethoxy-2-fluorophenyl)cyclopropyl)methanamine (HCl salt). $^1$H NMR (400 MHz, CD$_3$OD) δ 7.26 (t, J=8.8 Hz, 1H), 6.77 (dd, J=8.8, 1.6 Hz, 1H), 4.13-4.06 (m, 2H), 3.09 (dd, J=13.2, 7.2 Hz, 1H), 2.97 (dd, J=13.2, 7.6 Hz, 1H), 1.85-1.81 (m, 1H), 1.58-1.55 (m, 1H), 1.46 (t, J=6.8 Hz, 3H), 1.28-1.23 (m, 1H), 1.10-1.06 (m, 1H); $^{13}$C NMR (100 MHz, CD$_3$OD) δ 159.4 (d, J$_{CF}$=6.4 Hz), 158.7 (d, J$_{CF}$=243.7 Hz), 129.4, 119.0 (d, J$_{CF}$=14.4 Hz), 113.6 (d, J$_{CF}$=19.3 Hz), 109.3, 65.9, 45.4, 18.3, 15.1, 14.0, 13.1; [α]$_D^{20}$ +58.2 (c 0.15, MeOH).

Example 31

(−)-(2-(3-Chloro-2-fluoro-6-(2-fluoroethoxy)phenyl)cyclopropyl)methanamine (HCl Salt)

(+)-(2-(3-Chloro-2-fluoro-6-(2-fluoroethoxy)phenyl)cyclopropyl)methanamine (HCl Salt)

Route 31:

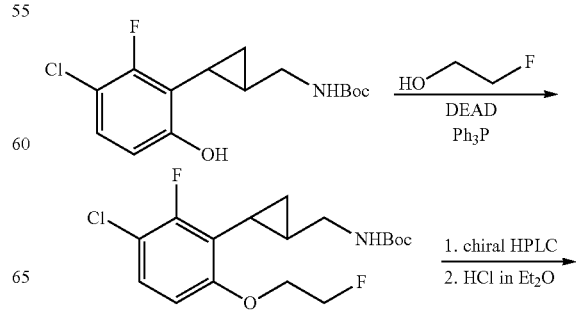

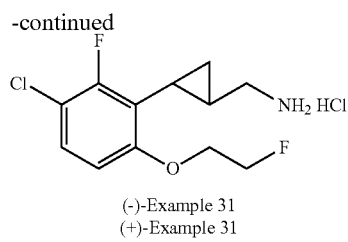

(−)-Example 31
(+)-Example 31

The title compounds were prepared via Route 31 using similar methods described above.

(−)-(2-(3-Chloro-2-fluoro-6-(2-fluoroethoxy)phenyl)cyclopropyl)methanamine (HCl salt). $^1$H NMR (400 MHz, CD$_3$OD) δ 7.29 (t, J=8.8 Hz, 1H), 6.81 (d, J=9.2 Hz, 1H), 4.88-4.83 (m, 1H), 4.77-4.75 (m, 1H), 4.35-4.21 (m, 2H), 3.09 (dd, J=13.2, 7.2 Hz, 1H), 2.98 (dd, J=13.2, 7.6 Hz, 1H), 1.88-1.83 (m, 1H), 1.55-1.51 (m, 1H), 1.32-1.28 (m, 1H), 1.12-1.06 (m, 1H); $^{13}$C NMR (100 MHz, CD$_3$OD) δ 159.0 (d, $J_{CF}$=6.4 Hz), 158.7 (d, $J_{CF}$=244.0 Hz), 129.5, 119.4 (d, $J_{CF}$=14.7 Hz), 114.4 (d, $J_{CF}$=19.2 Hz), 109.5, 83.3 (d, $J_{CF}$=167.4 Hz), 69.6 (d, $J_{CF}$=19.0 Hz), 45.3, 18.5, 13.9, 13.1; $[α]_D^{20}$ −53.0 (c 0.3, MeOH).

(+)-(2-(3-Chloro-2-fluoro-6-(2-fluoroethoxy)phenyl)cyclopropyl)methanamine (HCl salt). $^1$H NMR (400 MHz, CD$_3$OD) δ 7.29 (t, J=8.8 Hz, 1H), 6.81 (dd, J=8.8, 1.4 Hz, 1H), 4.88-4.83 (m, 1H), 4.77-4.74 (m, 1H), 4.33-4.23 (m, 2H), 3.10 (dd, J=12.8, 7.2 Hz, 1H), 2.98 (dd, J=13.2, 7.6 Hz, 1H), 1.88-1.83 (m, 1H), 1.55-1.51 (m, 1H), 1.32-1.28 (m, 1H), 1.12-1.06 (m, 1H); $^{13}$C NMR (100 MHz, CD$_3$OD) δ 159.0 (d, $J_{CF}$=6.5 Hz), 158.7 (d, $J_{CF}$=244.4 Hz), 129.5, 119.4 (d, $J_{CF}$=14.7 Hz), 114.4 (d, $J_{CF}$=19.3 Hz), 109.5, 83.3 (d, $J_{CF}$=167.3 Hz), 69.6 (d, $J_{CF}$=19.0 Hz), 45.3, 18.5, 13.9, 13.1; $[α]_D^{20}$ +53.5 (c 0.4, MeOH).

Example 32

(−)-(2-(6-(Allyloxy)-3-chloro-2-fluorophenyl)cyclopropyl)methanamine (HCl Salt)

(+)-(2-(6-(Allyloxy)-3-chloro-2-fluorophenyl)cyclopropyl)methanamine (HCl Salt)

Route 32:

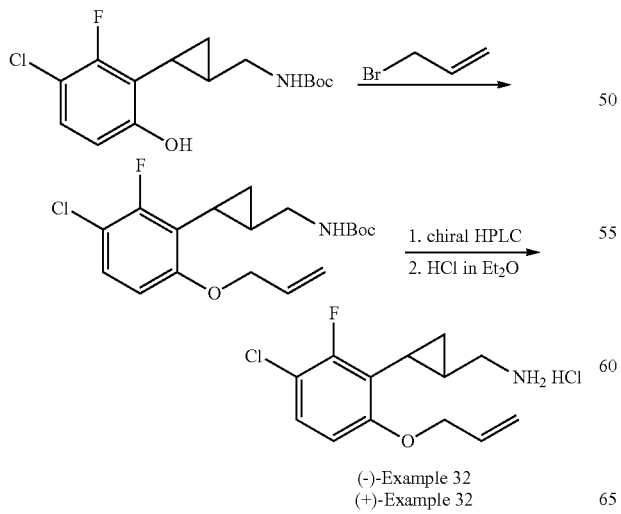

(−)-Example 32
(+)-Example 32

The title compounds were prepared via Route 32 using similar methods described above.

(−)-(2-(6-(Allyloxy)-3-chloro-2-fluorophenyl)cyclopropyl)methanamine (HCl salt). $^1$H NMR (400 MHz, CD$_3$OD) δ 7.26 (t, J=8.4 Hz, 1H), 6.79 (d, J=9.2 Hz, 1H), 6.17-6.07 (m, 1H), 5.46 (d, J=17.2 Hz, 1H), 5.33 (d, J=10.4 Hz, 1H), 4.61 (d, J=5.2 Hz, 2H), 3.08-2.97 (m, 2H), 1.88-1.83 (m, 1H), 1.59-1.52 (m, 1H), 1.28-1.22 (m, 1H), 1.11-1.06 (m, 1H); $^{13}$C NMR (100 MHz, CD$_3$OD) δ 159.0 (d, $J_{CF}$=6.4 Hz), 158.7 (d, $J_{CF}$=243.9 Hz), 134.4, 129.4, 119.2 (d, $J_{CF}$=14.6 Hz), 118.7, 113.9 (d, $J_{CF}$=19.3 Hz), 109.7, 70.9, 45.3, 18.4, 13.9, 13.1; $[α]_D^{20}$ −54.0 (c 0.3, MeOH).

(+)-(2-(6-(Allyloxy)-3-chloro-2-fluorophenyl)cyclopropyl)methanamine (HCl salt). $^1$H NMR (400 MHz, CD$_3$OD) δ 7.26 (t, J=8.6 Hz, 1H), 6.79 (dd, J=9.2, 1.6 Hz, 1H), 6.17-6.07 (m, 1H), 5.46 (dd, J=17.2, 1.4 Hz, 1H), 5.33 (dd, J=10.4, 1.2 Hz, 1H), 4.61 (d, J=5.6 Hz, 2H), 3.08-2.97 (m, 2H), 1.88-1.83 (m, 1H), 1.57-1.52 (m, 1H), 1.28-1.22 (m, 1H), 1.11-1.06 (m, 1H); $^{13}$C NMR (100 MHz, CD$_3$OD) δ 159.0 (d, $J_{CF}$=6.6 Hz), 158.7 (d, $J_{CF}$=243.8 Hz), 134.4, 129.4, 119.2 (d, $J_{CF}$=14.5 Hz), 118.7, 113.9 (d, $J_{CF}$=19.2 Hz), 109.7, 70.9, 45.3, 18.4, 13.9, 13.1; $[α]_D^{20}$ +55.0 (c 0.2, MeOH).

Example 33

(−)-(2-(4,5-Dichloro-2-methoxyphenyl)cyclopropyl)methanamine (HCl Salt)

(+)-(2-(4,5-Dichloro-2-methoxyphenyl)cyclopropyl)methanamine (HCl Salt)

Route 33:

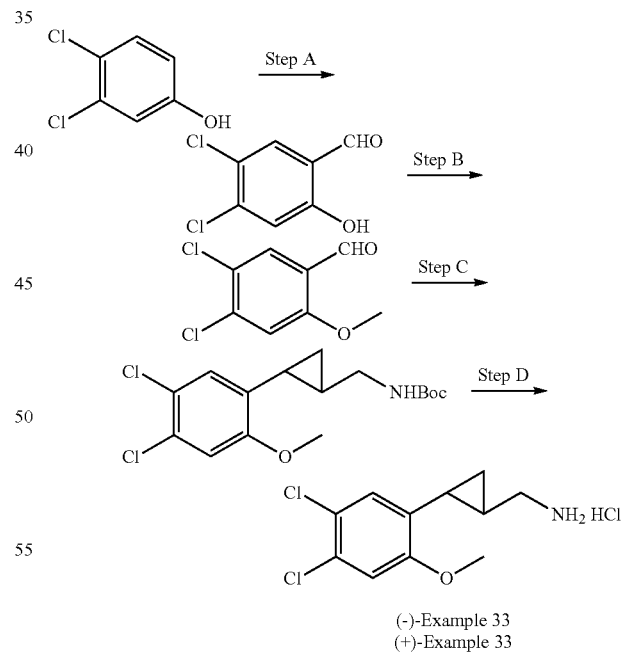

(−)-Example 33
(+)-Example 33

Step A: 4,5-Dichloro-2-hydroxybenzaldehyde 3,4-Dichlorophenol (20.0 g, 0.123 mol) was added to methylsulfonic acid (120 mL) and stirred for 15 min to give a clear solution. To this solution was added slowly hexamethylenetetramine (18.8 g, 0.134 mol) in small portions. The mixture was then heated to 105° C. and stirred for 15 min before being cooled to room temperature and poured into a mixture of ice and water (1.2 L). The mixture was extracted with DCM (200 mL*3) and the combined extracts were dried over sodium sulfate and concentrated to give the subtitle intermediate as a crude yellow solid (18.2 g, 77%).

Step B: 4,5-Dichloro-2-methoxybenzaldehyde

The crude product from Step A (18.2 g, 95 mmol) was dissolved in DMF (100 mL) and K$_2$CO$_3$ (26.2 g, 0.19 mol) and iodomethane (27.0 g, 0.19 mol) was added. The mixture was stirred at room temperature overnight. Water (500 mL) was then added and the mixture was extracted with ethyl acetate. The combined extracts were washed with brine, dried over sodium sulfate, concentrated and purified with flash chromatography to give the subtitle intermediate as a white solid (5.6 g, 22%). $^1$H NMR (CDCl$_3$, 400 MHz) 10.34 (s, 1H), 7.87 (s, 1H), 7.10 (s, 1H), 3.94 (s, 3H).

Step C: Tert-butyl ((2-(4,5-dichloro-2-methoxyphenyl)cyclopropyl)methyl)carbamate The subtitle compound was prepared from 4,5-dichloro-2-methoxybenzaldehyde using similar methods as described in Example 1. $^1$H NMR (CDCl$_3$, 400 MHz) 6.95 (s, 1H), 6.88 (s, 1H), 5.16 (br, 1H), 3.86 (s, 3H), 3.54-3.49 (m, 1H), 2.77-2.71 (m, 1H), 1.78-1.73 (m, 1H), 1.46 (s, 9H), 1.02-0.97 (m, 2H), 0.87-0.84 (m, 1H).

Step D: (−)-(2-(4,5-Dichloro-2-methoxyphenyl)cyclopropyl)methanamine (HCl Salt) and (+)-(2-(4,5-dichloro-2-methoxyphenyl)cyclopropyl)methanamine (HCl Salt)

Tert-butyl ((2-(4,5-dichloro-2-methoxyphenyl)cyclopropyl)methyl)carbamate was separated using chiral HPLC to provide (+)-tert-butyl ((2-(4,5-dichloro-2-methoxyphenyl)cyclopropyl)methyl)carbamate and (−)-tert-butyl ((2-(4,5-dichloro-2-methoxyphenyl)cyclopropyl)methyl)carbamate, which were treated with 2M HCl in diethyl ether as described above to give (−)-(2-(4,5-dichloro-2-methoxyphenyl)cyclopropyl)methanamine (HCl salt) and (+)-(2-(4,5-dichloro-2-methoxyphenyl)cyclopropyl)methanamine (HCl salt) respectively.

(−)-(2-(4,5-Dichloro-2-methoxyphenyl)cyclopropyl)methanamine (HCl salt). $^1$H NMR (400 MHz, CD$_3$OD) δ 7.11 (s, 2H), 3.88 (s, 3H), 3.08 (dd, J=13.2, 7.2 Hz, 1H), 2.92 (dd, J=13.2, 8.0 Hz, 1H), 2.09-2.04 (m, 1H), 1.28-1.26 (m, 1H), 1.16-1.10 (m, 1H), 1.06-1.00 (m, 1H); $^{13}$C NMR (100 MHz, CD$_3$OD) δ 159.1, 131.6, 131.5 129.2, 124.5, 113.7, 56.8, 45.0, 19.5, 17.8, 13.2; [α]$_D$$^{20}$ −37.4 (c 0.3, MeOH).

(+)-(2-(4,5-Dichloro-2-methoxyphenyl)cyclopropyl)methanamine (HCl salt). $^1$H NMR (400 MHz, CD$_3$OD) δ 7.11 (s, 2H), 3.89 (s, 3H), 3.08 (dd, J=13.2, 7.6 Hz, 1H), 2.93 (dd, J=12.8, 8.0 Hz, 1H), 2.09-2.04 (m, 1H), 1.29-1.26 (m, 1H), 1.15-1.10 (m, 1H), 1.06-1.02 (m, 1H); $^{13}$C NMR (100 MHz, CD$_3$OD) δ 159.1, 131.6, 131.5, 129.2, 124.5, 113.7, 56.8, 45.0, 19.5, 17.8, 13.2; [α]$_D$$^{20}$ +37.7 (c 0.4, MeOH).

Example 34

(−)-(2-(4,5-Dichloro-2-(2-fluoroethoxy)phenyl)cyclopropyl)methanamine (HCl Salt)

(+)-(2-(4,5-Dichloro-2-(2-fluoroethoxy)phenyl)cyclopropyl)methanamine (HCl Salt)

Route 34:

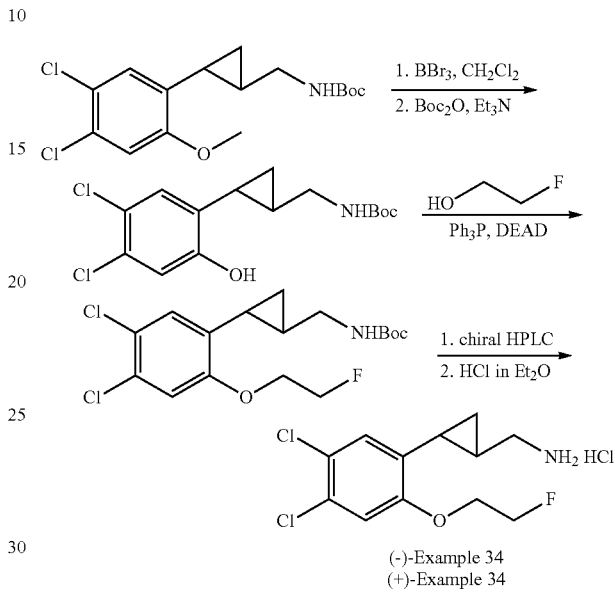

(−)-Example 34
(+)-Example 34

The title compounds were prepared via Route 34 using similar methods described above.

(−)-(2-(4,5-Dichloro-2-(2-fluoroethoxy)phenyl)cyclopropyl)methanamine (HCl salt). $^1$H NMR (400 MHz, CD$_3$OD) δ 7.16 (s, 1H), 7.15 (s, 1H), 4.88-4.75 (m, 2H), 4.36-4.24 (m, 2H), 3.04-3.01 (m, 2H), 2.13-2.08 (m, 1H), 1.29-1.26 (m, 1H), 1.23-1.19 (m, 1H), 1.08-1.03 (m, 1H); $^{13}$C NMR (100 MHz, CD$_3$OD) δ 158.1, 131.9, 131.6, 129.5, 125.1, 114.8, 83.3 (d, J$_{CF}$=167.1 Hz), 69.7 (d, J$_{CF}$=18.9 Hz), 44.9, 19.7, 17.9, 12.9; [α]$_D$$^{20}$ −32.4 (c 0.5, MeOH).

(+)-(2-(4,5-Dichloro-2-(2-fluoroethoxy)phenyl)cyclopropyl)methanamine (HCl salt). $^1$H NMR (400 MHz, CD$_3$OD) δ 7.16 (s, 1H), 7.15 (s, 1H), 4.88-4.75 (m, 2H), 4.36-4.24 (m, 2H), 3.04-3.01 (m, 2H), 2.13-2.08 (m, 1H), 1.29-1.26 (m, 1H), 1.23-1.19 (m, 1H), 1.08-1.03 (m, 1H); $^{13}$C NMR (100 MHz, CD$_3$OD) δ 158.1, 131.9, 131.6, 129.5, 125.1, 114.8, 83.3 (d, J$_{CF}$=167.1 Hz), 69.7 (d, J$_{CF}$=18.9 Hz), 44.9, 19.7, 17.9, 12.9; [α]$_D$$^{20}$ +30.2 (c 0.5, MeOH).

Example 35

(−)-(2-(2-(Allyloxy)-4,5-dichlorophenyl)cyclopropyl)methanamine (HCl Salt)

(+)-(2-(2-(Allyloxy)-4,5-dichlorophenyl)cyclopropyl)methanamine (HCl Salt)

Route 35:

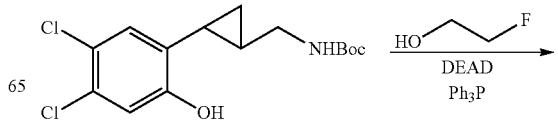

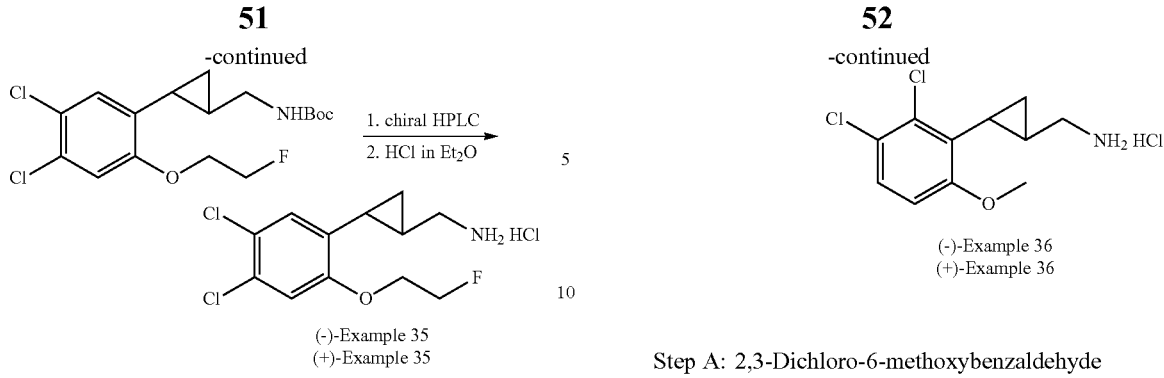

(−)-Example 35
(+)-Example 35

The title compounds were prepared via Route 35 using similar methods described above.

(−)-(2-(2-(Allyloxy)-4,5-dichlorophenyl)cyclopropyl)methanamine (HCl salt). ¹H NMR (400 MHz, CD₃OD) δ 7.12 (s, 1H), 7.10 (s, 1H), 6.17-6.07 (m, 1H), 5.47 (dd, J=17.6, 1.6 Hz, 1H), 5.34 (dd, J=10.4, 1.6 Hz, 1H), 4.63 (d, J=5.2 Hz, 2H), 3.08-2.97 (m, 2H), 2.14-2.09 (m, 1H), 1.37-1.32 (m, 1H), 1.15-1.03 (m, 2H); ¹³C NMR (100 MHz, CD₃OD) δ 157.9, 134.3, 131.9, 131.4, 129.2, 124.7, 118.7, 115.0, 70.9, 44.9, 19.4, 17.9, 13.5; [α]$_D^{20}$ −35.0 (c 0.4, MeOH).

(+)-(2-(2-(Allyloxy)-4,5-dichlorophenyl)cyclopropyl)methanamine (HCl salt). ¹H NMR (400 MHz, CD₃OD) δ 7.12 (s, 1H), 7.10 (s, 1H), 6.17-6.07 (m, 1H), 5.47 (dd, J=17.2, 1.2 Hz, 1H), 5.34 (d, J=10.4 Hz, 1H), 4.63 (d, J=5.2 Hz, 2H), 3.08-2.96 (m, 2H), 2.14-2.09 (m, 1H), 1.39-1.32 (m, 1H), 1.15-1.03 (m, 2H); ¹³C NMR (100 MHz, CD₃OD) δ 157.9, 134.3, 131.9, 131.4, 129.2, 124.7, 118.7, 115.0, 70.9, 44.9, 19.4, 17.9, 13.5; [α]$_D^{20}$ +37.6 (c 0.3, MeOH).

Example 36

(−)-(2-(2,3-Dichloro-6-methoxyphenyl)cyclopropyl)methanamine (HCl Salt)

(+)-(2-(2,3-Dichloro-6-methoxyphenyl)cyclopropyl)methanamine (HCl Salt)

Route 36:

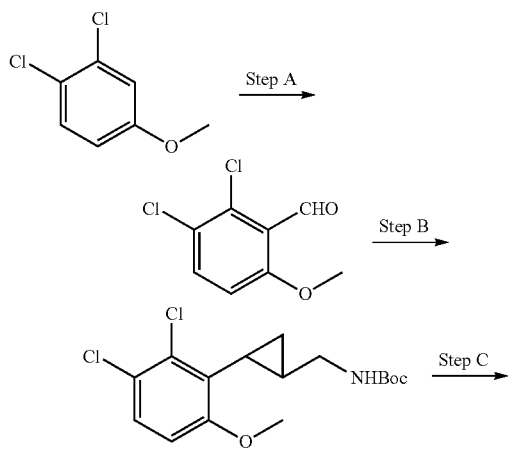

(−)-Example 36
(+)-Example 36

Step A: 2,3-Dichloro-6-methoxybenzaldehyde

A solution of 1,2-dichloro-4-methoxybenzene (12.5 g, 70.6 mmol) in anhydrous THF (100 mL) was cooled −78° C. under argon. To this solution was added n-BuLi (2.5 M in hexane, 31 mL, 77.7 mmol) slowly and the mixture was stirred for 0.5 h at the same temperature before DMF (6.0 mL, 77.7 mmol) was added via syringe. The mixture was stirred at the same temperature for 15 min and then warmed slowly to room temperature. Water was added and the mixture was extracted with ethyl acetate. The combined extracts were concentrated and recrystallized form ethyl acetate/hexane to give the subtitle compound (7.5 g, 52%) as a light yellow solid. ¹H NMR (CDCl₃, 400 MHz) 10.46 (s, 1H), 7.58 (d, J=8.0 Hz, 1H), 6.90 (d, J=12.0 Hz, 1H), 3.92 (s, 3H).

Step B: Tert-butyl ((2-(2,3-dichloro-6-methoxyphenyl)cyclopropyl)methyl)carbamate The subtitle compound was prepared from 2,3-dichloro-6-methoxybenzaldehyde using similar methods described in Example 1. ¹H NMR (CDCl₃, 400 MHz) 7.28 (d, J=9.2 Hz, 1H), 6.71 (d, J=8.8 Hz, 1H), 5.20 (br, 1H), 3.85 (s, 3H), 3.52-3.47 (dd, J=12.0, 8.8 Hz, 1H), 2.90 (dd, J=12.0, 9.2 Hz, 1H), 1.55-1.45 (m, 10H), 1.27-1.21 (m, 1H), 1.02-0.95 (m, 2H).

Step C

The racemic form of tert-butyl ((2-(2,3-dichloro-6-methoxyphenyl)cyclopropyl)methyl)carbamate was separated with chiral HPLC to provide (−)-tert-butyl ((2-(2,3-dichloro-6-methoxyphenyl)cyclopropyl)methyl)carbamate and (+)-tert-butyl ((2-(2,3-dichloro-6-methoxyphenyl)cyclopropyl)methyl)carbamate, which were subsequently treated with 2M HCl in ether to give (−)-(2-(2,3-dichloro-6-methoxyphenyl)cyclopropyl)methanamine (HCl salt) and (+)-(2-(2,3-dichloro-6-methoxyphenyl)cyclopropyl)methanamine (HCl salt).

(−)-(2-(2,3-Dichloro-6-methoxyphenyl)cyclopropyl)methanamine (HCl salt). ¹H NMR (400 MHz, CD₃OD) δ 7.40 (d, J=8.8 Hz, 1H), 6.96 (d, J=8.8 Hz, 1H), 3.88 (s, 3H), 3.06 (d, J=7.2 Hz, 2H), 1.78-1.73 (m, 1H), 1.44-1.40 (m, 1H), 1.21-1.15 (m, 1H), 1.11-1.06 (m, 1H); ¹³C NMR (100 MHz, CD₃OD) δ 159.9, 135.9, 130.2, 129.6, 125.7, 111.7, 56.7, 45.4, 20.1, 18.3, 15.2; [α]$_D^{20}$ −62.0 (c 0.1, MeOH).

(+)-(2-(2,3-Dichloro-6-methoxyphenyl)cyclopropyl)methanamine (HCl salt). ¹H NMR (400 MHz, CD₃OD) δ 7.40 (d, J=9.2 Hz, 1H), 6.96 (d, J=9.2 Hz, 1H), 3.88 (s, 3H), 3.06 (d, J=7.2 Hz, 2H), 1.77-1.74 (m, 1H), 1.44-1.42 (m, 1H), 1.21-1.15 (m, 1H), 1.09-1.05 (m, 1H); ¹³C NMR (100 MHz, CD₃OD) δ 159.9, 135.9, 130.2, 129.6, 125.7, 111.7, 56.7, 45.4, 20.1, 18.3, 15.2; [α]$_D^{20}$ +69.0 (c 0.2, MeOH).

Example 37

(−)-(2-(2,3-Dichloro-6-ethoxyphenyl)cyclopropyl)methanamine (HCl Salt)

(+)-(2-(2,3-Dichloro-6-ethoxyphenyl)cyclopropyl)methanamine (HCl Salt)

Route 37:

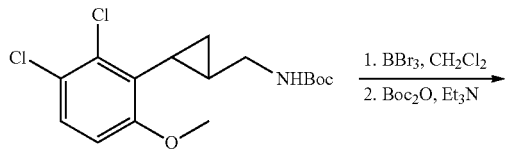

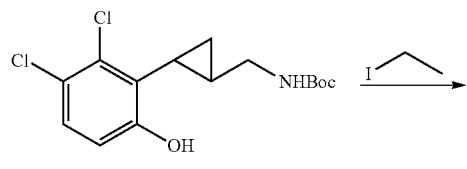

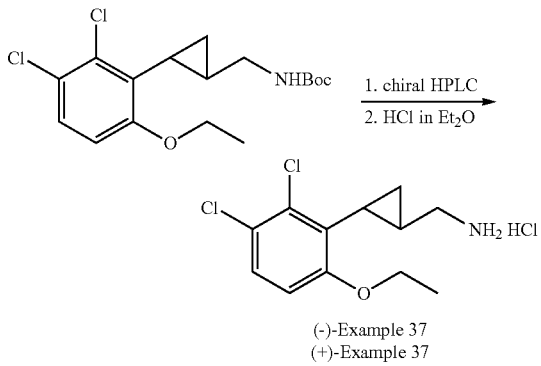

(−)-Example 37
(+)-Example 37

The title compounds were prepared via Route 37 using similar methods as described above.

(−)-(2-(2,3-Dichloro-6-ethoxyphenyl)cyclopropyl)methanamine (HCl salt). H NMR (400 MHz, CD$_3$OD) δ 7.36 (d, J=8.8 Hz, 1H), 6.92 (d, J=9.2 Hz, 1H), 4.14-4.03 (m, 2H), 3.35 (dd, J=13.2, 6.0 Hz, 1H), 2.82 (dd, J=13.2, 8.8 Hz, 1H), 1.79-1.75 (m, 1H), 1.50-1.45 (m, 4H), 1.20-1.13 (m, 2H); $^{13}$C NMR (100 MHz, CD$_3$OD) δ 159.2, 135.8, 130.0, 129.6, 125.4, 112.7, 65.7, 45.4, 20.2, 18.6, 15.3, 15.2; [α]$_D^{20}$ −62.0 (c 0.2, MeOH).

(+)-(2-(2,3-Dichloro-6-ethoxyphenyl)cyclopropyl)methanamine (HCl salt). $^1$H NMR (400 MHz, CD$_3$OD) δ 7.36 (d, J=8.8 Hz, 1H), 6.92 (d, J=8.8 Hz, 1H), 4.14-4.06 (m, 2H), 3.36 (dd, J=13.2, 6.0 Hz, 1H), 2.83 (dd, J=13.2, 8.8 Hz, 1H), 1.80-1.76 (m, 1H), 1.52-1.46 (m, 4H), 1.22-1.14 (m, 2H); $^{13}$C NMR (100 MHz, CD$_3$OD) δ 159.2, 135.8, 130.0, 129.7, 125.5, 112.7, 65.8, 45.4, 20.2, 18.6, 15.3, 15.2; [α]$_D^{20}$ +48.8 (c 0.4, MeOH).

Example 38

(−)-(2-(2,3-Dichloro-6-(2-fluoroethoxy)phenyl)cyclopropyl)methanamine (HCl Salt)

(+)-(2-(2,3-Dichloro-6-(2-fluoroethoxy)phenyl)cyclopropyl)methanamine (HCl Salt)

Route 38:

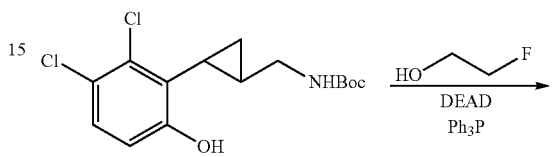

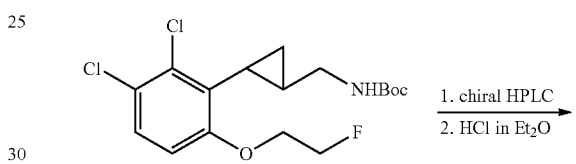

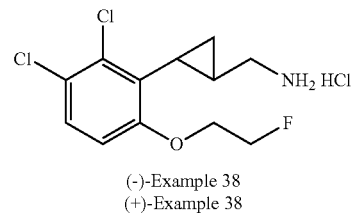

(−)-Example 38
(+)-Example 38

The title compounds were prepared via Route 38 using similar methods described above.

(−)-(2-(2,3-Dichloro-6-(2-fluoroethoxy)phenyl)cyclopropyl)methanamine (HCl salt). $^1$H NMR (400 MHz, DMSO-d$_6$) δ 8.09 (br, 3H), 7.48 (d, J=8.8 Hz, 1H), 7.03 (d, J=8.8 Hz, 1H), 4.90-4.73 (m, 2H), 4.32-4.22 (m, 2H), 3.26-3.22 (m, 1H), 2.64-2.59 (m, 1H), 1.78-1.73 (m, 1H), 1.45-1.41 (m, 1H), 1.18-1.12 (m, 1H), 1.04-1.00 (m, 1H); $^{13}$C NMR (100 MHz, DMSO-d$_6$) δ 157.1, 133.8, 128.8, 128.6, 123.5, 112.4, 82.2 (d, J$_{CF}$=165.6 Hz), 68.1 (d, J$_{CF}$=18.6 Hz), 42.7, 18.7, 16.9, 14.0; [°]D$^{20}$ −96.0 (c 0.1, MeOH).

(+)-(2-(2,3-Dichloro-6-(2-fluoroethoxy)phenyl)cyclopropyl)methanamine (HCl salt). $^1$H NMR (400 MHz, DMSO-d$_6$) δ 8.11 (br, 3H), 7.47 (d, J=8.8 Hz, 1H), 7.03 (d, J=8.8 Hz, 1H), 4.89-4.73 (m, 2H), 4.32-4.22 (m, 2H), 3.24 (dd, J=12.4, 5.2 Hz, 1H), 2.64-2.59 (m, 1H), 1.78-1.73 (m, 1H), 1.45-1.41 (m, 1H), 1.18-1.13 (m, 1H), 1.04-1.00 (m, 1H); $^{13}$C NMR (100 MHz, DMSO-d$_6$) δ 157.0, 133.7, 128.8, 128.6, 123.5, 112.4, 82.2 (d, J$_{CF}$=165.6 Hz), 68.1 (d, J$_{CF}$=18.6 Hz), 42.7, 18.6, 16.9, 13.9; [α]$_D^{20}$ +70.0 (c 0.1, MeOH).

Example 39

(−)-6-(Allyloxy)-2,3-dichlorophenyl)cyclopropyl)
methanamine (HCl Salt)

(+)-6-(Allyloxy)-2,3-dichlorophenyl)cyclopropyl)
methanamine (HCl Salt)

Route 39:

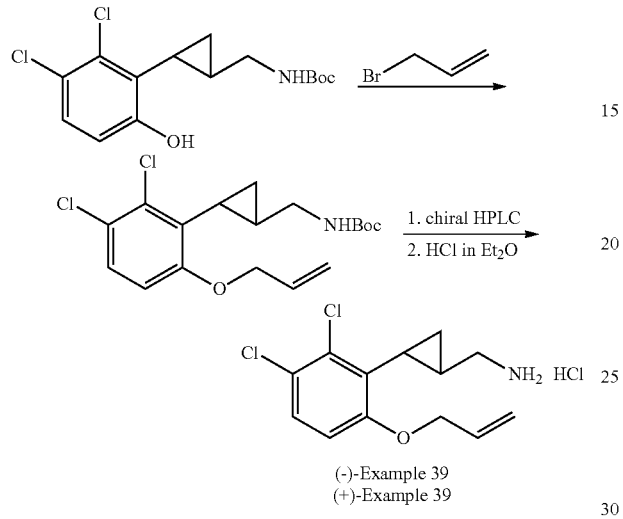

(−)-Example 39
(+)-Example 39

The title compounds were prepared via Route 39 using similar methods described above.

(−)-6-(Allyloxy)-2,3-dichlorophenyl)cyclopropyl)methanamine (HCl salt). $^1$H NMR (400 MHz, CD$_3$OD) δ 7.37 (d, J=9.2 Hz, 1H), 6.94 (d, J=9.2 Hz, 1H), 6.18-6.08 (m, 1H), 5.46 (dd, J=17.2, 1.6 Hz, 1H), 5.34 (dd, J=10.8, 1.2 Hz, 1H), 4.62 (d, J=5.2 Hz, 2H), 3.30 (dd, J=13.2, 8.8 Hz, 1H), 2.86 (dd, J=13.2, 8.8 Hz, 1H), 1.83-1.77 (m, 1H), 1.48-1.45 (m, 1H), 1.23-1.12 (m, 2H); $^{13}$C NMR (100 MHz, CD$_3$OD) δ 158.8, 135.9, 134.4, 130.0, 129.9, 125.8, 118.9, 113.3, 70.9, 45.3, 20.2, 18.5, 15.3; $[α]_D^{20}$ −68.0 (c 0.1, MeOH).

(+)-6-(Allyloxy)-2,3-dichlorophenyl)cyclopropyl)methanamine (HCl salt). $^1$H NMR (400 MHz, CD$_3$OD) δ 7.37 (d, J=8.8 Hz, 1H), 6.94 (d, J=8.8 Hz, 1H), 6.18-6.08 (m, 1H), 5.47 (dd, J=17.2, 1.6 Hz, 1H), 5.34 (dd, J=10.4, 1.2 Hz, 1H), 4.63 (d, J=5.2 Hz, 2H), 3.30 (dd, J=12.8, 8.8 Hz, 1H), 2.86 (dd, J=12.8, 8.8 Hz, 1H), 1.83-1.79 (m, 1H), 1.48-1.46 (m, 1H), 1.23-1.15 (m, 2H); $^{13}$C NMR (100 MHz, CD$_3$OD) δ 158.8, 135.9, 134.5, 130.0, 129.9, 125.8, 118.8, 113.3, 71.0, 45.4, 20.2, 18.6, 15.3; $[α]_D^{20}$ +64.0 (c 0.1, MeOH).

Example 40

(−)-(2-(4,5-Difluoro-2-methoxyphenyl)cyclopropyl)
methanamine (HCl Salt)

(+)-(2-(4,5-Difluoro-2-methoxyphenyl)cyclopropyl)
methanamine (HCl Salt)

Route 40:

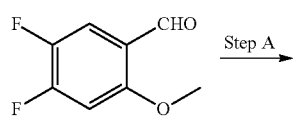

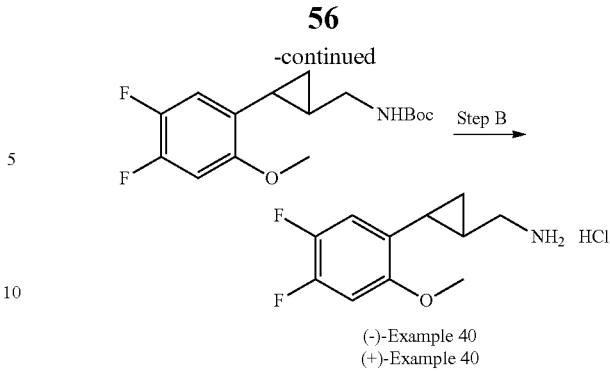

(−)-Example 40
(+)-Example 40

Step A: Tert-butyl ((2-(4,5-difluoro-2-methoxyphenyl)cyclopropyl)methyl)carbamate The subtitle intermediate was prepared from 4,5-difluoro-2-methoxybenzaldehyde using similar methods as described in Example 1. $^1$H NMR (CDCl$_3$, 400 MHz) 6.74 (dd, J=11.2, 9.2 Hz, 1H), 6.65 (dd, J=12.0, 6.8 Hz, 1H), 5.23 (br, 1H), 3.86 (s, 3H), 3.56-3.52 (m, 1H), 2.73-2.68 (m, 1H), 1.75-1.72 (m, 1H), 1.46 (s, 9H), 1.01-0.95 (m, 2H), 0.85-0.82 (m, 2H).

Step B

Racemic tert-butyl ((2-(4,5-difluoro-2-methoxyphenyl)cyclopropyl)methyl)carbamate was separated using chiral HPLC to give (+)-tert-butyl ((2-(4,5-difluoro-2-methoxyphenyl)cyclopropyl)methyl)carbamate and (−)-tert-butyl ((2-(4,5-difluoro-2-methoxyphenyl)cyclopropyl)methyl)carbamate, both were treated with 2M HCl in Et$_2$O to give (−)-(2-(4,5-difluoro-2-methoxyphenyl)cyclopropyl)methanamine (HCl salt) and (+)-(2-(4,5-difluoro-2-methoxyphenyl)cyclopropyl)methanamine (HCl salt) respectively.

(−)-(2-(4,5-Difluoro-2-methoxyphenyl)cyclopropyl)methanamine (HCl salt). $^1$H NMR (CD$_3$OD, 400 MHz) δ 6.94-6.88 (m, 2H), 3.87 (s, 3H), 3.08 (dd, J=13.2, 7.2 Hz, 1H), 2.93 (dd, J=13.2, 8.0 Hz, 1H), 2.09-2.03 (m, 1H), 1.27-1.23 (m, 1H), 1.13-1.08 (m, 1H), 1.04-1.00 (m, 1H); $^{13}$C NMR (CD$_3$OD, 100 MHz) δ 156.2 (d, J$_{CF}$=7.4 Hz), 150.2 (dd, J$_{CF}$=242.7, 13.5 Hz), 145.5 (dd, J$_{CF}$=236.5, 12.6 Hz), 127.1, 116.4 (d, J$_{CF}$=19.2 Hz), 101.6 (d, J$_{CF}$=21.4 Hz), 56.9, 45.1, 19.5, 17.8, 13.1; $[α]_D^{20}$ −7.9 (c 0.7, MeOH).

(+)-(2-(4,5-Difluoro-2-methoxyphenyl)cyclopropyl)methanamine (HCl salt). $^1$H NMR (CD$_3$OD, 400 MHz) δ 6.94-6.88 (m, 2H), 3.87 (s, 3H), 3.08 (dd, J=13.2, 7.2 Hz, 1H), 2.93 (dd, J=13.2, 8.0 Hz, 1H), 2.08-2.03 (m, 1H), 1.26-1.22 (m, 1H), 1.14-1.08 (m, 1H), 1.04-0.98 (m, 1H); $[α]_D^{20}$ +6.0 (c 0.2, MeOH).

Example 41

(−)-(2-(2-Ethoxy-4,5-difluorophenyl)cyclopropyl)
methanamine (HCl Salt)

(+)-(2-(2-Ethoxy-4,5-difluorophenyl)cyclopropyl)
methanamine (HCl Salt)

Route 41:

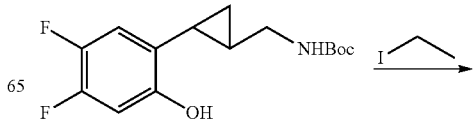

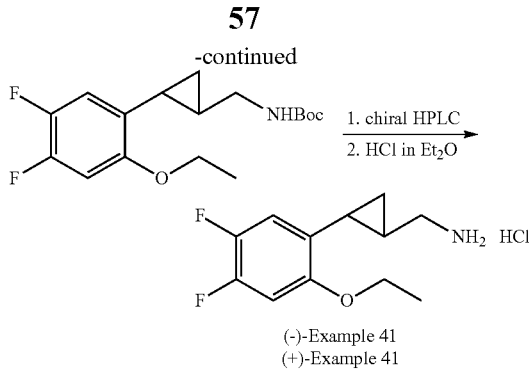

(−)-Example 41
(+)-Example 41

The title compounds were prepared via Route 41 using similar methods described above.

(−)-(2-(2-Ethoxy-4,5-difluorophenyl)cyclopropyl)methanamine (HCl salt). $^1$H NMR (CD$_3$OD, 400 MHz) δ 6.93-6.86 (m, 2H), 4.10-4.03 (m, 2H), 3.07 (dd, J=13.2, 7.2 Hz, 1H), 2.97 (dd, J=13.2, 8.0 Hz, 1H), 2.11-2.06 (m, 1H), 1.45 (t, J=7.2 Hz, 3H), 1.31-1.28 (m, 1H), 1.10-1.01 (m, 2H); $^{13}$C NMR (CD$_3$OD, 100 MHz) δ 155.4 (dd, J$_{CF}$=7.6, 1.9 Hz), 150.0 (dd, J$_{CF}$=242.5, 13.4 Hz), 145.4 (dd, J$_{CF}$=236.3, 12.7 Hz), 127.3, 116.2 (d, J$_{CF}$=18.7 Hz), 102.5 (d, J$_{CF}$=21.2 Hz), 66.0, 45.0, 19.4, 17.9, 15.1, 13.5; [α]$_D^{20}$ −13.2 (c 0.35, MeOH).

(+)-(2-(2-Ethoxy-4,5-difluorophenyl)cyclopropyl)methanamine (HCl salt). $^1$H NMR (CD$_3$OD, 400 MHz) δ 6.93-6.86 (m, 2H), 4.10-4.03 (m, 2H), 3.07 (dd, J=13.2, 7.2 Hz, 1H), 2.97 (dd, J=13.2, 8.0 Hz, 1H), 2.11-2.06 (m, 1H), 1.45 (t, J=7.2 Hz, 3H), 1.31-1.27 (m, 1H), 1.10-1.01 (m, 2H); [α]$_D^{20}$ +13.5 (c 0.2, MeOH).

Example 42

(−)-(2-(4,5-Difluoro-2-(2-fluoroethoxy)phenyl)cyclopropyl)methanamine (HCl Salt)

(+)-(2-(4,5-Difluoro-2-(2-fluoroethoxy)phenyl)cyclopropyl)methanamine (HCl Salt)

Route 42:

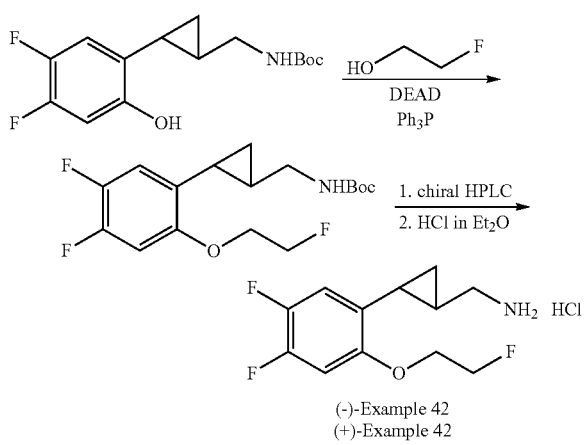

(−)-Example 42
(+)-Example 42

The title compounds were prepared via Route 42 using similar methods described above.

(−)-(2-(4,5-Difluoro-2-(2-fluoroethoxy)phenyl)cyclopropyl)methanamine (HCl salt). $^1$H NMR (CD$_3$OD, 400 MHz) δ 6.99-6.93 (m, 2H), 4.88-4.74 (m, 2H), 4.32-4.22 (m, 2H), 3.03-3.00 (m, 2H), 2.11-2.08 (m, 1H), 1.25-1.15 (m, 2H), 1.05-1.01 (m, 1H); $^{13}$C NMR (CD$_3$OD, 100 MHz) δ 155.0 (dd, J$_{CF}$=7.4, 2.0 Hz), 150.1 (dd, J$_{CF}$=243.0, 13.5 Hz), 145.8 (dd, J$_{CF}$=237.3, 12.6 Hz), 127.6, 116.6 (d, J$_{CF}$=19.5 Hz), 102.9 (d, J$_{CF}$=21.4 Hz), 83.4 (d, J$_{CF}$=166.9 Hz), 69.9 (d, J$_{CF}$=18.8 Hz), 44.9, 19.7, 17.8, 12.8; [α]$_D^{20}$ −1.5 (c 0.4, MeOH).

(+)-(2-(4,5-Difluoro-2-(2-fluoroethoxy)phenyl)cyclopropyl)methanamine (HCl salt). $^1$H NMR (CD$_3$OD, 400 MHz) δ 6.99-6.93 (m, 2H), 4.88-4.74 (m, 2H), 4.32-4.22 (m, 2H), 3.03-3.00 (m, 2H), 2.11-2.07 (m, 1H), 1.24-1.15 (m, 2H), 1.05-1.00 (m, 1H); [α]$_D^{20}$ +1.4 (c 0.1, MeOH).

Example 43

(−)-(2-(4,5-Difluoro-2-propoxyphenyl)cyclopropyl)methanamine (HCl Salt)

(+)-(2-(4,5-Difluoro-2-propoxyphenyl)cyclopropyl)methanamine (HCl Salt)

Route 43:

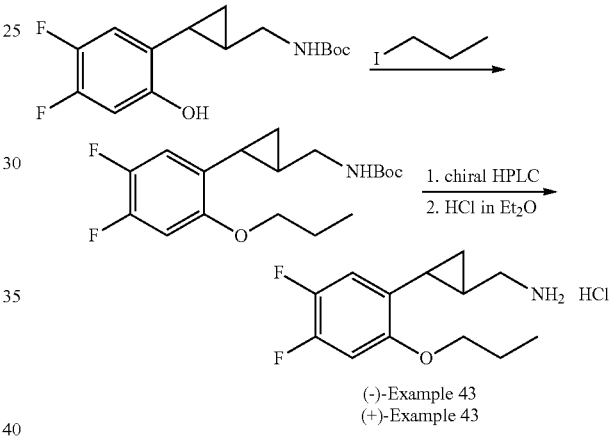

(−)-Example 43
(+)-Example 43

The title compounds were prepared via Route 43 using similar methods described above.

(−)-(2-(4,5-Difluoro-2-propoxyphenyl)cyclopropyl)methanamine (HCl salt). $^1$H NMR (CD$_3$OD, 400 MHz) δ 6.93-6.86 (m, 2H), 4.00-3.93 (m, 2H), 3.16 (dd, J=12.8, 6.8 Hz, 1H), 2.90 (dd, J=13.2, 8.4 Hz, 1H), 2.13-2.09 (m, 1H), 1.89-1.83 (m, 2H), 1.36-1.32 (m, 1H), 1.11-1.02 (m, 5H); $^{13}$C NMR (CD$_3$OD, 100 MHz) δ 155.5 (dd, J$_{CF}$=7.5, 2.0 Hz), 150.0 (dd, J$_{CF}$=229.0, 13.4 Hz), 145.5 (dd, J$_{CF}$=236.3, 12.6 Hz), 127.3, 116.1 (d, J$_{CF}$=19.2 Hz), 102.5 (d, J$_{CF}$=21.2 Hz), 71.9, 45.0, 23.7, 19.3, 18.0, 13.6, 11.0; [α]$_D^{20}$ −17.7 (c 0.3, MeOH).

(+)-(2-(4,5-Difluoro-2-propoxyphenyl)cyclopropyl)methanamine (HCl salt). $^1$H NMR (CD$_3$OD, 400 MHz) δ 6.92-6.86 (m, 2H), 3.99-3.93 (m, 2H), 3.16 (dd, J=12.8, 6.8 Hz, 1H), 2.90 (dd, J=13.2, 8.0 Hz, 1H), 2.12-2.07 (m, 1H), 1.87-1.81 (m, 2H), 1.35-1.30 (m, 1H), 1.11-1.00 (m, 5H); [α]$_D^{20}$ +18.0 (c 0.05, MeOH).

Example 44

(−)-(2-(2-(Allyloxy)-4,5-difluorophenyl)cyclopropyl)methanamine (HCl Salt)

(+)-(2-(2-(Allyloxy)-4,5-difluorophenyl)cyclopropyl)methanamine (HCl Salt)

Route 44:

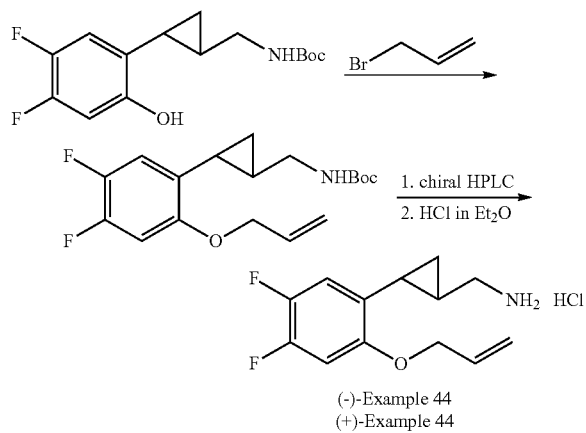

(−)-Example 44
(+)-Example 44

The title compounds were prepared via Route 44 using similar methods described above.

(−)-(2-(2-(Allyloxy)-4,5-difluorophenyl)cyclopropyl)methanamine (HCl salt). $^1$H NMR (CD$_3$OD, 400 MHz) δ 6.95-6.88 (m, 2H), 6.18-6.08 (m, 1H), 5.47 (dd, J=17.2, 1.6 Hz, 1H), 5.33 (dd, J=10.4, 1.6 Hz, 1H), 4.60 (d, J=5.2 Hz, 2H), 3.07 (dd, J=12.8, 7.2 Hz, 1H), 2.98 (dd, J=13.2, 8.0 Hz, 1H), 2.17-2.09 (m, 1H), 1.33-1.29 (m, 1H), 1.13-1.02 (m, 2H); $^{13}$C NMR (CD$_3$OD, 100 MHz) δ 155.0 (dd, J$_{CF}$=7.6, 2.0 Hz), 150.0 (dd, J$_{CF}$=242.8, 13.5 Hz), 145.7 (dd, J$_{CF}$=236.9, 12.7 Hz), 134.5, 127.5, 118.6, 116.2 (d, J$_{CF}$=19.2 Hz), 103.1 (d, J$_{CF}$=21.3 Hz), 71.1, 45.1, 19.4, 18.0, 13.4; [α]$_D^{20}$ −14.0 (c 0.4, MeOH).

(+)-(2-(2-(Allyloxy)-4,5-difluorophenyl)cyclopropyl)methanamine (HCl salt). $^1$H NMR (CD$_3$OD, 400 MHz) δ 6.94-6.89 (m, 2H), 6.18-6.08 (m, 1H), 5.47 (dd, J=17.2, 1.6 Hz, 1H), 5.33 (dd, J=10.8, 1.6 Hz, 1H), 4.60 (d, J=5.2 Hz, 2H), 3.06 (dd, J=13.2, 7.2 Hz, 1H), 2.97 (dd, J=13.2, 7.6 Hz, 1H), 2.17-2.08 (m, 1H), 1.33-1.28 (m, 1H), 1.13-1.02 (m, 2H); [α]$_D^{20}$ +12.0 (c 0.1, MeOH).

Example 45

(−)-(2-(2,3-Difluoro-6-methoxyphenyl)cyclopropyl)methanamine (HCl Salt)

(+)-(2-(2,3-Difluoro-6-methoxyphenyl)cyclopropyl)methanamine (HCl Salt)

Route 45:

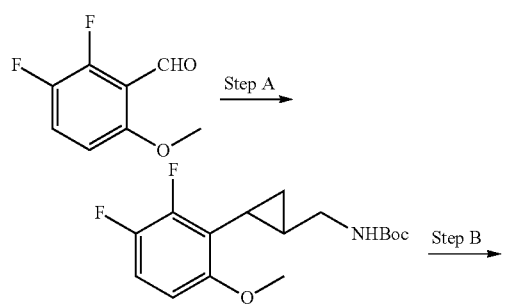

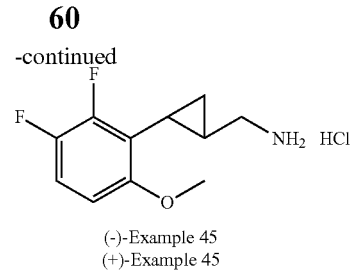

(−)-Example 45
(+)-Example 45

Step A: Tert-butyl ((2-(2,3-difluoro-6-methoxyphenyl)cyclopropyl)methyl)carbamate The subtitle intermediate was prepared from 2,3-difluoro-6-methoxybenzaldehyde using similar methods as described in Example 1. $^1$H NMR (CDCl$_3$, 400 MHz) 6.93 (q, J=9.2 Hz, 1H), 6.52-6.48 (m, 1H), 5.28 (br, 1H), 3.85 (s, 3H), 3.59-3.54 (m, 1H), 2.74-2.68 (m, 1H), 1.53-1.50 (m, 1H), 1.45 (s, 9H), 1.23-1.18 (m, 2H), 0.91-0.86 (m, 1H); $^{13}$C NMR (CDCl$_3$, 100 MHz) δ 156.0, 155.2 (d, J$_{CF}$=5.8 Hz), 150.2 (dd, J$_{CF}$=244.9, 13.8 Hz), 145.8 (dd, J$_{CF}$=224.7, 14.0 Hz), 119.2 (d, J$_{CF}$=11.4 Hz), 113.9 (d, J$_{CF}$=18.2 Hz), 104.9 (dd, J$_{CF}$=6.5, 3.5 Hz), 79.1, 56.0, 45.5, 28.6, 19.7, 12.4, 11.6.

Step B

Racemic tert-butyl ((2-(2,3-difluoro-6-methoxyphenyl)cyclopropyl)methyl)carbamate was separated using chiral HPLC to give (+)-tert-butyl ((2-(2,3-difluoro-6-methoxyphenyl)cyclopropyl)methyl)carbamate and (−)-tert-butyl ((2-(2,3-difluoro-6-methoxyphenyl)cyclopropyl)methyl)carbamate, which was treated with 2M HCl in Et$_2$O to provide (−)-(2-(2,3-difluoro-6-methoxyphenyl)cyclopropyl)methanamine (HCl salt) and (+)-(2-(2,3-difluoro-6-methoxyphenyl)cyclopropyl)methanamine (HCl salt) respectively.

(−)-(2-(2,3-Difluoro-6-methoxyphenyl)cyclopropyl)methanamine (HCl salt). $^1$H NMR (CD$_3$OD, 400 MHz) δ 7.08 (q, J=9.6 Hz, 1H), 6.74-6.71 (m, 1H), 3.86 (s, 3H), 3.13 (dd, J=13.2, 6.8 Hz, 1H), 2.92 (dd, J=13.2, 8.4 Hz, 1H), 1.85-1.79 (m, 1H), 1.54-1.47 (m, 1H), 1.27-1.21 (m, 1H), 1.11-1.05 (m, 1H); [α]$_D^{20}$ −36.9 (c 0.7, MeOH).

(+)-(2-(2,3-Difluoro-6-methoxyphenyl)cyclopropyl)methanamine (HCl salt). $^1$H NMR (CD$_3$OD, 400 MHz) δ 7.08 (q, J=9.6 Hz, 1H), 6.75-6.71 (m, 1H), 3.86 (s, 3H), 3.13 (dd, J=12.8, 6.8 Hz, 1H), 2.91 (dd, J=12.8, 8.4 Hz, 1H), 1.85-1.79 (m, 1H), 1.51-1.46 (m, 1H), 1.27-1.22 (m, 1H), 1.10-1.05 (m, 1H); [α]$_D^{20}$ +38.0 (c 0.2, MeOH).

Example 46

(−)-(2-(6-Ethoxy-2,3-difluorophenyl)cyclopropyl)methanamine (HCl Salt)

(+)-(2-(6-Ethoxy-2,3-difluorophenyl)cyclopropyl)methanamine (HCl Salt)

Route 46:

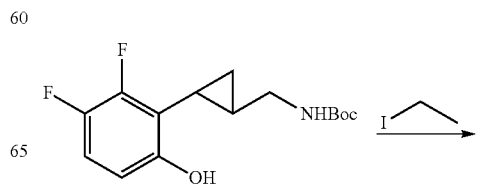

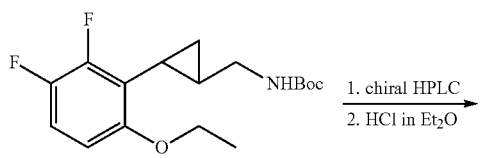

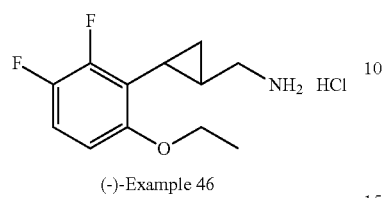

(−)-Example 46
(+)-Example 46

The title compounds were prepared via Route 46 using similar methods described above.

(−)-(2-(6-Ethoxy-2,3-difluorophenyl)cyclopropyl)methanamine (HCl salt). $^1$H NMR (CD$_3$OD, 400 MHz) δ 7.05 (q, J=9.6 Hz, 1H), 6.72-6.68 (m, 1H), 4.11-4.04 (m, 2H), 3.09 (dd, J=13.2, 7.6 Hz, 1H), 2.98 (dd, J=13.2, 7.6 Hz, 1H), 1.89-1.85 (m, 1H), 1.62-1.58 (m, 1H), 1.45 (t, J=7.2 Hz, 3H), 1.32-1.28 (m, 1H), 1.10-1.06 (m, 1H); $^{13}$C NMR (CD$_3$OD, 100 MHz) δ 156.0 (dd, $J_{CF}$=5.5, 2.1 Hz), 151.3 (dd, $J_{CF}$=243.0, 14.0 Hz), 146.7 (dd, $J_{CF}$=237.1, 13.8 Hz), 119.5 (d, $J_{CF}$=11.1 Hz), 115.4 (d, $J_{CF}$=18.2 Hz), 107.9 (dd, $J_{CF}$=6.4, 3.5 Hz), 65.9, 45.4, 18.2, 15.2, 13.9, 13.0; $[\alpha]_D^{20}$ −45.2 (c 0.5, MeOH).

(+)-(2-(6-Ethoxy-2,3-difluorophenyl)cyclopropyl)methanamine (HCl salt). $^1$H NMR (CD$_3$OD, 400 MHz) δ 7.05 (q, J=9.6 Hz, 1H), 6.72-6.68 (m, 1H), 4.11-4.04 (m, 2H), 3.10 (dd, J=12.8, 7.2 Hz, 1H), 2.98 (dd, J=13.2, 8.0 Hz, 1H), 1.89-1.85 (m, 1H), 1.62-1.59 (m, 1H), 1.45 (t, J=7.2 Hz, 3H), 1.32-1.28 (m, 1H), 1.10-1.07 (m, 1H); $[\alpha]_D^{20}$ +37.5 (c 0.2, MeOH).

Example 47

(−)-(2-(2,3-Difluoro-6-(2-fluoroethoxy)phenyl)cyclopropyl)methanamine (HCl Salt)

(+)-(2-(2,3-Difluoro-6-(2-fluoroethoxy)phenyl)cyclopropyl)methanamine (HCl Salt)

Route 47:

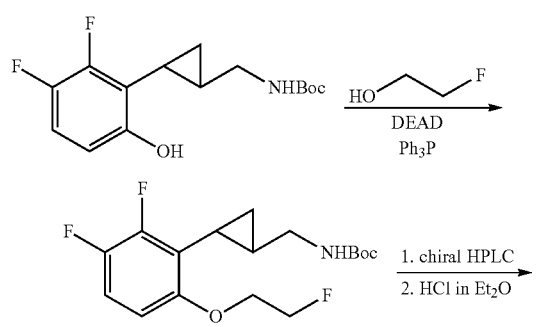

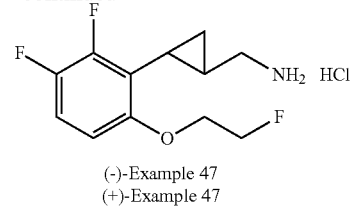

(−)-Example 47
(+)-Example 47

The title compounds were prepared via Route 47 using similar methods described above.

(−)-(2-(2,3-Difluoro-6-(2-fluoroethoxy)phenyl)cyclopropyl)methanamine (HCl salt). $^1$H NMR (CD$_3$OD, 400 MHz) δ 7.09 (q, J=9.6 Hz, 1H), 6.77-6.73 (m, 1H), 4.88-4.86 (m, 1H), 4.77-4.74 (m, 1H), 4.31-4.20 (m, 2H), 3.10 (dd, J=13.2, 7.6 Hz, 1H), 2.99 (dd, J=13.2, 7.6 Hz, 1H), 1.89-1.84 (m, 1H), 1.56-1.53 (m, 1H), 1.35-1.31 (m, 1H), 1.12-1.07 (m, 1H); $^{13}$C NMR (CD$_3$OD, 100 MHz) δ 155.6 (dd, $J_{CF}$=5.6, 2.1 Hz), 151.4 (dd, $J_{CF}$=243.7, 13.9 Hz), 147.0 (dd, $J_{CF}$=238.0, 13.8 Hz), 119.9 (d, $J_{CF}$=11.5 Hz), 115.6 (d, $J_{CF}$=18.3 Hz), 108.2 (dd, $J_{CF}$=3.6 Hz), 83.4 (d, $J_{CF}$=167.1 Hz), 69.7 (d, $J_{CF}$=18.9 Hz), 45.2, 18.4, 13.8, 12.9; $[\alpha]_D^{20}$ −36.0 (c 0.5, MeOH).

(+)-(2-(2,3-Difluoro-6-(2-fluoroethoxy)phenyl)cyclopropyl)methanamine (HCl salt). $^1$H NMR (CD$_3$OD, 400 MHz) δ 7.09 (q, J=9.6 Hz, 1H), 6.77-6.73 (m, 1H), 4.88-4.85 (m, 1H), 4.76-4.74 (m, 1H), 4.31-4.20 (m, 2H), 3.09 (dd, J=13.2, 7.6 Hz, 1H), 2.99 (dd, J=12.8, 7.6 Hz, 1H), 1.89-1.84 (m, 1H), 1.56-1.53 (m, 1H), 1.35-1.31 (m, 1H), 1.12-1.07 (m, 1H); $[\alpha]_D^{20}$ +30.2 (c 0.2, MeOH).

Example 48

(−)-(2-(2,3-Difluoro-6-propoxyphenyl)cyclopropyl)methanamine (HCl Salt)

(+)-(2-(2,3-Difluoro-6-propoxyphenyl)cyclopropyl)methanamine (HCl Salt)

Route 48:

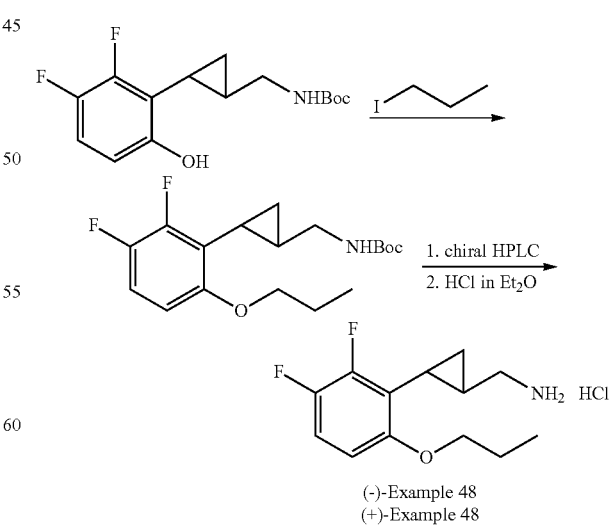

(−)-Example 48
(+)-Example 48

The title compounds were prepared via Route 48 using similar methods described above.

(−)-(2-(2,3-Difluoro-6-propoxyphenyl)cyclopropyl)methanamine (HCl salt). $^1$H NMR (CD$_3$OD, 400 MHz) δ 7.05 (q, J=9.6 Hz, 1H), 6.71-6.68 (m, 1H), 4.01-3.90 (m, 2H), 3.14 (dd, J=13.2, 7.6 Hz, 1H), 2.93 (dd, J=12.8, 8.0 Hz, 1H), 1.90-1.81 (m, 3H), 1.66-1.58 (m, 1H), 1.30-1.25 (m, 1H), 1.11-1.05 (m, 4H); $^{13}$C NMR (CD$_3$OD, 100 MHz) δ 156.1, 151.3 (dd, J$_{CF}$=242.9, 14.3 Hz), 146.6 (dd, J$_{CF}$=237.0, 13.7 Hz), 119.4 (d, J$_{CF}$=11.2 Hz), 115.4 (d, J$_{CF}$=18.2 Hz), 107.7 (dd, J$_{CF}$=6.2, 3.5 Hz), 71.8, 45.3, 23.8, 18.2, 14.0, 13.1, 11.1; $[α]_D^{20}$ −50.3 (c 0.4, MeOH).

(+)-(2-(2,3-Difluoro-6-propoxyphenyl)cyclopropyl)methanamine (HCl salt). $^1$H NMR (CD$_3$OD, 400 MHz) δ 7.05 (q, J=9.6 Hz, 1H), 6.71-6.68 (m, 1H), 4.01-3.90 (m, 2H), 3.13 (dd, J=13.2, 7.6 Hz, 1H), 2.93 (dd, J=13.2, 8.0 Hz, 1H), 1.90-1.81 (m, 3H), 1.66-1.57 (m, 1H), 1.30-1.25 (m, 1H), 1.11-1.05 (m, 4H); $[α]_D^{20}$ +42.5 (c 0.2, MeOH).

Example 49

(−)-(2-(6-(Allyloxy)-2,3-difluorophenyl)cyclopropyl)methanamine (HCl Salt)

(+)-(2-(6-(Allyloxy)-2,3-difluorophenyl)cyclopropyl)methanamine (HCl Salt)

Route 49:

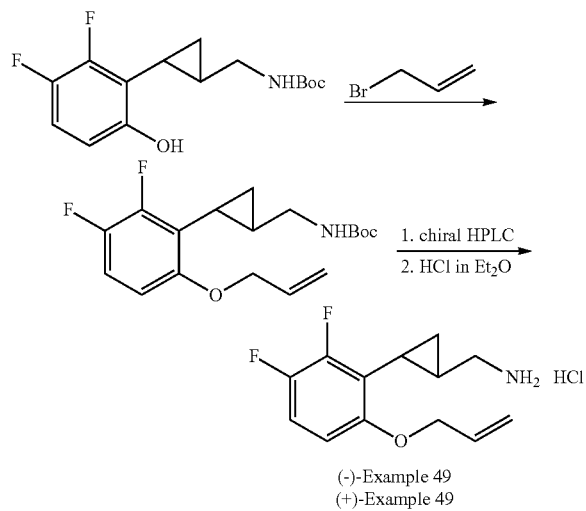

(−)-Example 49
(+)-Example 49

The title compounds were prepared via Route 49 using similar methods described above.

(−)-(2-(6-(Allyloxy)-2,3-difluorophenyl)cyclopropyl)methanamine (HCl salt). $^1$H NMR (CD$_3$OD, 400 MHz) δ 7.06 (q, J=9.6 Hz, 1H), 6.75-6.71 (m, 1H), 6.16-6.09 (m, 1H), 5.46 (dd, J=17.2, 1.6 Hz, 1H), 5.32 (dd, J=10.8, 1.6 Hz, 1H), 4.59 (d, J=5.6 Hz, 2H), 3.08 (dd, J=13.2, 7.6 Hz, 1H), 3.01 (dd, J=13.2, 7.6 Hz, 1H), 1.91-1.86 (m, 1H), 1.61-1.56 (m, 1H), 1.31-1.27 (m, 1H), 1.12-1.08 (m, 1H); $^{13}$C NMR (CD$_3$OD, 100 MHz) δ 155.7 (d, J$_{CF}$=5.6 Hz), 151.3 (dd, J$_{CF}$=243.3, 14.0 Hz), 146.8 (dd, J$_{CF}$=237.6, 13.8 Hz), 134.6, 119.7 (d, J$_{CF}$=11.2 Hz), 118.6, 115.5 (d, J$_{CF}$=18.3 Hz), 108.5, 71.1, 45.3, 18.3, 13.9, 13.0; $[α]_D^{20}$ −46.8 (c 0.5, MeOH).

(+)-(2-(6-(Allyloxy)-2,3-difluorophenyl)cyclopropyl)methanamine (HCl salt). $^1$H NMR (CD$_3$OD, 400 MHz) δ 7.06 (q, J=9.6 Hz, 1H), 6.75-6.71 (m, 1H), 6.16-6.08 (m, 1H), 5.46 (dd, J=17.2, 1.6 Hz, 1H), 5.32 (dd, J=10.4, 1.6 Hz, 1H), 4.59 (d, J=5.6 Hz, 2H), 3.07 (dd, J=13.2, 7.6 Hz, 1H), 3.00 (dd, J=13.2, 7.6 Hz, 1H), 1.91-1.85 (m, 1H), 1.60-1.56 (m, 1H), 1.31-1.26 (m, 1H), 1.11-1.06 (m, 1H); $[α]_D^{20}$ +41.6 (c 0.2, MeOH).

Example 50

(−)-(2-(2-Chloro-3-fluoro-6-methoxyphenyl)cyclopropyl)methanamine (HCl Salt)

(+)-(2-(2-Chloro-3-fluoro-6-methoxyphenyl)cyclopropyl)methanamine (HCl Salt)

Route 50:

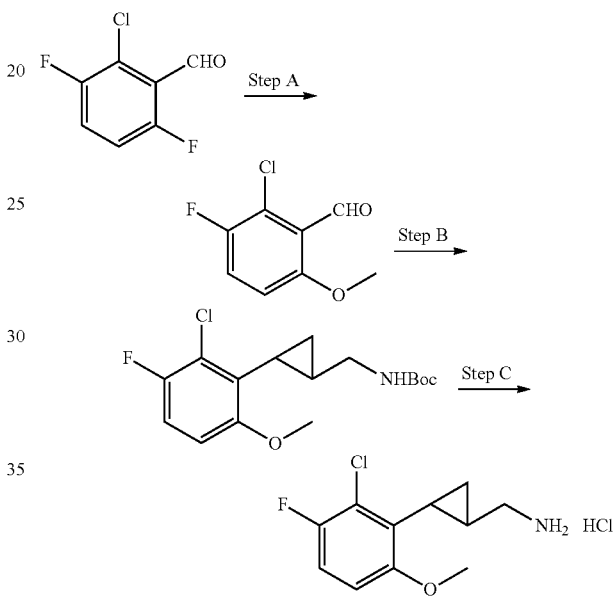

Step A: 2-Chloro-3-fluoro-6-methoxybenzaldehyde

A solution of 2-chloro-3,6-difluorobenzaldehyde (5.0 g, 29.3 mmol) in anhydrous THF (25 mL) and MeOH (60 mL) was heated to 60° C., and a solution of MeONa in MeOH (25% wt %, 1.6 mL) was added and the mixture was stirred at 60° C. overnight. The mixture was concentrated and residue was taken in ethyl acetate, washed with water, dried over Na$_2$SO$_4$, concentrated and purified with flash chromatography (0-30% ethyl acetate in hexane) to give white solid (3.75 g, 68%). $^1$H NMR (400 MHz, CDCl$_3$) δ 10.48 (s, 1H), 7.31 (t, J=8.0 Hz, 1H), 6.88 (dd, J=8.0, 4.0 Hz, 1H), 3.92 (s, 3H).

Step B: Tert-butyl ((2-(2-chloro-3-fluoro-6-methoxyphenyl)cyclopropyl)methyl)carbamate The subtitle intermediate was prepared from 2-chloro-3-fluoro-6-methoxybenzaldehyde using similar methods as described in Example 1. $^1$H NMR (400 MHz, CDCl$_3$) δ 6.98 (t, J=8.8 Hz, 1H), 6.69 (dd, J=9.0, 4.0 Hz, 1H), 5.22 (br, 1H), 3.85 (s, 3H), 3.53-3.48 (m, 1H), 2.91-2.85 (m, 1H), 1.53-1.49 (m, 1H), 1.47 (s, 3H), 1.27-1.24 (m, 1H), 1.06-0.97 (m, 2H).

Step C

Racemic tert-butyl ((2-(2-chloro-3-fluoro-6-methoxyphenyl)cyclopropyl)methyl)carbamate was separated with chiral HPLC to give (−)-tert-butyl ((2-(2-chloro-3-fluoro-6-methoxyphenyl)cyclopropyl)methyl)carbamate and (+)-tert-butyl ((2-(2-chloro-3-fluoro-6-methoxyphenyl)cyclopropyl)methyl)carbamate, which were treated with 2M HCl in Et$_2$O to provide (−)-(2-(2-chloro-3-fluoro-6-methoxyphenyl)cyclopropyl)methanamine (HCl salt) and (+)-(2-(2-chloro-3-fluoro-6-methoxyphenyl)cyclopropyl)methanamine (HCl salt) respectively.

(−)-(2-(2-Chloro-3-fluoro-6-methoxyphenyl)cyclopropyl)methanamine (HCl salt). $^1$H NMR (400 MHz, CD$_3$OD) δ 7.10 (t, J=8.8 Hz, 1H), 6.92 (dd, J=9.2, 4.4 Hz, 1H), 3.86 (s, 3H), 3.10-3.00 (m, 2H), 1.76-1.73 (m, 1H), 1.47-1.42 (m, 1H), 1.19-1.08 (m, 2H); $^{13}$C NMR (100 MHz, CD$_3$OD) δ 157.1, 154.2 (d, J$_{CF}$=237.8 Hz), 129.1, 124.6 (d, J$_{CF}$=18.2 Hz), 115.5 (d, J$_{CF}$=22.9 Hz), 111.1 (d, J$_{CF}$=8.5 Hz), 56.8, 45.4, 19.6, 17.5, 14.7; [α]$_D^{20}$ −66.4 (c 0.3, MeOH).

(+)-(2-(2-Chloro-3-fluoro-6-methoxyphenyl)cyclopropyl)methanamine (HCl salt). $^1$H NMR (400 MHz, CD$_3$OD) δ 7.10 (t, J=8.8 Hz, 1H), 6.92 (dd, J=9.2, 4.4 Hz, 1H), 3.86 (s, 3H), 3.10-3.00 (m, 2H), 1.76-1.73 (m, 1H), 1.47-1.43 (m, 1H), 1.19-1.07 (m, 2H); $^{13}$C NMR (100 MHz, CD$_3$OD) δ 157.1, 154.2 (d, J$_{CF}$=237.9 Hz), 129.1, 124.6 (d, J$_{CF}$=18.1 Hz), 115.5 (d, J$_{CF}$=22.9 Hz), 111.1 (d, J$_{CF}$=8.4 Hz), 56.8, 45.4, 19.6, 17.5, 14.7; [α]$_D^{20}$ +69.4 (c 0.3, MeOH).

Example 51

(−)-(2-(2-Chloro-6-ethoxy-3-fluorophenyl)cyclopropyl)methanamine (HCl Salt)

(+)-(2-(2-Chloro-6-ethoxy-3-fluorophenyl)cyclopropyl)methanamine (HCl Salt)

Route 51:

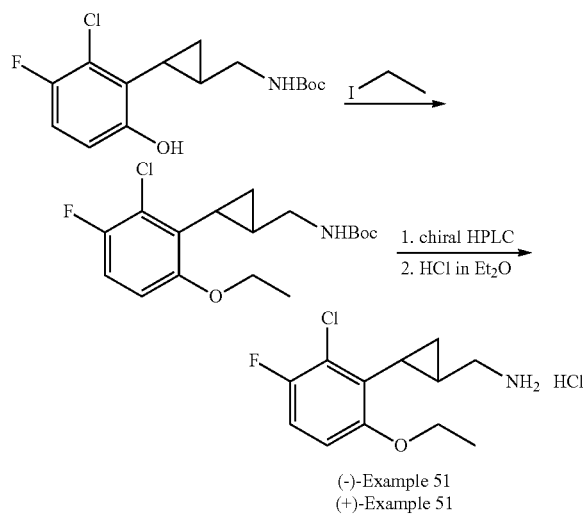

(−)-Example 51
(+)-Example 51

The title compounds were prepared via Route 51 using similar methods described above.

(−)-(2-(2-Chloro-6-ethoxy-3-fluorophenyl)cyclopropyl)methanamine (HCl salt). $^1$H NMR (400 MHz, CD$_3$OD) δ 7.06 (t, J=8.8 Hz, 1H), 6.88 (dd, J=9.2, 4.4 Hz, 1H), 4.10-4.02 (m, 2H), 3.32 (dd, J=12.8, 6.0 Hz, 1H), 2.83 (dd, J=13.2, 8.8 Hz, 1H), 1.80-1.77 (m, 1H), 1.53-1.48 (m, 1H), 1.44 (t, J=7.2 Hz, 3H), 1.20-1.15 (m, 2H); $^{13}$C NMR (100 MHz, CD$_3$OD) δ 156.4, 154.1 (d, J$_{CF}$=237.8 Hz), 129.2, 124.5 (d, J$_{CF}$=18.2 Hz), 115.4 (d, J$_{CF}$=22.7 Hz), 112.2 (d, J$_{CF}$=7.5 Hz), 65.9, 45.4, 19.6, 17.8, 15.3, 14.8; [α]$_D^{20}$ −62.0 (c 0.3, MeOH).

(+)-(2-(2-Chloro-6-ethoxy-3-fluorophenyl)cyclopropyl)methanamine (HCl salt). $^1$H NMR (400 MHz, CD$_3$OD) δ 7.08 (t, J=8.8 Hz, 1H), 6.89 (dd, J=9.2, 4.4 Hz, 1H), 4.13-4.03 (m, 2H), 3.32 (dd, J=12.8, 6.0 Hz, 1H), 2.85 (dd, J=13.2, 8.8 Hz, 1H), 1.82-1.78 (m, 1H), 1.54-1.50 (m, 1H), 1.46 (t, J=7.2 Hz, 3H), 1.21-1.16 (m, 2H); $^{13}$C NMR (100 MHz, CD$_3$OD) δ 156.4, 154.1 (d, J$_{CF}$=237.7 Hz), 129.3, 124.5 (d, J$_{CF}$=18.1 Hz), 115.4 (d, J$_{CF}$=22.7 Hz), 112.2 (d, J$_{CF}$=7.5 Hz), 65.9, 45.4, 19.6, 17.8, 15.3, 14.8; [α]$_D^{20}$ +70.7 (c 0.3, MeOH).

Example 52

(−)-(2-(2-Chloro-3-fluoro-6-(2-fluoroethoxy)phenyl)cyclopropyl)methanamine (HCl Salt)

(+)-(2-(2-Chloro-3-fluoro-6-(2-fluoroethoxy)phenyl)cyclopropyl)methanamine (HCl Salt)

Route 52:

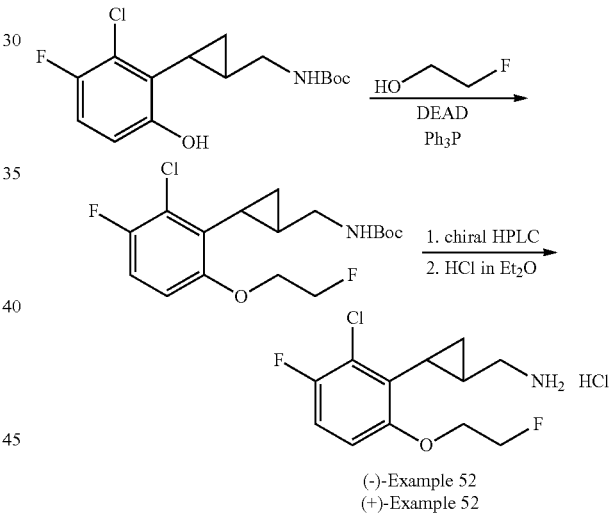

(−)-Example 52
(+)-Example 52

The title compounds were prepared via Route 52 using similar methods described above.

(−)-(2-(2-Chloro-3-fluoro-6-(2-fluoroethoxy)phenyl)cyclopropyl)methanamine (HCl salt). $^1$H NMR (400 MHz, CD$_3$OD) δ 7.11 (t, J=8.8 Hz, 1H), 6.94 (dd, J=9.0, 4.2 Hz, 1H), 4.88-4.85 (m, 1H), 4.77-4.74 (m, 1H), 4.32-4.20 (m, 2H), 3.34 (dd, J=13.2, 6.4 Hz, 1H), 2.85 (dd, J=13.2, 8.8 Hz, 1H), 1.85-1.79 (m, 1H), 1.56-1.50 (m, 1H), 1.23-1.18 (m, 2H); $^{13}$C NMR (100 MHz, CD$_3$OD) δ 156.0, 154.5 (d, J$_{CF}$=238.6 Hz), 129.7, 124.7 (d, J$_{CF}$=18.2 Hz), 115.5 (d, J$_{CF}$=22.9 Hz), 112.6 (d, J$_{CF}$=7.6 Hz), 83.4 (d, J$_{CF}$=167.3 Hz), 69.8 (d, J$_{CF}$=18.9 Hz), 45.3, 19.7, 17.7, 14.7; [α]$_D^{20}$ −54.5 (c 0.2, MeOH).

(+)-(2-(2-Chloro-3-fluoro-6-(2-fluoroethoxy)phenyl)cyclopropyl)methanamine (HCl salt). $^1$H NMR (400 MHz, CD$_3$OD) δ 7.11 (t, J=8.8 Hz, 1H), 6.94 (dd, J=9.0, 4.2 Hz, 1H), 4.88-4.85 (m, 1H), 4.78-4.74 (m, 1H), 4.33-4.20 (m, 2H), 3.34 (dd, J=13.2, 8.8 Hz, 1H), 2.85 (dd, J=13.2, 8.8 Hz, 1H), 1.85-1.79 (m, 1H), 1.56-1.52 (m, 1H), 1.24-1.17 (m, 2H); $^{13}$C NMR (100 MHz, CD$_3$OD) δ 156.0, 154.5 (d, J$_{CF}$=238.6 Hz), 129.7, 124.7 (d, J$_{CF}$=18.2 Hz), 115.5 (d, J$_{CF}$=22.8 Hz), 112.6 (d, J$_{CF}$=7.7 Hz), 83.4 (d, J$_{CF}$=167.3 Hz), 69.8 (d, J$_{CF}$=19.0 Hz), 45.3, 19.7, 17.7, 14.7; [α]$_D^{20}$ +61.4 (c 0.3, MeOH).

Example 53

(−)-(2-(6-(Allyloxy)-2-chloro-3-fluorophenyl)cyclopropyl)methanamine HCl Salt (+)-(2-(6-(Allyloxy)-2-chloro-3-fluorophenyl)cyclopropyl)methanamine HCl Salt Route 53:

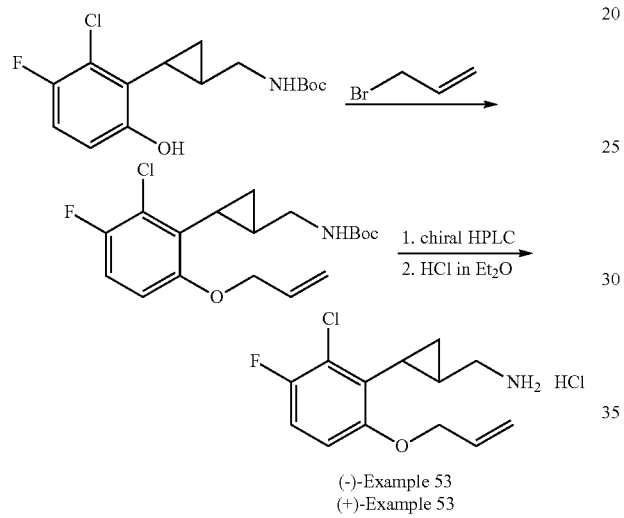

The title compounds were prepared via Route 53 using similar methods described above.

(−)-(2-(6-(Allyloxy)-2-chloro-3-fluorophenyl)cyclopropyl)methanamine HCl salt. $^1$H NMR (400 MHz, CD$_3$OD) δ 7.09 (t, J=8.8 Hz, 1H), 6.92 (dd, J=9.2, 4.4 Hz, 1H), 6.16-6.07 (m, 1H), 5.46 (dd, J=17.6, 1.6 Hz, 1H), 5.33 (dd, J=10.6, 1.4 Hz, 1H), 4.60 (d, J=5.6 Hz, 2H), 3.29 (dd, J=13.2, 6.4 Hz, 1H), 2.87 (dd, J=12.8, 8.6 Hz, 1H), 1.84-1.77 (m, 1H), 1.53-1.47 (m, 1H), 1.22-1.17 (m, 2H); $^{13}$C NMR (100 MHz, CD$_3$OD) δ 156.1, 154.3 (d, J$_{CF}$=238.3 Hz), 134.7, 129.5, 124.5 (d, J$_{CF}$=18.2 Hz), 118.7, 115.4 (d, J$_{CF}$=22.7 Hz), 112.8 (d, J$_{CF}$=7.5 Hz), 71.1, 45.4, 19.7, 17.7, 14.8; [α]$_D^{20}$ −52.0 (c 0.2, MeOH).

(+)-(2-(6-(Allyloxy)-2-chloro-3-fluorophenyl)cyclopropyl)methanamine HCl salt. $^1$H NMR (400 MHz, CD$_3$OD) δ 7.09 (t, J=8.8 Hz, 1H), 6.92 (dd, J=9.2, 4.4 Hz, 1H), 6.17-6.08 (m, 1H), 5.46 (dd, J=17.6, 1.6 Hz, 1H), 5.33 (dd, J=10.4, 1.2 Hz, 1H), 4.60 (d, J=4.8 Hz, 2H), 3.29 (dd, J=13.6, 6.0 Hz, 1H), 2.87 (dd, J=12.8, 8.8 Hz, 1H), 1.84-1.78 (m, 1H), 1.53-1.47 (m, 1H), 1.21-1.17 (m, 2H); $^{13}$C NMR (100 MHz, CD$_3$OD) δ 156.1, 154.3 (d, J$_{CF}$=238.0 Hz), 134.7, 129.5, 124.5 (d, J$_{CF}$=18.1 Hz), 118.7, 115.4 (d, J$_{CF}$=220.7 Hz), 112.8 (d, J$_{CF}$=6.6 Hz), 71.1, 45.3, 19.7, 17.7, 14.8; [α]$_D^{20}$ +61.8 (c 0.4, MeOH).

Compounds of the present invention therefore include, but are not limited to:

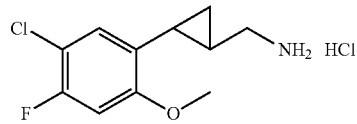

Example 1

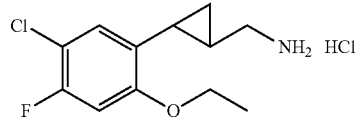

Example 2

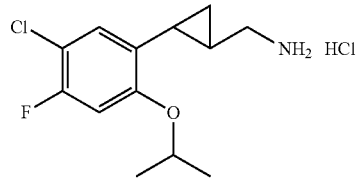

Example 3

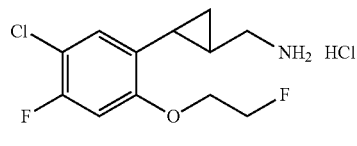

Example 4

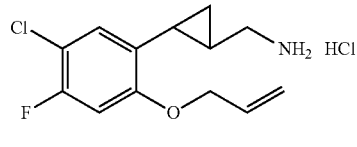

Example 5

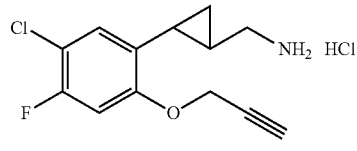

Example 6

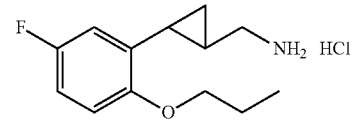

Example 7

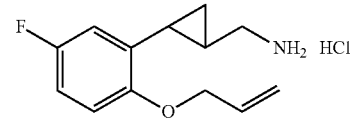

Example 8

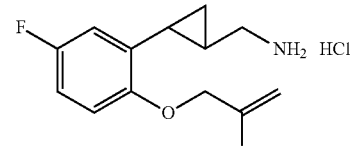

Example 9

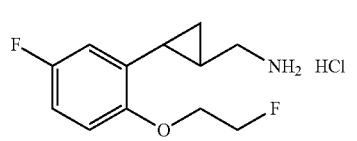

Example 10

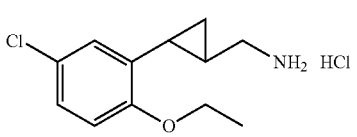

Example 11

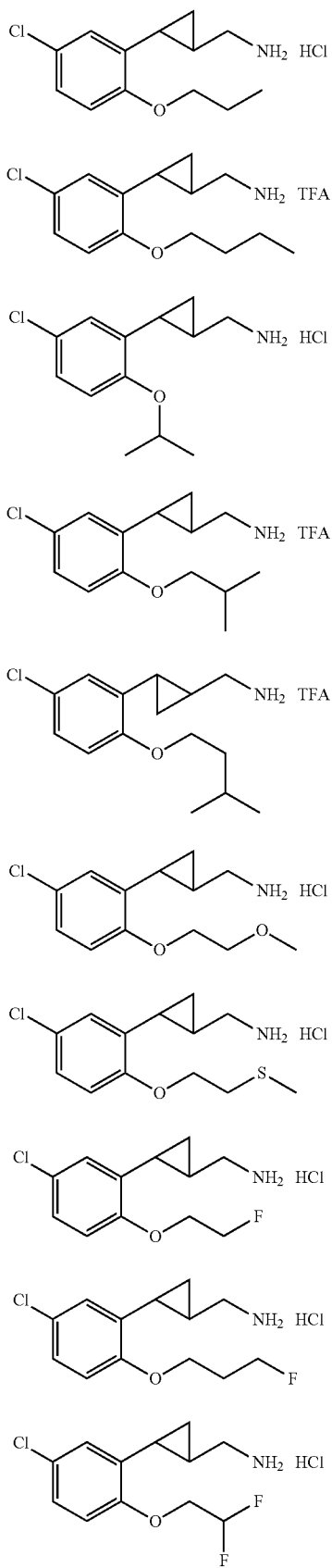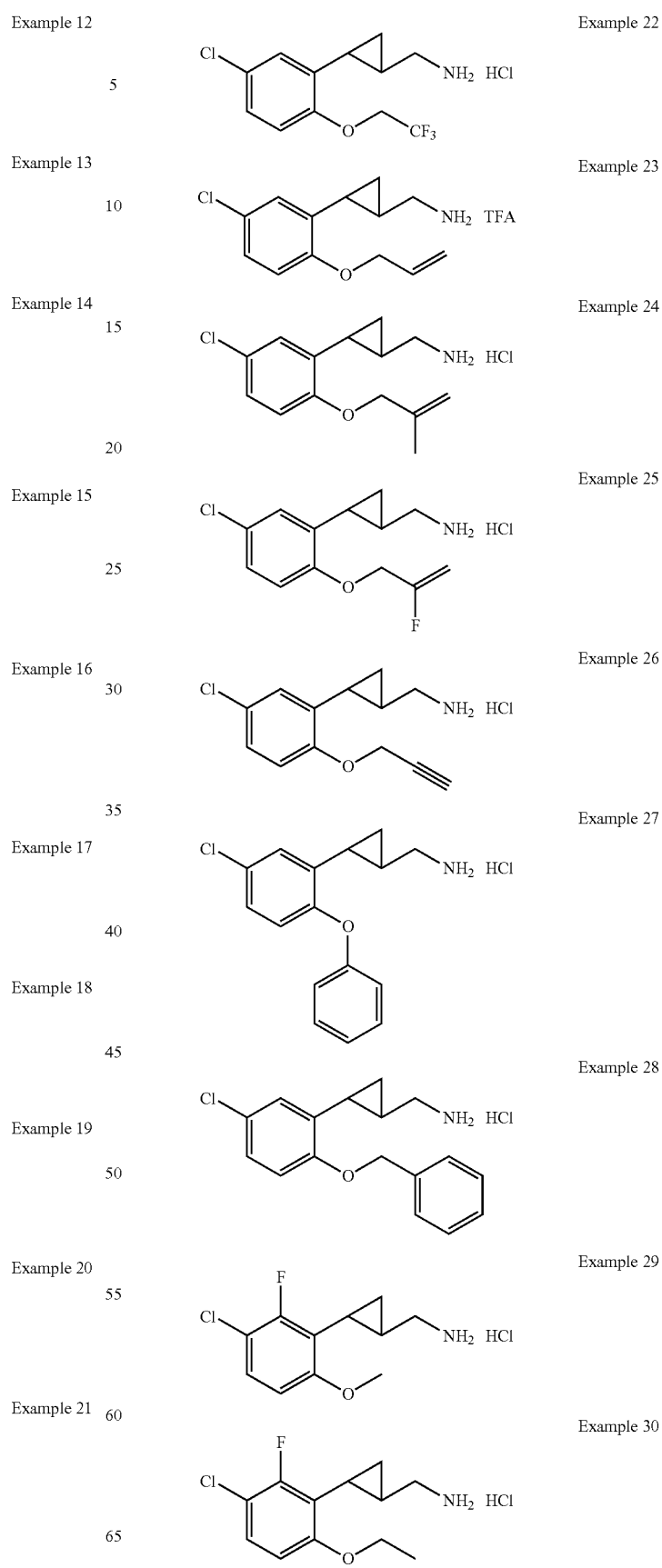

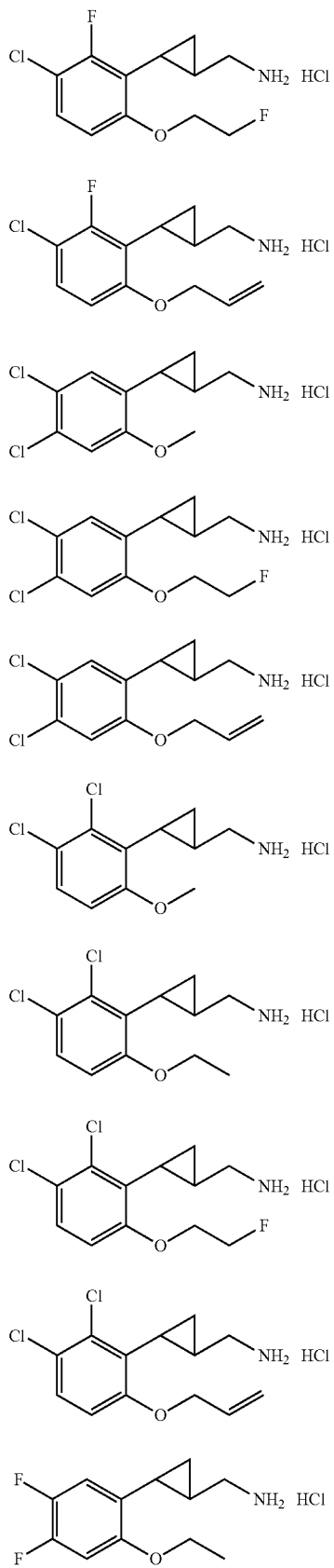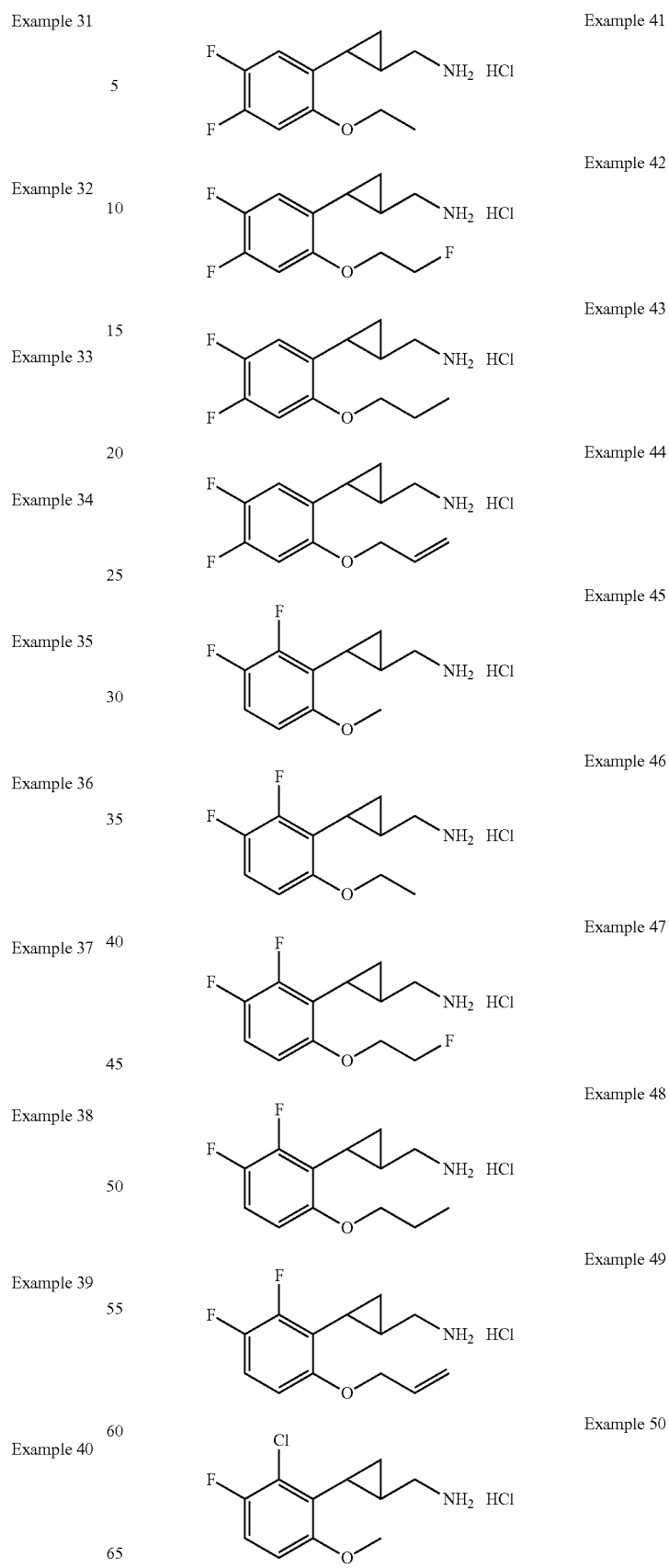

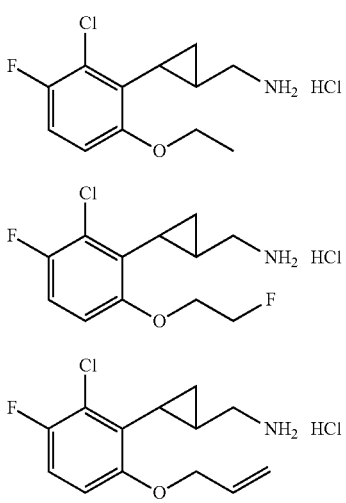

Example 51

Example 52

Example 53

In one embodiment, the present invention relates to a method of treating an individual suffering from a disease or condition wherein agonism of 5-HT(2C) receptors provides a benefit comprising administering a therapeutically effective amount of a compound of structural formula (I) to an individual in need thereof.

The methods described herein relate to the use of a compound of structural formula (I) and an optional second therapeutic agent useful in the treatment of diseases and conditions wherein modulation of 5HT(2C) receptor activity provides a benefit. The methods of the present invention can be accomplished by administering a compound of structural formula (I) as the neat compound or as a pharmaceutical composition. Administration of a pharmaceutical composition, or a neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered.

In many embodiments, a compound of structural formula (I) is administered in conjunction with a second therapeutic agent useful in the treatment of a disease or condition wherein modulation of 5-HT(2C) receptors provides a benefit. The second therapeutic agent is different from the compound of structural formula (I). A compound of structural formula (I) and the second therapeutic agent can be administered simultaneously or sequentially. In addition, a compound of structural formula (I) and second therapeutic agent can be administered from a single composition or two separate compositions. A compound of structural formula (I) and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein modulation of 5-HT(2C) receptors provides a benefit. The present invention also is directed to pharmaceutical compositions comprising a compound of structural formula (I) and an optional second therapeutic agent useful in the treatment of diseases and conditions wherein modulation of 5-HT(2C) receptors provides a benefit. Further provided are kits comprising a compound of structural formula (I) and, optionally, a second therapeutic agent useful in the treatment of diseases and conditions wherein modulation of 5-HT(2C) receptors provides a benefit, packaged separately or together, and an insert having instructions for using these active agents.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agent, for example, but not limited to, known drugs to treat psychiatric disorders.

Within the meaning of the present invention, the term "disease" or "condition" or "disorder" denotes disturbances and/or anomalies that as a rule are regarded as being pathological conditions or functions, and that can manifest themselves in the form of particular signs, symptoms, and/or malfunctions. As demonstrated below, a compound of structural formula (I) is a potent modulator of 5-HT(2C) receptors and can be used in treating diseases and conditions wherein modulation of 5-HT(2C) receptors provides a benefit.

Compounds of structural formula (I) therefore generally function as modulators (agonists, partial agonist, antagonists, partial antagonists, as well as selective agonists) of the 5-HT(2) family of receptors. More specifically, the present compounds function as agonists of 5-HT(2) receptors. Even more specifically, the present compounds invention function as agonists or selective agonists of the 5-HT(2C) receptors. The compounds of structural formula (I) therefore can be used in the treatment of diseases, conditions, and disorders, or amelioraton of undesired symptoms, associated with the 5-HT(2C) receptor.

Diseases, conditions, disorders symptoms associated with the 5-HT(2C) receptor include among others, obesity, eating disorders, diabetes, cardiovascular disorders, sleep disorders (e.g., sleep apnea), disorders of the central nervous system, damage to the central nervous system (e.g., trauma, stroke, or spinal cord injury), gastrointestinal disorders (irritable bowel syndrome), depression, atypical depression, bipolar disorders, anxiety disorders, adjustment disorders, obsessive compulsive disorders, social phobias or panic, sexual dysfunction, psychoses, schizophrenia, conditions associated with cephalic pain, chronic pain, dystonia, raised intracranial pressure, epilepsy, personality disorders, Alzheimer's disease, age-related behavioral disorders, behavioral disorders associated with dementia, organic mental disorders, mental disorders in childhood, aggressivity, age-related memory disorders, chronic fatigue syndrome, drug and alcohol addiction, bulimia, anorexia nervosa, and premenstrual tension.

5-HT(2C) receptor-associated disorders, conditions, diseases, and symptoms that can be treated by compounds of structural formula (I) include among others:

obesity, eating disorders (e.g., hyperphagia, bulimia, or anorexia nervosa), gastrointestinal disorders, malfunction of gastrointestinal motility, chemotherapy-induced emesis, diabetes, sleep disorders, sleep apnea, hypertension, hypertension, hyperlipidemia, cardiovascular disease, central nervous system disorders, damage to the central nervous system associated with trauma, stroke, or spinal cord injury or complications, psychiatric disorders, obsessive-compulsive disorder, anxiety, panic disorder, schizophrenia, schizoaffective disorder, schizophreniform disorder, L-DOPA-induced psychosis, psychosis, dementia, memory deficit, intellectual deficit associated with Alzheimer's disease, bipolar disorders, adjustment disorders, depression, movement disorders, dystonia, chronic pain, Parkinson's Disease, Alzheimer's Disease, sexual dysfunction in males or females, erectile dysfunction, epilepsy, headache, and migraines. 5-HT(2C) receptor agonists are particularly useful for treatment of obesity and comorbidities thereof, including Type II diabetes, cardiovascular disease, hypertension, hyperlipidemia, stroke, osteoarthritis, sleep apnea, gall bladder disease, gout, some cancers, some infertility, and early mortality.

5-HT(2C) receptor agonists also are useful in the methods of decreasing food intake in an individual, of inducing satiety in an individual, of controlling weight gain of an individual, and in generally providing benefit to individuals in the form of weight reduction.

Additional diseases and conditions associated with the 5-HT(2C) receptor, and treatable by a present compound, are disclosed in U.S. Patent Publication No. 2008/0119477 and WO 2006/065600, each incorporated herein by reference in its entirety.

The present invention provides methods of treating disorders, diseases, conditions, and symptoms in a mammal and particularly in a human, by administering to an individual in need of treatment or prophylaxis, a therapeutically effective amount of a compound of this invention to the mammal in need thereof. The result of treatment can be partially or completely alleviating, inhibiting, preventing, ameliorating, and/or relieving the disorder, condition, or one or more symptoms thereof. Administration includes any form of administration that is known in the art to be effective for a given type of disease or disorder, is intended to encompass administration in any appropriate dosage form and further is intended to encompass administration of a compound, pharmaceutically acceptable salt, solvate, or ester thereof, alone or in a pharmaceutically acceptable carrier thereof, or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

In one preferred embodiment, the present invention provides methods for treating the diseases and conditions disclosed above comprising administering to a subject in need thereof a therapeutically effective amount of a compound of structural formula (I).

In one embodiment, the invention provides a method for treating the diseases and conditions disclosed above comprising administering to a subject in need thereof an amount of a compound of structural formula (I), or a pharmaceutically acceptable salt thereof, sufficient to treat the condition. A composition of structural formula (I) can be used as the sole therapeutic agent, or in combination with a second treatment for the condition.

In a further embodiment, the present invention provides a method for treating a disease or condition disclosed above comprising: (a) administering to an individual in need thereof an amount of a compound of structural formula (I); and (b) administering to the individual an amount of a second therapeutic agent useful in the treatment of the disease or condition. The amounts administered are each effective to treat the disease or condition. In another embodiment, the amounts are together effective to treat the disease or condition.

In another embodiment, the invention provides a method for treating a disease or condition disclosed above, said method comprising administering to a subject in need thereof a pharmaceutical composition comprising an amount of a compound of structural formula (I) effective to treat the disease or condition.

In one embodiment, a compound of structural formula (I) or a pharmaceutically acceptable salt thereof is administered prior to the administration of the second therapeutic agent.

In another embodiment, a compound of structural formula (I) or a pharmaceutically acceptable salt thereof is administered adjunctively with the second therapeutic agent.

Suitable pharmaceutical agents that can be used in combination with the compounds of structural formula (I) include anti-obesity agents, such as apolipoprotein-B secretion/microsomal triglyceride transfer protein (apo-B/MTP) inhibitors, MCR-4 agonists, cholescystokinin-A (CCKA) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists (for example, SR141716: N-(piperidin-1-yl)-5-(4-chloropheny 1)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like), and appetite suppressants (for example, bupropion). In some embodiments, the anti-obesity agents are selected from the group consisting of orlistat, sibutramine, bromocriptine, ephedrine, leptin, phentermine, and pseudoephedrine.

Other anti-obesity agents, including the agents set forth above, are well known, or will be readily apparent in light of the instant disclosure, to one of ordinary skill in the art.

It will be understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of structural (I) include agents useful in the treatment of concomitant diseases. For example, individuals that are over weight or obese increase their risk of morbidity and mortality arising from concomitant diseases, such as, but not limited to, congestive heart failure, type II diabetes, atherosclerosis, dyslipidemia, hyperinsulinemia, hypertension, insulin resistance, hyperglycemia, retinopathy, nephropathy and neuropathy. Treatment for one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In accordance to one aspect of the present invention, a compound of the present can be used in combination with a pharmaceutical agent or agents belonging to one or more of the classes of drugs cited herein.

Some embodiments of the present invention include methods of treatment of a disease, disorder, or condition as described herein comprising administering to an individual in need of such treatment a therapeutically effect amount or dose of a compound of structural formula (I) in combination with at least one pharmaceutical agent selected from the group consisting of: sulfonylureas, meglitinides, biguanides, α-glucosidase inhibitors, peroxisome proliferatorsactivated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin.

Suitable pharmaceutical agents that can be used in conjunction with compounds of structural formula (I) include α-glucosidase inhibitors. α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N(1, 3-dihydroxy-2-propyl)valiolamine (generic name; voglibose), miglitol, and α-glucosidase inhibitors known in the art.

Suitable pharmaceutical agents that can be used in conjunction with compounds of the present invention include sulfonylureas. The sulfonylureas (SU) are drugs which promote secretion of insulin from pancreatic 13 cells by transmitting signals of insulin secretion via SU receptors in the cell membranes. Examples of the sulfonylureas include glyburide, glipizide, glimepiride, and other sulfonylureas known in the art.

Suitable pharmaceutical agents that can be used in conjunction with compounds of structural formula (I) include the meglitinides. The meglitinides target postprandial hyperglycemia and show comparable efficacy to sulfonylureas in reducing $HbA_{1c}$. Examples of meglitinides include repaglinide, nateglinide, and other meglitinides known in the art.

Suitable pharmaceutical agents that can be used in conjunction with compounds of structural formula (I) include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of structural formula (I) include the α-glucosidase inhibitors. The α-glucosidase inhibitors competitively inhibit digestive enzymes, such as α-amylase, maltase, α-dextrinase, sucrase, etc., in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name voglibose), miglitol, and α-glucosidase inhibitors known in the art.

Suitable pharmaceutical agents that can be used in conjunction with compounds of structural formula (I) include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516, and PPAR-γ agonists known in the art.

Suitable pharmaceutical agents that can be used in conjunction with compounds of structural formula (I) include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of pharmaceutical agents known in the art belonging to the classes of drugs referred to, but not limited to, the following: amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds), and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy]phosphinyl]-3-phenoxybenzenebutanesulfonic acid, mono potassium salt (BMS-188494), and squalene synthesis inhibitors known in the art.

In the present method, a therapeutically effective amount of one or more compound of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms, and/or malfunctions, and other factors.

A compound of structural formula (I) can be administered by any suitable route, for example by oral, buccal, inhalation, topical, topical ophthalmic, intranasal, intrabronchial, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the disease or condition being treated, the length of time that activity is desired, and the age and the condition of the patient, and ultimately is determined by the attendant physician. Dosage amounts and intervals can be adjusted individually to provide plasma levels of a compound/structural formula (I) that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a compound of structural formula (I) can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a compound of structural formula (I), or a composition containing the same, can be from about 1 ng/kg to about 200 mg/kg, about 1 µg/kg to about 100 mg/kg, or about 1 mg/kg to about 50 mg/kg of body weight. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 g/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A compound of structural formula (I) used in a method of the present invention typically is administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

The term "carrier" refers to a diluent, adjuvant, or excipient, with which a compound of structural formula (I) is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a compound of structural formula (I) is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a compound of structural formula (I) is administered orally, the composition typically is in the form of a tablet, capsule, powder, solution, pill, granule, tincture, emulsion, syrup, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A compound of structural formula (I) can be infused with other fluids over a 10-30 minute span or over several hours.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulating agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, a compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the compounds of structural formula (I) are best used in the form of a sterile aqueous solution which can contain other substances, for example, salts or monosaccharides, such as mannitol or glucose, to make the solution isotonic with blood.

Compounds of structural formula (I) were prepared and assayed for an ability to modulate the activity of the 5-HT(2) family of receptors. In particular, compounds were prepared and assayed to determine effects on the 5-HT(2) family of receptors. The methods are described below and the results are summarized in Table 3.

Pharmacological Test of Selected Compounds in Calcium Flux Assay.

$5-HT_{2A}$, $5-HT_{2B}$ and $5-HT_{2C\text{-}INI}$ receptors expressed on HEK-293 cells Flp-In-293 cells stably expressing the human $5-HT_{2A}$, $5-HT_{2B}$, or $5-HT_{2C\text{-}INI}$ were grown 24-48 h in DMEM containing 10% dialyzed FBS before seeding. Cells were plated into Poly-$_L$-Lys-coated 384-well black clear bottom cell culture plates in DMEM with 1% dialyzed FBS at a density of 12 000 cells per 50 µL per well for 24 h. Preceding the experiment, culture medium was removed and 20 µL of assay buffer (20 mM Hepes, pH 7.40, Hanks' balanced salt solution, 2.5 mM probenecid, 1×FLIPR calcium dye) was added and cells were incubated at 37° C. for 1 h. Serial dilutions of each tested drug were prepared at 3× final concentration and transferred to 384-well plates. Each drug plate contained 5-HT and lorcaserin in serial dilutions for internal reference. Cell and drug plates were placed in a FLIPR$^{TETRA}$ fluorescence imaging plate reader (Molecular Dynamics). The FLIPR$^{TETRA}$ was programmed to read baseline for 10 sec (1 read/sec) and then add 10 μL of drug/well and read additional 120 sec. Fluorescence was normalized to the average of the baseline (first 10 reads) and the maximum fold increase peak was determined for each drug and controls (5-HT and lorcaserin). Data were plotted as a function of drug concentration and were normalized compared to the internal 5-HT reference for each plate recorded. Normalized data were regressed using a sigmoidal dose-response function. Data of two independent experiments (n=2) conducted in quadruplicate are presented. Analyses were performed using the software from GraphPad Prism 6.0. 5-HT$_{2C}$ EC$_{50}$ confidence intervals (5-HT: 0.16-0.26 nM; lorcaserin: 3.1-3.9 nM), E$_{max}$ Std. Error (5-HT: 100%±1.04; lorcaserin: 99%±0.75); 5-HT$_{2B}$ EC$_{50}$ confidence intervals (5-HT: 0.66-1.17 nM; lorcaserin: 429-527 nM), E$_{max}$ Std. Error (5-HT: 100%±1.69; lorcaserin: 92%±3.01); 5-HT$_{2A}$ EC$_{50}$ confidence intervals (5-HT: 1.60-2.16 nM; lorcaserin: 275-329 nM), E$_{max}$ Std. Error (5-HT: 100%±1.03; lorcaserin: 68%±0.83).

| Compound ID | EC$_{50}$, nM (E$_{max}$, % 5-HT) | | |
|---|---|---|---|
| | 5-HT$_{2C}$ | 5-HT$_{2B}$ | 5-HT$_{2A}$ |
| 5-HT | 0.21 (100%) | 0.92 (100%) | 1.88 (100%) |
| lorcaserin | 3.6 (99%) | 478 (68%) | 302 (68%) |
| (−)-Example 1 | 16 (99%) | 329 (44%) | 235 (88%) |
| (+)-Example 1 | 7.6 (97%) | 25 (59%) | 81 (93%) |
| (−)-Example 2 | 118 (92%) | NA | 1240 (18%) |
| (+)-Example 2 | 4.1 (92%) | 286 (82%) | 194 (66%) |
| (−)-Example 3 | 588 (86%) $^a$ | NA | NT |
| (+)-Example 3 | 56 (91%) $^a$ | NT | NT |
| (−)-Example 4 | 776 (70%) | 2521 (26%) | NA |
| (+)-Example 4 | 24 (87%) | 506 (39%) | 654 (41%) |
| (−)-Example 5 | 308 (77%) | 1957 (22%) | NA |
| (+)-Example 5 | 42 (87%) | 1001 (44%) | NA |
| (−)-Example 6 | 117 (92%) | 4209 (33%) | NA |
| (+)-Example 6 | 67 (80%) | 1005 (30%) | 628 (22%) |
| (−)-Example 7 | 296 (80%) | 735 (11%) | NA |
| (+)-Example 7 | 11 (88%) | 1994 (33%) | 1025 (15%) |
| (−)-Example 8 | 157 (87%) | NA | 697 (56%) |
| (+)-Example 8 | 4.2 (87%) | NA | 374 (56%) |
| (−)-Example 9 | 985 (62%) | NA | NA |
| (+)-Example 9 | 22 (91%) | NA | 1666 (17%) |
| (−)-Example 10 | 514 (77%) | NA | 2994 (20%) |
| (+)-Example 10 | 3.4 (89%) | NA | 359 (76%) |
| (−)-Example 11 | 646 (72%) | 2307 (26%) | NA |
| (+)-Example 11 | 13 (91%) | 86 (45%) | 1215 (49%) |
| (−)-Example 12 | 1228 (31%) | 3004 (21%) | NA |
| (+)-Example 12 | 103 (72%) | 3436 (25%) | NA |
| (−)-Example 13 | NA $^a$ | NA | NA |
| (+)-Example 13 | NA $^a$ | NA | NA |
| (−)-Example 14 | 2481 (37%) | 5660 (19%) | NA |
| (+)-Example 14 | 91 (86%) | 997 (37%) | 4002 (19%) |
| (−)-Example 15 | NA $^a$ | NT | NT |
| (+)-Example 15 | NA $^a$ | NT | NT |
| (−)-Example 16 | NA $^a$ | NT | NT |
| (+)-Example 16 | NA $^a$ | NT | NT |
| (−)-Example 17 | 667 (45%) | 5300 (32%) | NA |
| (+)-Example 17 | 183 (8%) | NA | NA |
| (−)-Example 18 | 1762 (11%) | NA | NA |
| (+)-Example 18 | 244 (24%) | NA | NA |
| (−)-Example 19 | 1127 (59%) | 4521 (31%) | NA |
| (+)-Example 19 | 32 (86%) | 632 (31%) | 1476 (35%) |
| (−)-Example 20 | 1258 (24%) | 6166 (22%) | NA |
| (+)-Example 20 | 206 (60%) | 4911 (22%) | NA |
| (−)-Example 21 | 914 (64%) | 1485 (30%) | 1305 (43%) |
| (+)-Example 21 | 91 (81%) | 839 (27%) | 1811 (31%) |

-continued

| Compound ID | EC$_{50}$, nM (E$_{max}$, % 5-HT) | | |
|---|---|---|---|
| | 5-HT$_{2C}$ | 5-HT$_{2B}$ | 5-HT$_{2A}$ |
| (−)-Example 22 | NA $^a$ | NT | NT |
| (+)-Example 22 | 495 (85%) $^a$ | NT | NT |
| (−)-Example 23 | 737 (42%) | 4295 (28%) | NA |
| (+)-Example 23 | 60 (80%) | 2211 (32%) | NA |
| (−)-Example 24 | NA | 6094 (39%) | NA |
| (+)-Example 24 | 212 (90%) | 422 (32%) | 903 (26%) |
| (−)-Example 25 | NA | 6877 (33%) | NA |
| (+)-Example 25 | 133 (81%) | 1688 (27%) | NA |
| (−)-Example 26 | 365 (71%) | 4411 (30%) | NA |
| (+)-Example 26 | 63 (65%) | 4602 (29%) | 1005 (21%) |
| (−)-Example 27 | 3962 (42%) $^a$ | NT | NT |
| (+)-Example 27 | 1800 (79%) $^a$ | NT | NT |
| (−)-Example 28 | 1537 (51%) $^a$ | NT | NT |
| (+)-Example 28 | NA $^a$ | NT | NT |
| (−)-Example 29 | 3.8 (93%) | 165 (64%) | 68 (86%) |
| (+)-Example 29 | 13 (92%) | 354 (52%) | 212 (85%) |
| (−)-Example 30 | 97 (90%) | 7422 (51%) | 819 (31%) |
| (+)-Example 30 | 28 (89%) | 900 (36%) | 820 (53%) |
| (−)-Example 31 | 386 (80%) | NA (0%) | NA (5%) |
| (+)-Example 31 | 71 (86%) | NA (15%) | 934 (40%) |
| (−)-Example 32 | 165 (87%) | NA (5%) | 1081 (16%) |
| (+)-Example 32 | 116 (90%) | 6983 (69%) | NA (12%) |
| (−)-Example 33 | 14 (89%) | 696 (16%) | 84 (75%) |
| (+)-Example 33 | 9.7 (95%) | 31 (45%) | 21 (85%) |
| (−)-Example 34 | 435 (75%) | NA (12%) | NA (4%) |
| (+)-Example 34 | 18 (87%) | 15380 (40%) | 92 (58%) |
| (−)-Example 35 | 278 (84%) | NA (14%) | NA (11%) |
| (+)-Example 35 | 61 (88%) | 714 (26%) | 167 (37%) |
| (−)-Example 36 | 0.95 (104%) | 51 (62%) | 38 (88%) |
| (+)-Example 36 | 21 (98%) | 534 (46%) | 203 (76%) |
| (−)-Example 37 | 30 (104%) | 6834 (53%) | 625 (12%) |
| (+)-Example 37 | 91 (101%) | 1314 (61%) | 976 (32%) |
| (−)-Example 38 | 224 (85%) | 10370 (62%) | NA |
| (+)-Example 38 | 232 (90%) | 5523 (99%) | 949 (22%) |
| (−)-Example 39 | 108 (93%) | 3962 (99%) | 426 (32%) |
| (+)-Example 39 | 165 (70%) | NA | NA |
| (−)-Example 40 | 30 (104%) | 400 (59%) | 511 (76%) |
| (+)-Example 40 | 3.4 (108%) | 27 (69%) | 81 (81%) |
| (−)-Example 41 | 33 (103%) | 299 (35%) | 778 (52%) |
| (+)-Example 41 | 2.9 (105%) | 55 (59%) | 260 (69%) |
| (−)-Example 42 | 772 (73%) | NA | NA |
| (+)-Example 42 | 7.3 (95%) | 453 (32%) | 361 (51%) |
| (−)-Example 43 | 119 (89%) | 2966 (13%) | NA |
| (+)-Example 43 | 26 (93%) | 2543 (24%) | 805 (23%) |
| (−)-Example 44 | 116 (94%) | NA | 831 (17%) |
| (+)-Example 44 | 8.7 (97%) | 1745 (35%) | 491 (21%) |
| (−)-Example 45 | 16 (108%) | 462 (62%) | 461 (72%) |
| (+)-Example 45 | 9.5 (108%) | 209 (64%) | 437 (79%) |
| (−)-Example 46 | 83 (99%) | 4265 (30%) | 2147 (18%) |
| (+)-Example 46 | 7.2 (107%) | 288 (48%) | 1157 (57%) |
| (−)-Example 47 | 509 (78%) | 9871 (29%) | NA |
| (+)-Example 47 | 25 (95%) | 2182 (36%) | 2332 (30%) |
| (−)-Example 48 | 357 (68%) | NA | NA |
| (+)-Example 48 | 47 (90%) | 4225 (39%) | 2065 (18%) |
| (−)-Example 49 | 151 (89%) | 4464 (26%) | NA |
| (+)-Example 49 | 36 (100%) | 3339 (35%) | NA |
| (−)-Example 50 | 3.2 (96%) | 101 (91%) | 119 (72%) |
| (+)-Example 50 | 24 (88%) | 2176 (60%) | 769 (77%) |
| (−)-Example 51 | 38 (89%) | 1636 (33%) | NA |
| (+)-Example 51 | 22 (15%) | 760 (56%) | 761 (47%) |
| (−)-Example 52 | 135 (80%) | 3486 (29%) | NA |
| (+)-Example 52 | 49 (86%) | 961 (55%) | 798 (39% |
| (−)-Example 53 | 101 (89%) | 5176 (57%) | NA |
| (+)-Example 53 | 96 (92%) | 927 (55%) | NA |

Rat 5-HT$_{2C-INI}$ Receptors Expressed on PO1C Cells

Rat PO1C cell line stably expressing the rat 5-HT$_{2C-INI}$ was plated onto Poly-$_L$-Lys-coated 384-well black clear bottom cell culture plates in DMEM 1% dialyzed FBS (12 000 cells/well). Preceding the experiment, culture medium was removed and 20 μl of assay buffer (20 mM Hepes, pH 7.40, Hanks' balanced salt solution, 2.5 mM probenecid, 1×FLIPR calcium dye) was added and cells incubated at 37° C. for 1 h. Serial dilution of each tested drugs were prepared at 3× final concentration and transfer to a 384-well plates. Cell and drug plates were placed in a FLIPR$^{TETRA}$ fluorescence imaging plate reader (Molecular Dynamics) and programmed to read baseline for 10 sec (1 read/s) and then add 10 µl of drug/well and to read additional 120 sec. Fluorescence was normalized to the average of the baseline (first 10 reads) and the maximum fold increase peak was determined for each drug and controls (5-HT). Data were plotted and normalized compared to 5-HT and regressed using sigmoidal dose-response function. Data of two independent experiments (n=2) conducted in quadruplicate are presented. Analyses were performed using the software GraphPad Prism 6.0.

Table 3.

Pharmacological profiles of selected compounds using recombinant, stably expressed human 5-HT$_{2A}$, 5-HT$_{2B}$ and 5-HT$_{2C-INI}$ receptors in the HEK-293 cell line, using a fluorescence imaging plate reader (FLIPR) assay ("NA", no activity at 10 µM; "NT", not tested; $^a$, data acquired with rat 5-HT$_{2C-INI}$ receptors expressed on PO1C cells):

In Vivo Test in a Schizophrenia-Like Animal Model.

Adult male C57BL/6J mice (Jackson Laboratories, Bar Harbor, Me.) were injected (i.p.) with the vehicle (Veh) or different doses of the compounds and placed into the open field for 15 min. The mice were removed and administered (i.p.) the Veh or 3 mg/kg amphetamine (AMPH; Sigma-Aldrich, St. Louis, Mo.) and returned to the open field for 105 min. Locomotor activity was monitored as distance travelled in an automated Omnitech Digiscan apparatus using VersaMax software (AccuScan Instruments, Columbus, Ohio). The results are presented as means and standard errors of the mean using SPSS software (IBM, Armonk, N.Y.). The data from the 0-15 min interval were analyzed by three-way ANOVA for condition (vehicle and AMPH), treatment, dose (10 or 20 mg/kg), and dose nested in treatment (to reflect the different doses tested per compound). Since activities among the groups at the 0-15 min interval were significantly different, a RMAOVA was run with a sequential sum of squares (to control for the group differences at 0-15 min) for test interval (0-15 and 16-120 min), condition, treatment, dose, and dose (treatment) to control for these group differences. All post-hoc analyses were by Bonferroni corrected pair-wise comparisons where a p<0.05 was considered significant.

Compounds (+)-Example 25, (+)-Example 19, (+)-Example 8, and (+)-Example 10 were tested in this model. Adult male C57BL/6J mice were given the vehicle (Veh) or one of the test compounds and were placed into the open field for 15 min. They were removed and administered the Veh or d-amphetamine (AMPH) and returned immediately to the open field for 105 min. As shown in the FIGURE below, d-amphetamine significantly increased locomotor activity from 16-120 min in the Veh-AMPH compared to the Veh-Veh group. Administration of each of the four compounds at the 10 or 20 mg/kg doses significantly reduced the AMPH-stimulated hyperlocomotion relative to the Veh-AMPH group (p-values<0.035). Although responses to 10 and 20 mg/kg (+)-Example 19 and (+)-Example 10 were not differentiated by dose, compounds (+)-Example 25 and (+)-Example 8 dose-dependently suppressed the hyperactivity such that locomotion at the 20 mg/kg doses was similar to that of the Veh-Veh group. Importantly, the 20 mg/kg dose of each the four compounds alone (20-Veh groups) had little influence on the spontaneous activity of the injected animals.

REFERENCES

1. M. Berger et al., *Annual review of medicine* 2009, 60, 355-66.
2. D. E. Nichols et al., *Chemical reviews* 2008, 108 (5), 1614-41.
3. (a) H. Y. Meltzer et al., *The Journal of clinical investigation* 2013, 123 (12), 4986-91; (b) B. M. Smith et al., *Expert opinion on investigational drugs* 2006, 15 (3), 257-66; (c) B. J. Sargent et al., *Current opinion in pharmacology* 2011, 11 (1), 52-8; (d) S. Rosenzweig-Lipson et al., *Handbook of experimental pharmacology* 2012, (213), 147-65; (e) C. Mombereau et al., *Neuropharmacology* 2010, 59 (6), 468-73.
4. (a) A. Pazos et al., *European journal of pharmacology* 1984, 106 (3), 539-46; (b) K. A. Berg et al., *Neuropharmacology* 2008, 55 (6), 969-76.
5. D. E. Nichols, *Pharmacology & therapeutics* 2004, 101 (2), 131-81.
6. J. Lee et al., *Expert opinion on therapeutic patents* 2010, 20 (11), 1429-55.
7. W. J. Thomsen et al., *The Journal of pharmacology and experimental therapeutics* 2008, 325 (2), 577-87.
8. Lorcaserin. In obesity: unacceptable risks. *Prescrire international* 2014, 23 (149), 117-20.
9. J. Liu et al., *CPT pharmacometrics & systems pharmacology* 2014, 3, e111.
10. J. Dunlop et al., *The Journal of pharmacology and experimental therapeutics* 2011, 337 (3), 673-80.
11. K. L. Marquis et al., *The Journal of pharmacology and experimental therapeutics* 2007, 320 (1), 486-96.
12. J. A. Siuciak et al., *Neuropharmacology* 2007, 52 (2), 279-90.
13. A. S. Kalgutkar et al., *Drug metabolism and disposition: the biological fate of chemicals* 2007, 35 (6), 848-58.
14. (a) P. M. Callahan et al., *European journal of pharmacology* 1994, 257 (1-2), 27-38; (b) D. Fiorella et al., *Psychopharmacology* 1995, 122 (3), 237-43.
15. S. J. Cho et al., *Journal of medicinal chemistry* 2009, 52 (7), 1885-902.
16. A. P. Kozikowski et al., *Chem Med Chem* 2010, 5 (8), 1221-5.
17. G. Chen et al., *ACS medicinal chemistry letters* 2011, 2 (12), 929-932.
18. K. Yamazaki et al., *Journal of pharmaceutical sciences* 2004, 93 (6), 1480-94.
19. A. M. Aronov, *Drug discovery today* 2005, 10 (2), 149-55.
20. M. J. et al., *Neuropharmacology* 1998, 37 (7), 953-5.
21. G. Di Giovanni et al., *Synapse* 2000, 35 (1), 53-61.
22. J. E. Leysen, *Current drug targets. CNS and neurological disorders* 2004, 3 (1), 11-26.
23. D. Wacker et al., *Science* 2013, 340 (6132), 615-9.

What is claimed:

1. A compound having a structural formula:

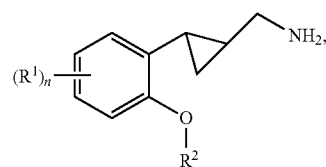

wherein $R^1$ is halo;
$R^2$ is $C_{1-5}$alkyl, fluorinated $C_{1-3}$alkyl, phenyl, benzyl,

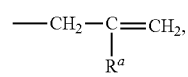

—CH$_2$—C≡CH, or —(CH$_2$)$_{1-3}$XCH$_3$;

X is O or S;

R$^a$ is hydrogen, fluoro, or C$_{1-3}$alkyl; and n is an integer 1, 2, or 3, wherein when R$^2$ is methyl and n is 1, then R$^1$ is chloro; and when R$^2$ is methyl and n is 2, then at least one R$^1$ is chloro, or a pharmaceutically acceptable salt or hydrate thereof.

2. The compound of claim 1 wherein R$^1$ is fluoro or chloro.

3. The compound of claim 1 wherein when n is 1, R$^1$ is fluoro or chloro, and when n is 2, R$^1$ is fluoro and fluoro, chloro and chloro, or fluoro and chloro.

4. The compound of claim 1 wherein R$^2$ is methyl, ethyl, n-propyl, isopropyl, n-butyl, iso-butyl, n-pentyl, iso-pentyl, phenyl, benzyl, —CH$_2$CH$_2$F, —CH$_2$CH$_2$CH$_2$F, —CH$_2$CHF$_2$, —CH$_2$CF$_3$, —CH$_2$CH=CH$_2$, $$-CH_2-\underset{F}{C}=CH_2, \quad -CH_2-\underset{CH_3}{C}=CH_2,$$

or —CH$_2$C≡CH.

5. The compound of claim 1 wherein R$^2$ is —CH$_2$CH$_2$—O—CH$_3$ or —CH$_2$CH$_2$—S—CH$_3$.

6. The compound of claim 1 wherein R$^1$ is F, n is 1, and R$^2$ is —CH$_2$CH$_2$CH$_3$, —CH$_2$CH=CH$_2$, $$-CH_2-\underset{F}{C}=CH_2,$$

or —CH$_2$CH$_2$F.

7. A compound selected from the group consisting of

-continued

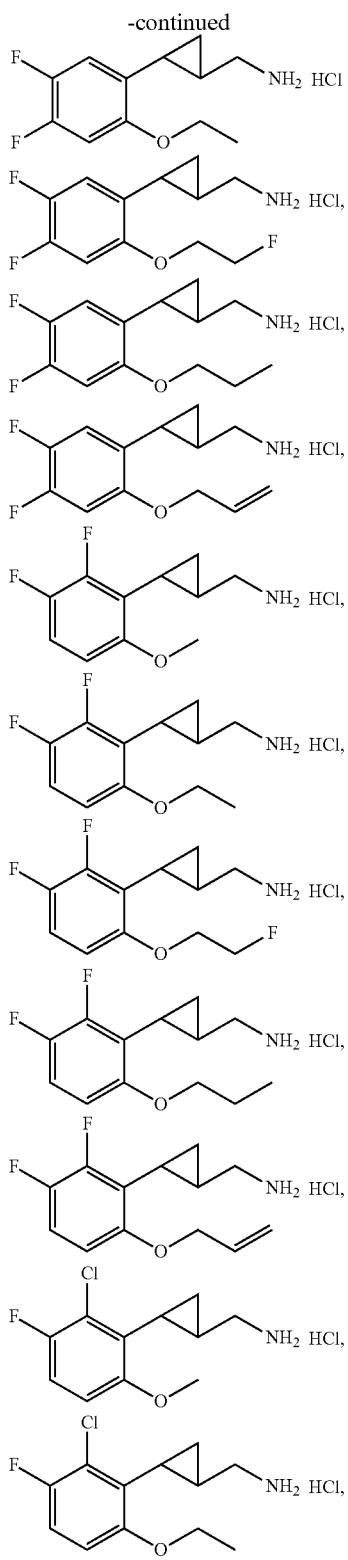

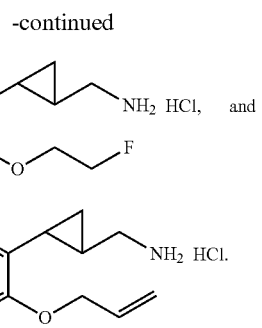

8. A compound selected from the group consisting of
(+) (2-(2-(allyloxy)-5-fluorophenyl)cyclopropyl)methanamine;
(+) (2-(5-fluoro-2-(2-fluoroethoxy)phenyl)cyclopropyl)methanamine;
(+) (2-(5-chloro-2-(3-fluoropropoxy)phenyl)cyclopropyl)methanamine; and
(+) (2-(5-chloro-2-((2-fluoroallyl)oxy)phenyl)cyclopropyl)methanamine;
or a salt thereof.

9. A composition comprising (a) compound of claim 1, (b) a second therapeutic agent, and (c) an optional excipient and/or pharmaceutically acceptable carrier.

10. A pharmaceutical composition comprising a compound of claim 1 and a pharmaceutically acceptable carrier or vehicle.

11. A method of treating a disease or condition via modulation of 5-HT(2C) receptors comprising administering a therapeutically effective amount of a compound of claim 1 to an individual in need thereof.

12. The method of claim 11 wherein the disease or condition is a central nervous system disorder, damage to the central nervous system, a metabolic or eating disorder a neurological disorder.

13. The method of claim 12 wherein the central nervous system disorder is anxiety, a panic disorder, a schizoaffective disorder, schizophrenia, psychosis, an adjustment disorder, dystonia, clinical depression, bipolar disorder, an addictive behavior, a compound addiction, obsessive compulsive disorder, a movement disorder, e a cognition disorder, dyslipidemia, Type 2 diabetes, diabetes insipidus, metabolic syndrome, obesity or Rett Syndrome.

14. The method of claim 11 wherein the disease or condition is a gastrointestinal disorder, sleep apnea, hypertension, hyperlipidemia, a cardiovascular disease, dementia, memory deficit, mild cognitive impairment, Parkinson's Disease, Alzheimer's Disease, an intellectual deficit associated with Alzheimer's disease, Huntington's Disease, dyskinesia, chronic pain, migraine, epilepsy, abuse or addiction to alcohol and drugs, or sexual dysfunction in males or females.

* * * * *